(12) United States Patent
Gabelberger et al.

(10) Patent No.: US 8,585,741 B2
(45) Date of Patent: Nov. 19, 2013

(54) CLAMPS USED FOR INTERCONNECTING A BONE ANCHOR TO A ROD

(75) Inventors: Josef Gabelberger, West Chester, PA (US); Edward McShane, Collegeville, PA (US); Daniel Vennard, Clayton, DE (US); Nicholas Angert, Paoli, PA (US); Barclay Davis, Downington, PA (US); Stefan Schwer, Loerrach (DE); Manuel Schaer, Muttenz (CH); Lee-Ann Norman, Havertown, PA (US); Reto Halbeisen, Laufen (CH); Benno Niedermann, Gallen (CH)

(73) Assignee: DePuy Synthes Products, LLC, Raynham, MA (US)

( * ) Notice: Subject to any disclaimer, the term of this patent is extended or adjusted under 35 U.S.C. 154(b) by 615 days.

(21) Appl. No.: 12/668,862

(22) PCT Filed: Jan. 25, 2008

(86) PCT No.: PCT/US2008/052046
§ 371 (c)(1),
(2), (4) Date: Jun. 28, 2010

(87) PCT Pub. No.: WO2009/011929
PCT Pub. Date: Jan. 22, 2009

(65) Prior Publication Data
US 2010/0268279 A1 Oct. 21, 2010

Related U.S. Application Data

(60) Provisional application No. 60/950,809, filed on Jul. 19, 2007.

(30) Foreign Application Priority Data

Jul. 27, 2007 (WO) ................ PCT/US2007/074633

(51) Int. Cl.
*A61B 17/70* (2006.01)
*A61B 17/58* (2006.01)
(52) U.S. Cl.
USPC ............................................ 606/264; 606/60
(58) Field of Classification Search
USPC ........... 606/60, 250–260, 264–279, 300–309, 606/319–320, 328
See application file for complete search history.

(56) References Cited

U.S. PATENT DOCUMENTS 5,047,029 A 9/1991 Aebi et al.
5,344,422 A 9/1994 Frigg
(Continued)

FOREIGN PATENT DOCUMENTS

AU 697705 3/1996
DE 9215561 U1 2/1993
(Continued)

OTHER PUBLICATIONS

USS Fracture System Technique Guide dated 2001.

*Primary Examiner* — Ellen C Hammond
*Assistant Examiner* — Jacqueline Johanas
(74) *Attorney, Agent, or Firm* — Woodcock Washburn LLP

(57) ABSTRACT

The present invention relates to a clamp, and, more particularly, to a clamp for securing the position of a bone anchor with respect to a longitudinal rod, preferably for use in the spine. The clamp may include a housing, a rod clamping assembly, and a bone anchor clamping assembly. The clamp preferably enables the longitudinal axis of the rod to be offset or laterally displaced from the longitudinal axis of the bone anchor. The rod clamping assembly and the bone anchor clamping assembly are preferably moveably coupled to the housing in order to provide increased flexibility to better accommodate the location and geometry of the longitudinal rod and to better accommodate bone positioning.

19 Claims, 32 Drawing Sheets

(56) References Cited

U.S. PATENT DOCUMENTS

| | | | |
|---|---|---|---|
| 5,487,744 A | 1/1996 | Howland | |
| 5,498,262 A | 3/1996 | Bryan | |
| 5,501,684 A | 3/1996 | Schlapfer et al. | |
| 5,562,661 A | 10/1996 | Yoshimi et al. | |
| 5,611,800 A | 3/1997 | Davis et al. | |
| 5,613,968 A | 3/1997 | Lin | |
| 5,624,441 A | 4/1997 | Sherman et al. | |
| 5,667,506 A | 9/1997 | Sutterlin | |
| 5,885,285 A | 3/1999 | Simonson | |
| 5,938,663 A | 8/1999 | Petreto | |
| 6,022,350 A | 2/2000 | Ganem | |
| 6,030,388 A | 2/2000 | Yoshimi et al. | |
| 6,146,383 A | 11/2000 | Studer et al. | |
| 6,179,838 B1 | 1/2001 | Fiz | |
| 6,187,005 B1 | 2/2001 | Brace et al. | |
| 6,235,028 B1 | 5/2001 | Brumfield et al. | |
| 6,402,749 B1 | 6/2002 | Ashman | |
| 6,579,292 B2 | 6/2003 | Taylor | |
| 6,626,906 B1 | 9/2003 | Young | |
| 6,673,074 B2 | 1/2004 | Shluzas | |
| 6,676,661 B1 | 1/2004 | Martin Benlloch et al. | |
| 6,716,214 B1 | 4/2004 | Jackson | |
| 6,736,816 B2 | 5/2004 | Ritland | |
| 6,755,830 B2 | 6/2004 | Minfelde et al. | |
| 6,835,196 B2 | 12/2004 | Biedermann et al. | |
| 6,866,664 B2 | 3/2005 | Schar et al. | |
| 6,872,209 B2 | 3/2005 | Morrison | |
| 7,066,939 B2 | 6/2006 | Taylor | |
| 7,094,237 B2 | 8/2006 | Gradel et al. | |
| 7,104,992 B2 | 9/2006 | Bailey | |
| 7,166,109 B2 | 1/2007 | Biedermann et al. | |
| 7,186,255 B2 * | 3/2007 | Baynham et al. | 606/266 |
| 7,211,087 B2 | 5/2007 | Young | |
| 7,270,665 B2 | 9/2007 | Morrison et al. | |
| 7,648,522 B2 | 1/2010 | David | |
| 7,651,516 B2 | 1/2010 | Petit et al. | |
| 7,678,112 B2 * | 3/2010 | Rezach | 606/60 |
| 7,678,136 B2 | 3/2010 | Doubler et al. | |
| 7,704,270 B2 | 4/2010 | De Coninck | |
| 7,722,645 B2 | 5/2010 | Bryan | |
| 7,744,635 B2 * | 6/2010 | Sweeney et al. | 606/264 |
| 7,753,940 B2 | 7/2010 | Veldman et al. | |
| 7,763,047 B2 | 7/2010 | Ritland | |
| 7,763,054 B2 | 7/2010 | Clement et al. | |
| 7,789,897 B2 | 9/2010 | Sanders | |
| 7,799,059 B2 | 9/2010 | Kramer et al. | |
| 7,819,902 B2 | 10/2010 | Abdelgany et al. | |
| 7,837,715 B2 | 11/2010 | Petit et al. | |
| 7,850,715 B2 * | 12/2010 | Banouskou et al. | 606/246 |
| 7,850,716 B2 | 12/2010 | Taylor | |
| 7,850,719 B2 | 12/2010 | Gournay et al. | |
| 7,896,902 B2 * | 3/2011 | Jeon et al. | 606/246 |
| 8,021,398 B2 * | 9/2011 | Sweeney et al. | 606/269 |
| 8,029,546 B2 | 10/2011 | Capote et al. | |
| 8,128,665 B2 * | 3/2012 | Banouskou et al. | 606/250 |
| 8,262,702 B2 * | 9/2012 | Giger et al. | 606/252 |
| 2004/0092930 A1 | 5/2004 | Petit et al. | |
| 2004/0153068 A1 | 8/2004 | Janowski et al. | |
| 2004/0254574 A1 | 12/2004 | Morrison et al. | |
| 2005/0070901 A1 * | 3/2005 | David | 606/61 |
| 2005/0096654 A1 | 5/2005 | Lin | |
| 2005/0228382 A1 | 10/2005 | Richelsoph et al. | |
| 2006/0036252 A1 * | 2/2006 | Baynham et al. | 606/73 |
| 2006/0167455 A1 | 7/2006 | Clement et al. | |
| 2006/0206114 A1 | 9/2006 | Ensign et al. | |
| 2006/0241601 A1 | 10/2006 | Trautwein et al. | |
| 2006/0247624 A1 | 11/2006 | Banouskou et al. | |
| 2006/0253118 A1 | 11/2006 | Bailey | |
| 2007/0135817 A1 | 6/2007 | Ensign | |
| 2007/0161987 A1 | 7/2007 | Capote et al. | |
| 2007/0167946 A1 * | 7/2007 | Triplett et al. | 606/61 |
| 2008/0167688 A1 * | 7/2008 | Fauth et al. | 606/265 |
| 2009/0264926 A1 | 10/2009 | Taylor et al. | |
| 2009/0287253 A1 * | 11/2009 | Felix et al. | 606/278 |
| 2009/0326585 A1 | 12/2009 | Baccelli et al. | |
| 2010/0049253 A1 | 2/2010 | Miller | |
| 2010/0063546 A1 | 3/2010 | Miller | |
| 2010/0094346 A1 | 4/2010 | Matityahu | |
| 2010/0168796 A1 | 7/2010 | Eliasen et al. | |
| 2010/0241171 A1 | 9/2010 | Clement et al. | |
| 2012/0303062 A1 * | 11/2012 | Amstutz et al. | 606/267 |

FOREIGN PATENT DOCUMENTS

| | | |
|---|---|---|
| EP | 0814716 B1 | 1/1998 |
| EP | 0938872 B1 | 9/1999 |
| EP | 1196102 B1 | 4/2002 |
| EP | 1330196 B1 | 7/2003 |
| EP | 0814713 B1 | 4/2004 |
| EP | 1635722 B1 | 3/2006 |
| EP | 1708630 B1 | 11/2009 |
| JP | 2004-512134 | 4/2004 |
| JP | 2004-516040 | 6/2004 |
| WO | WO 02/36026 | 5/2002 |
| WO | WO 2005/020829 A1 | 3/2005 |
| WO | WO 2007/022790 | 3/2007 |
| WO | WO 2007/067443 | 6/2007 |
| WO | WO 2007/070757 | 6/2007 |
| WO | WO 2008/014477 | 1/2008 |
| WO | WO 2009/133539 A1 | 11/2009 |
| WO | WO 2010/103198 A1 | 9/2010 |
| WO | WO 2010/150140 A1 | 12/2010 |
| WO | WO 2011/012690 | 2/2011 |

* cited by examiner

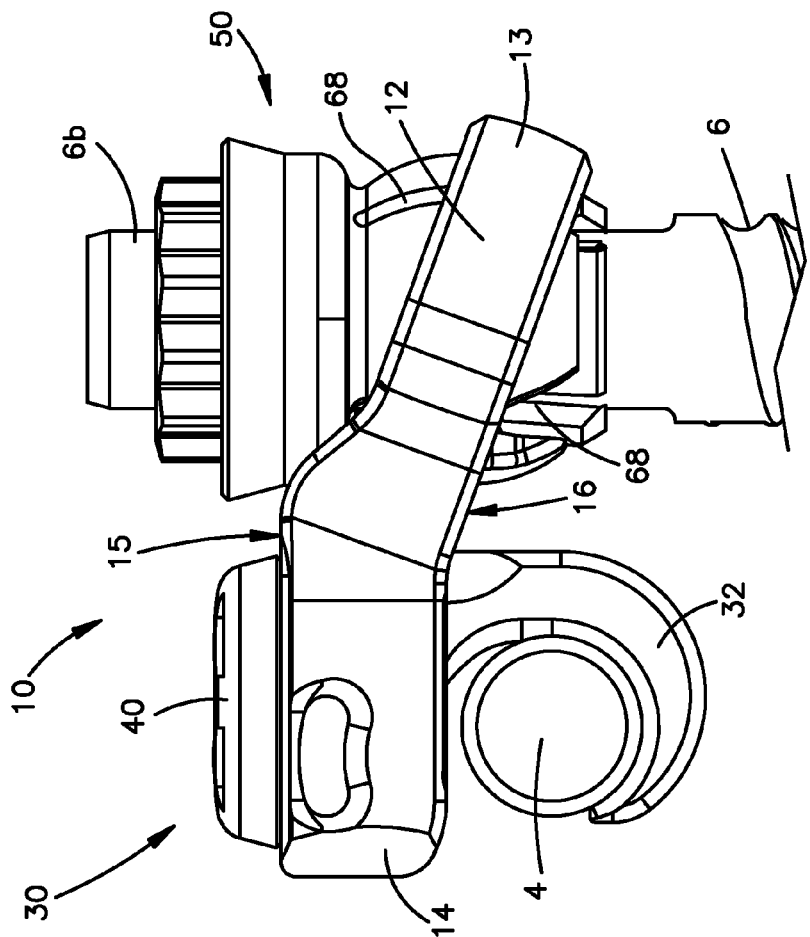
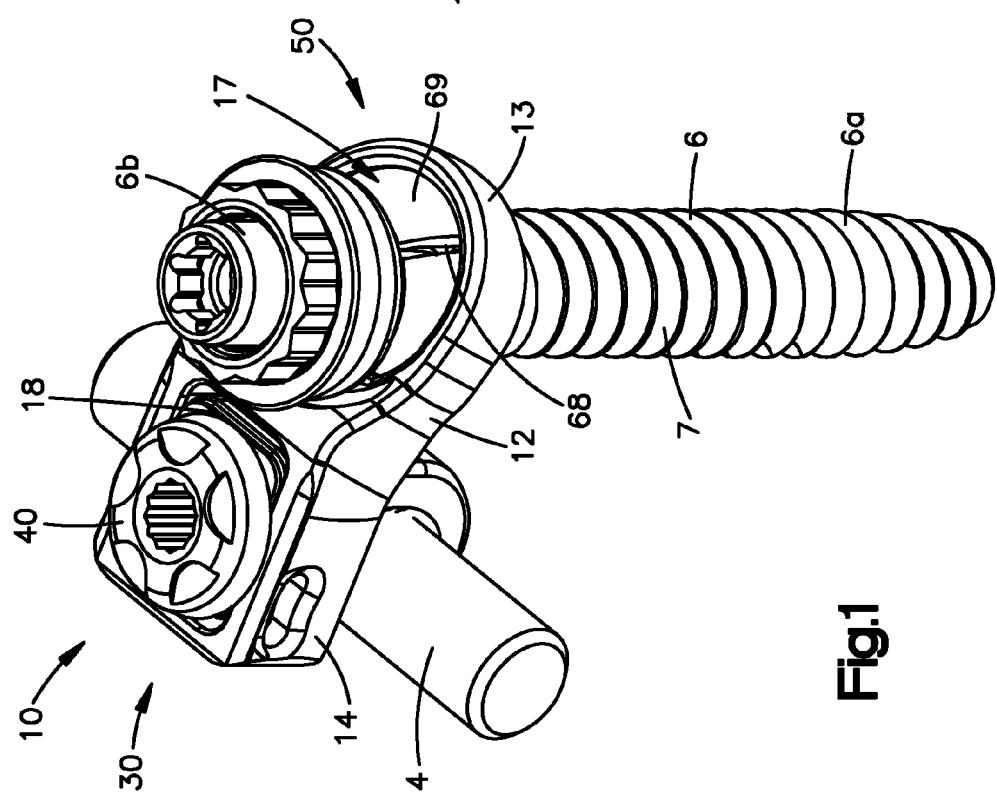
Fig.2
Fig.1

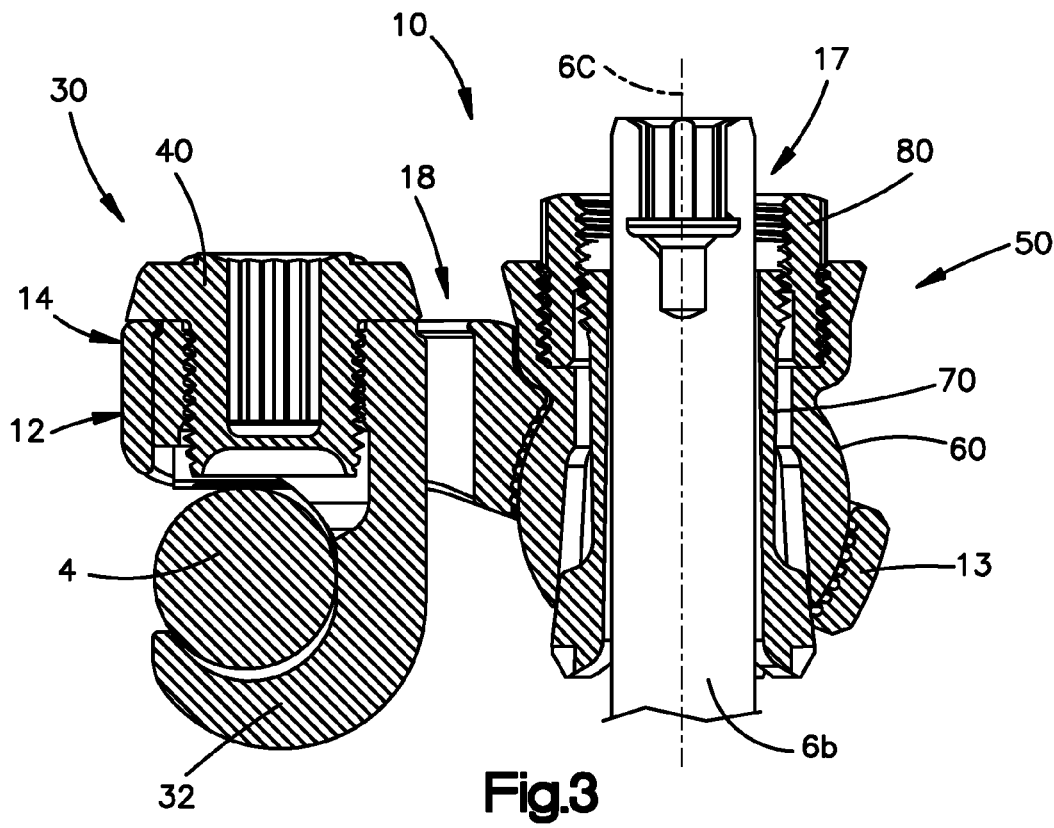
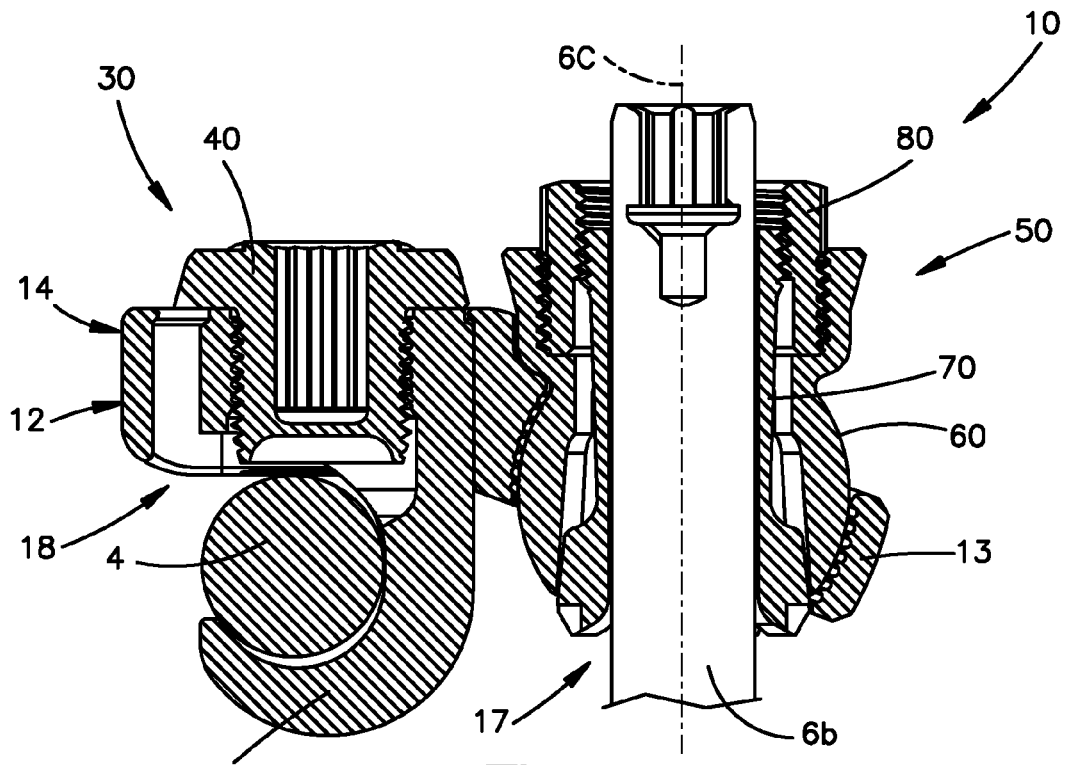

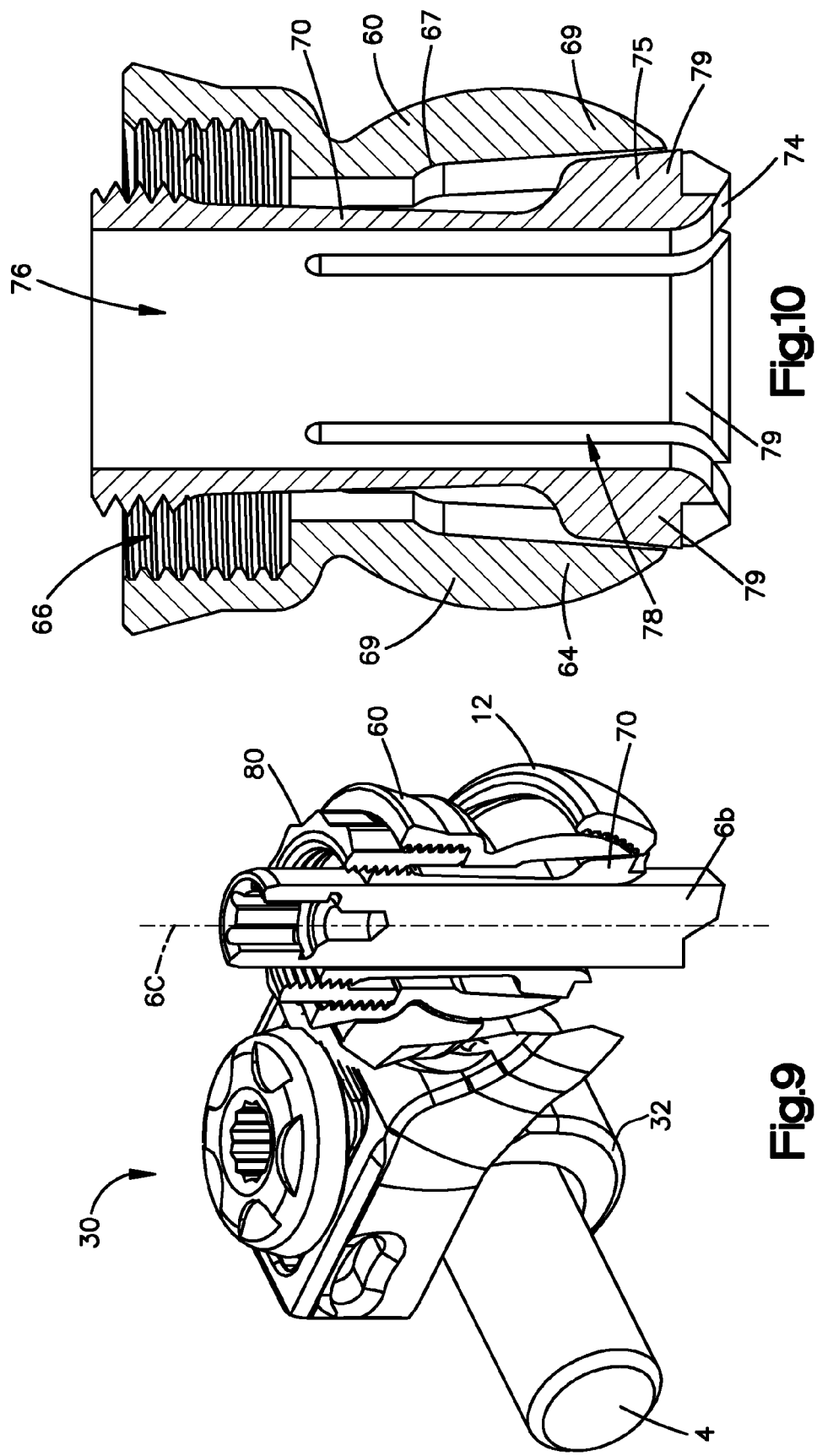

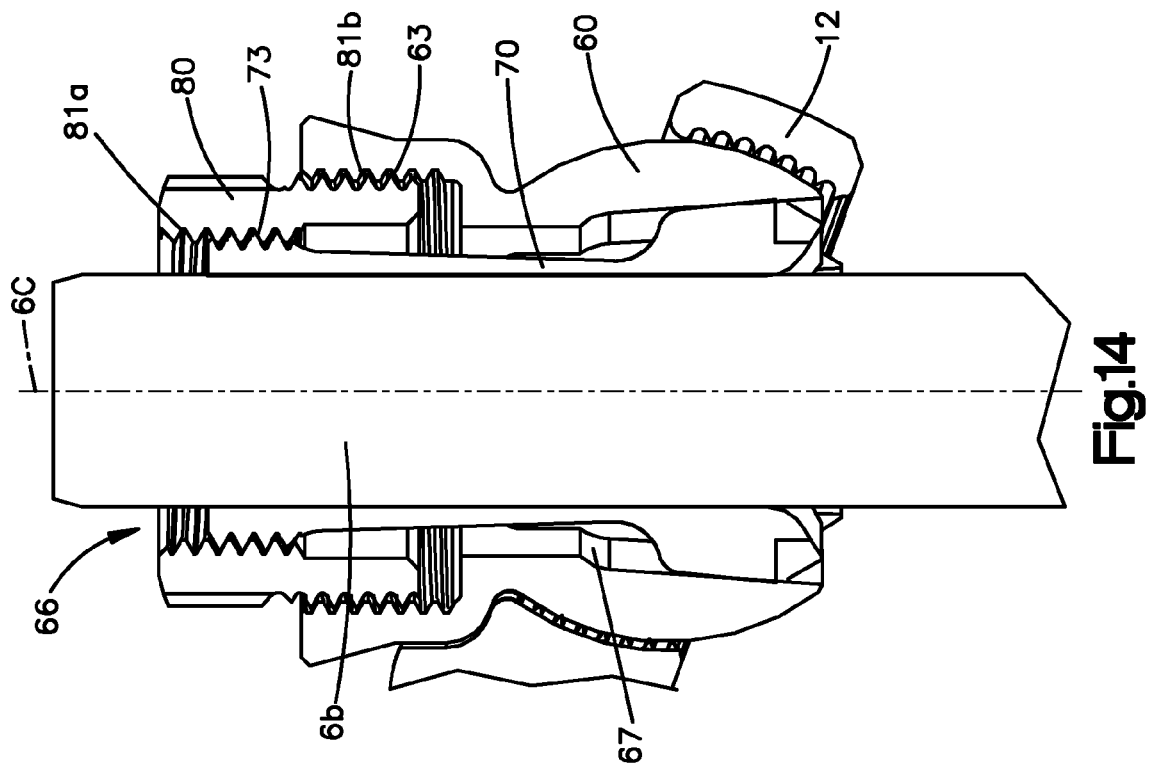
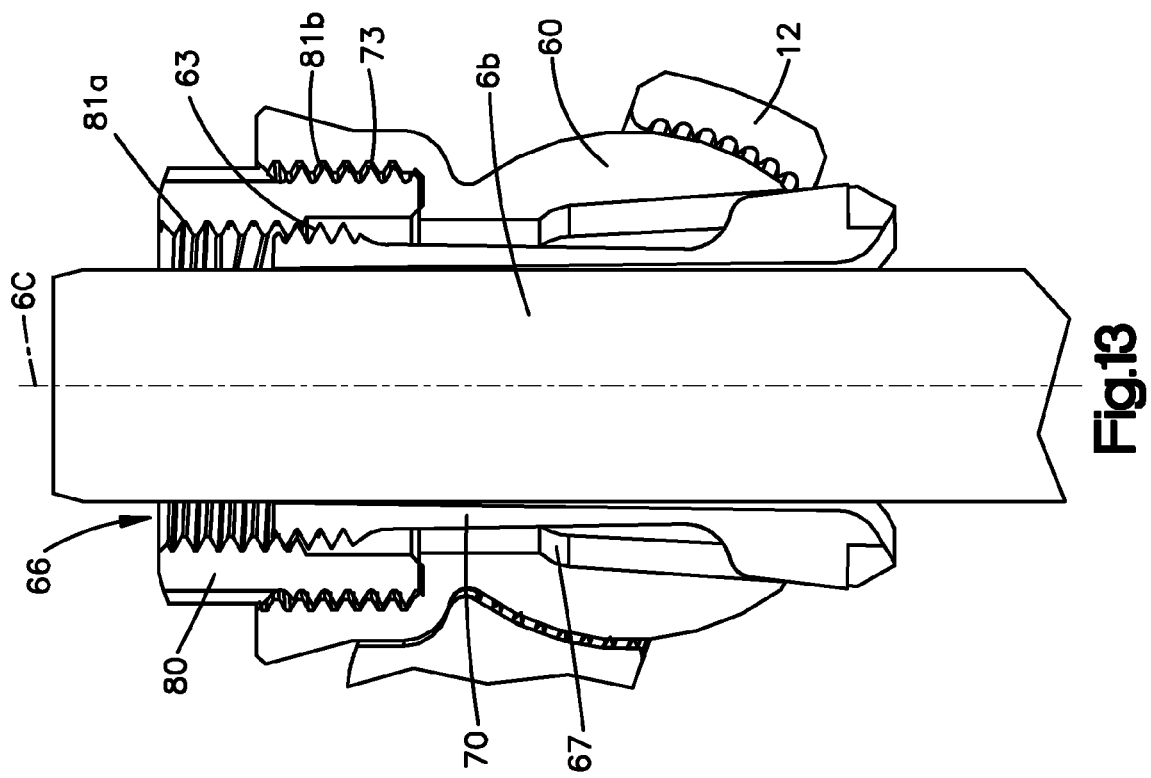

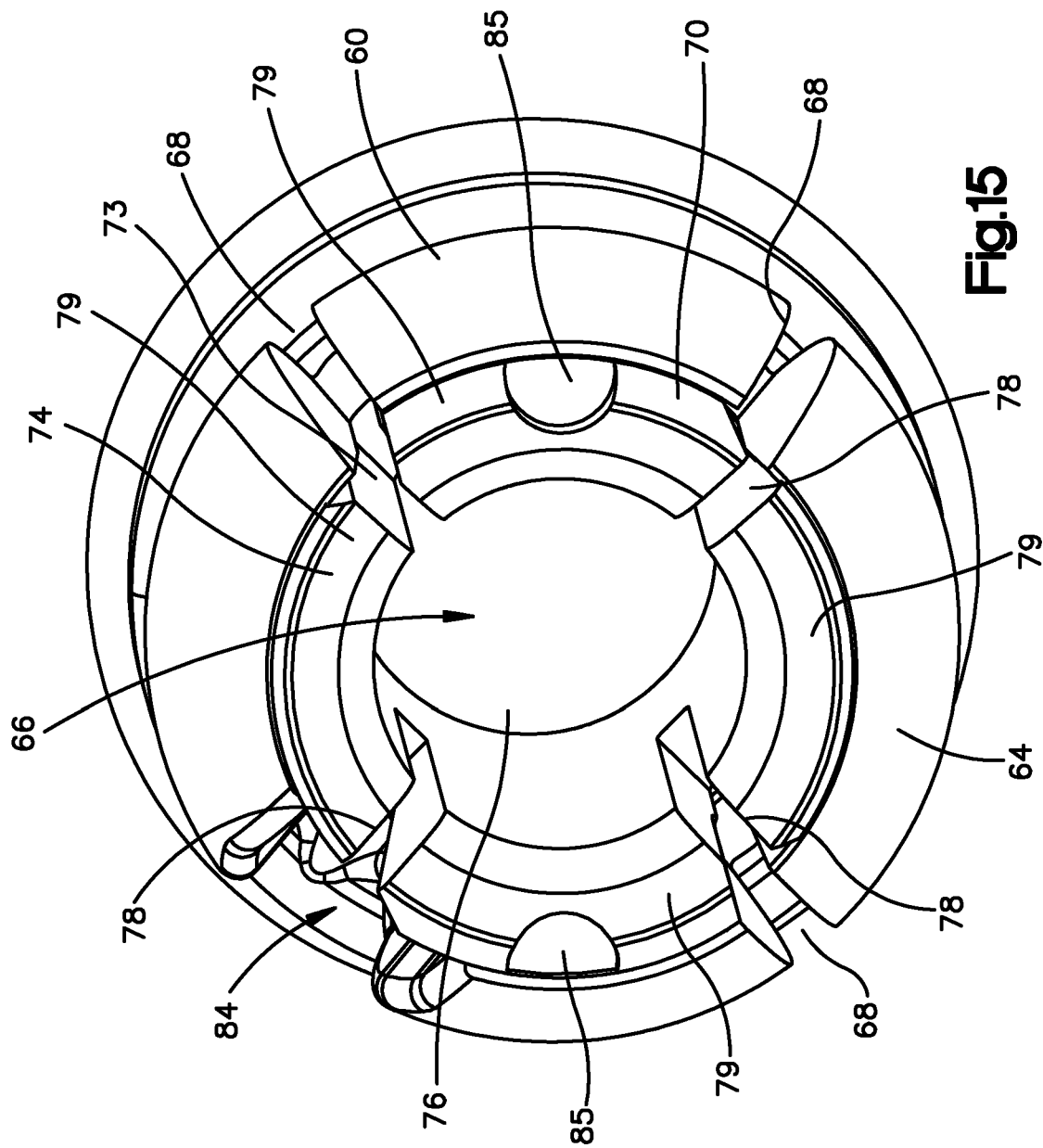

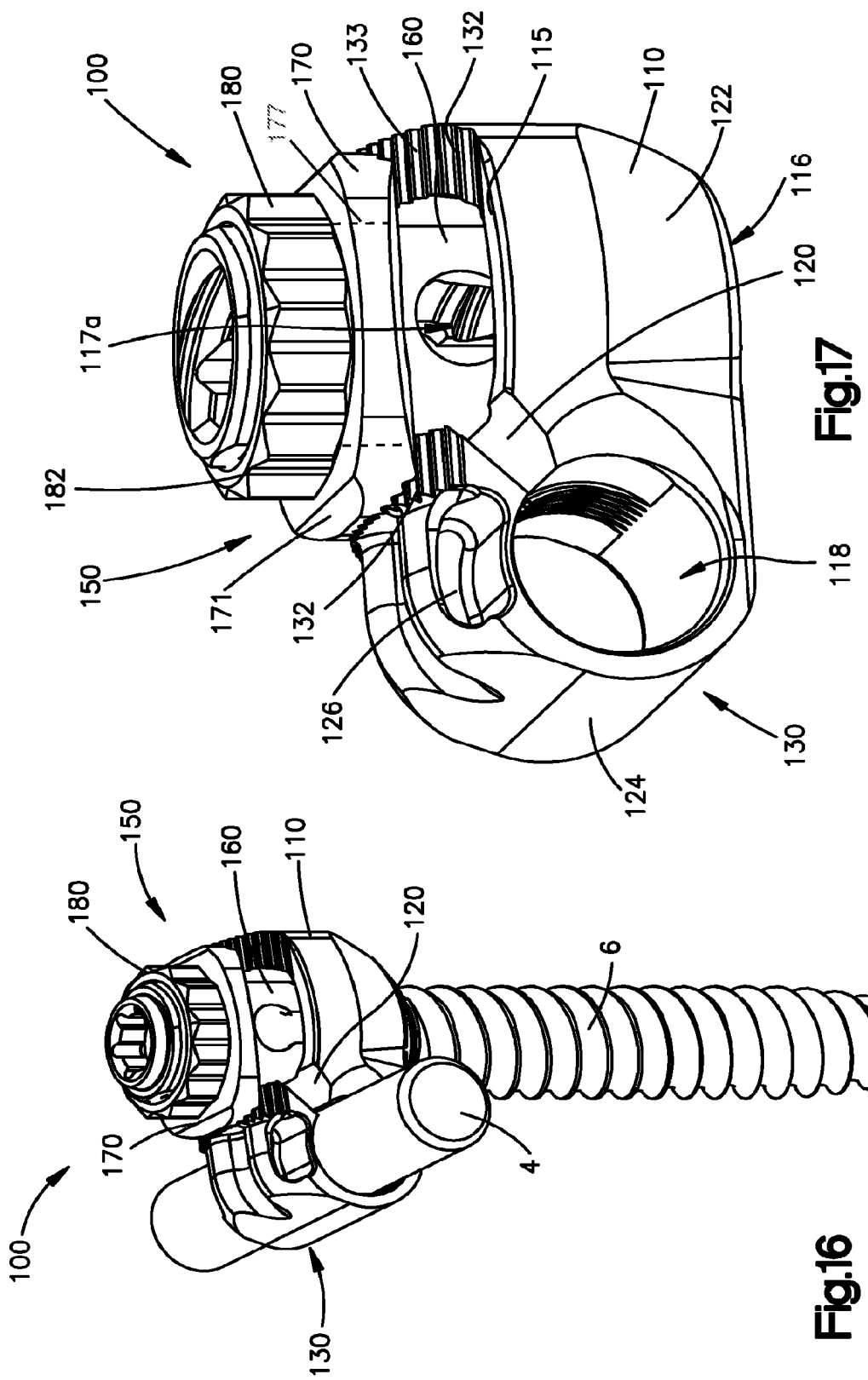

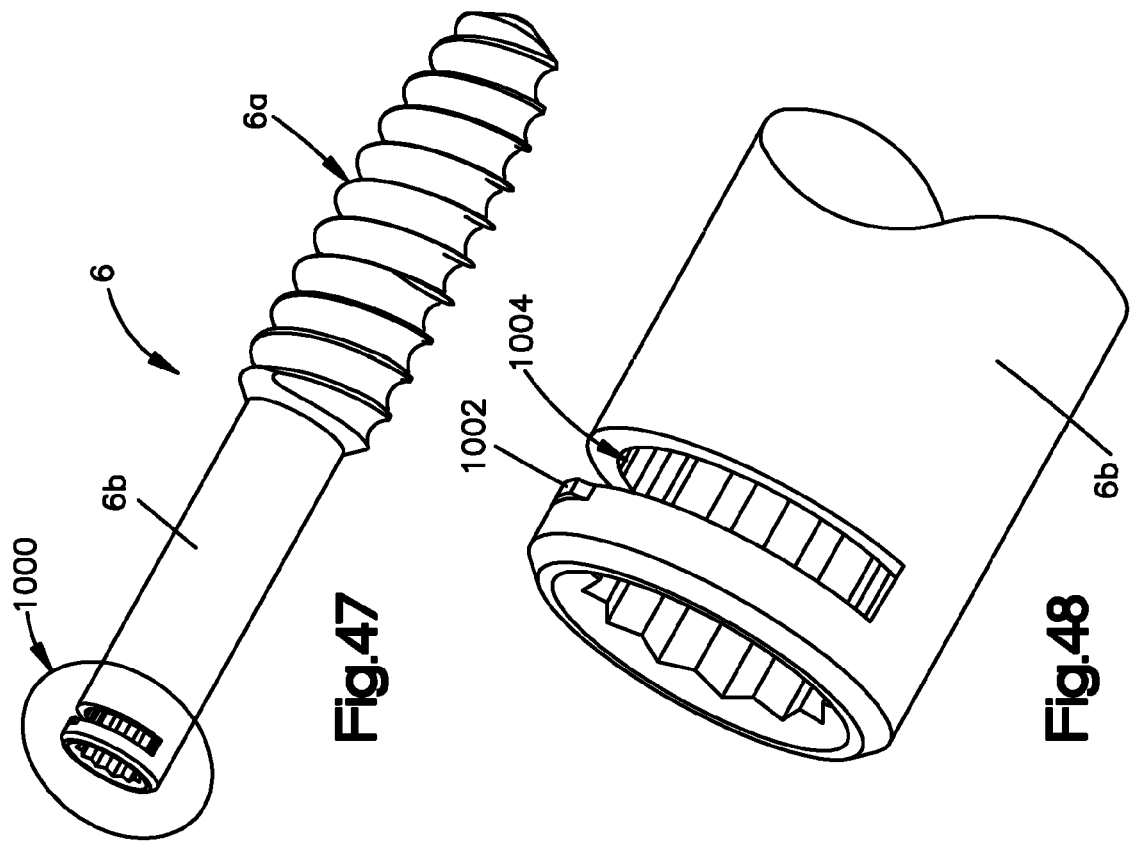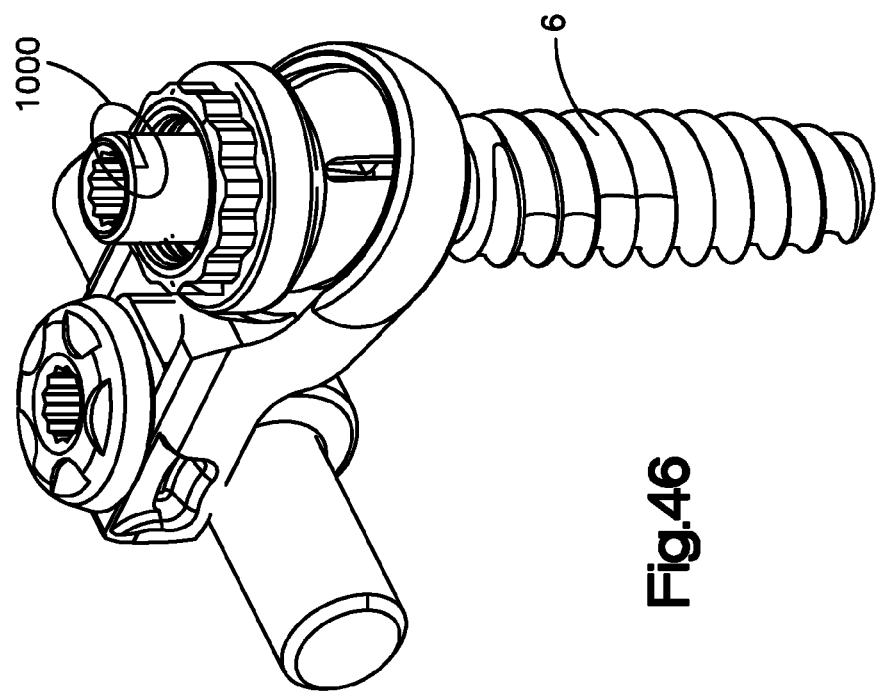

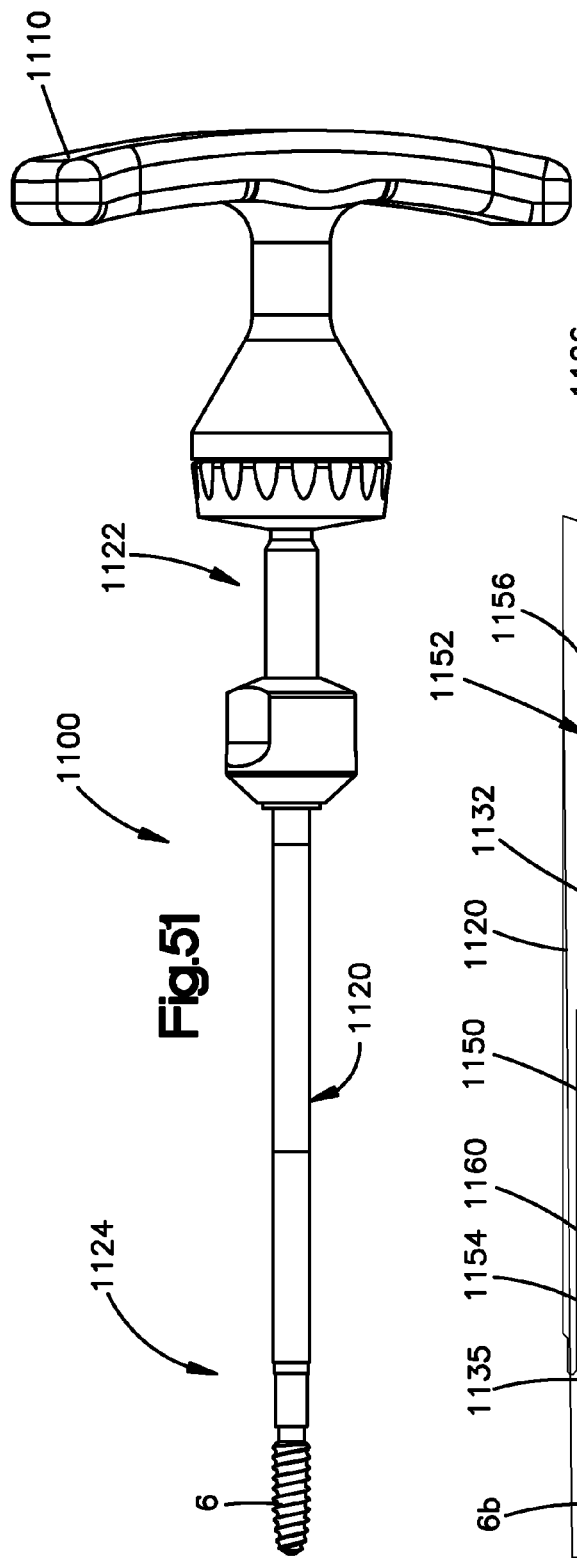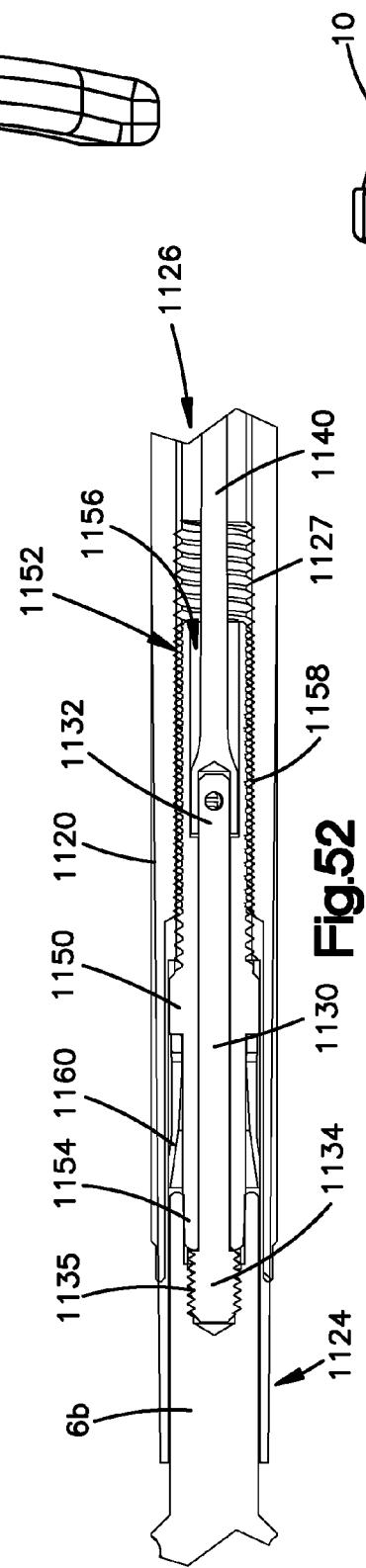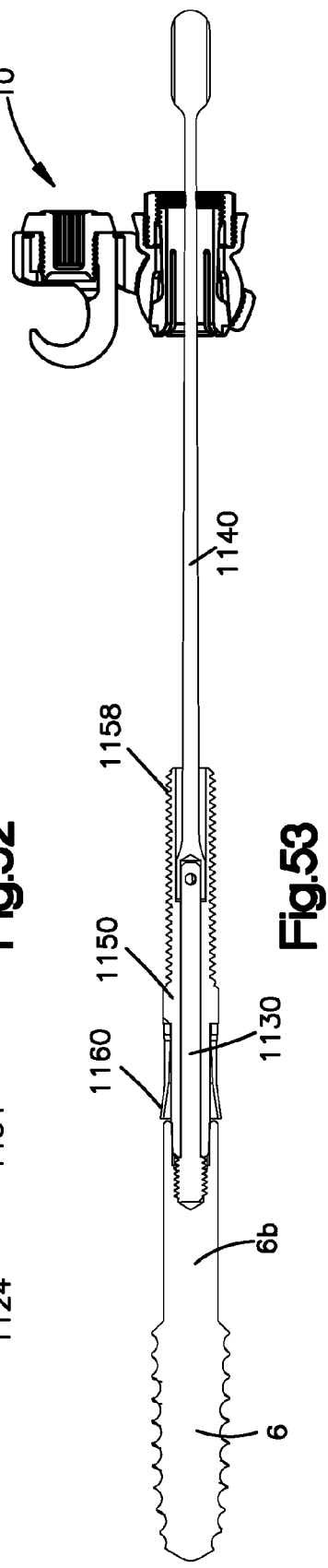

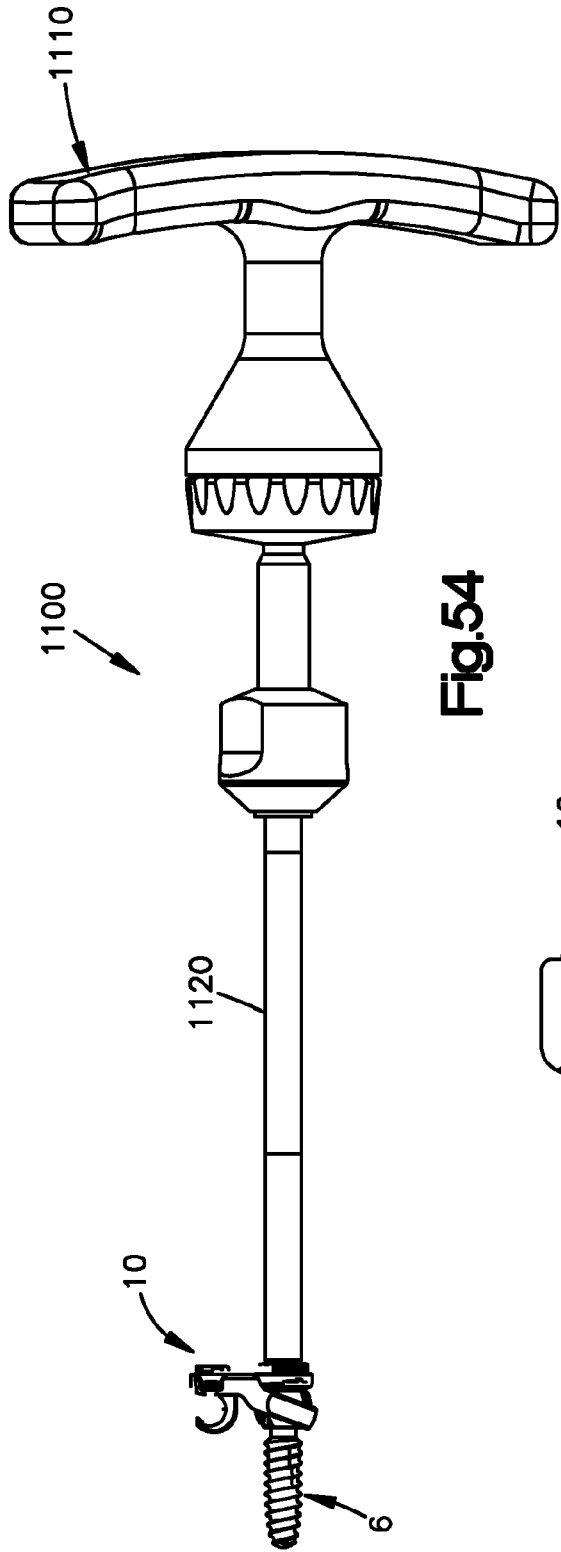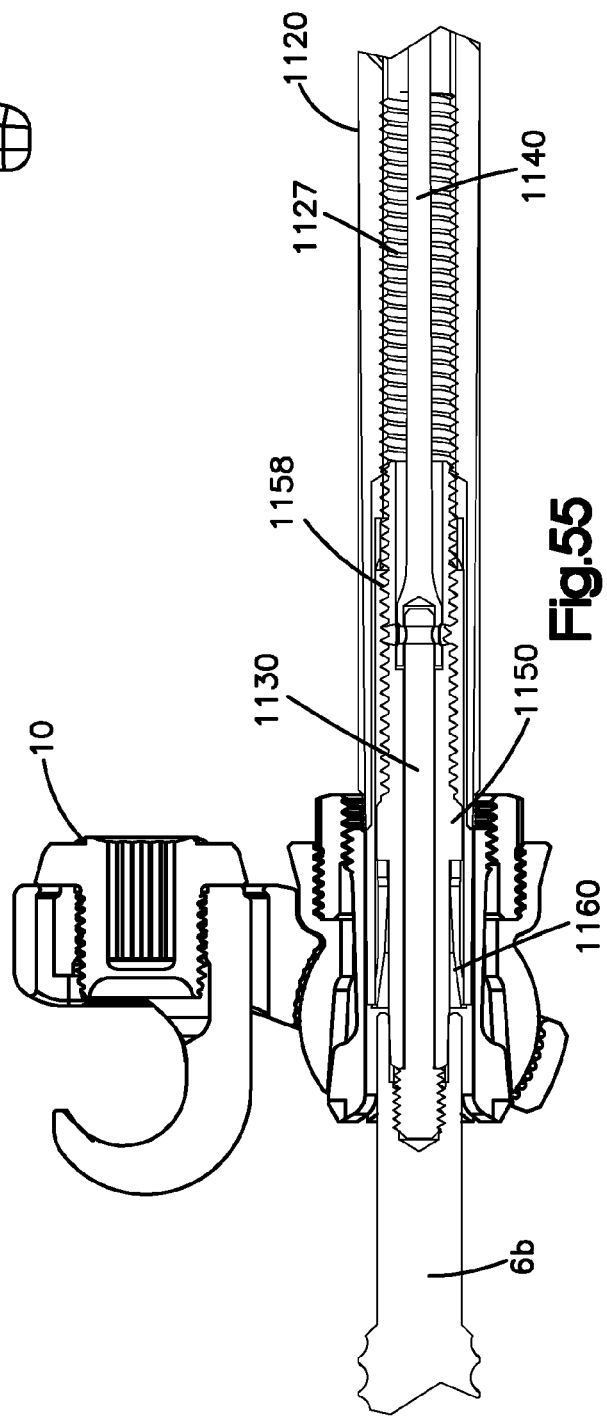

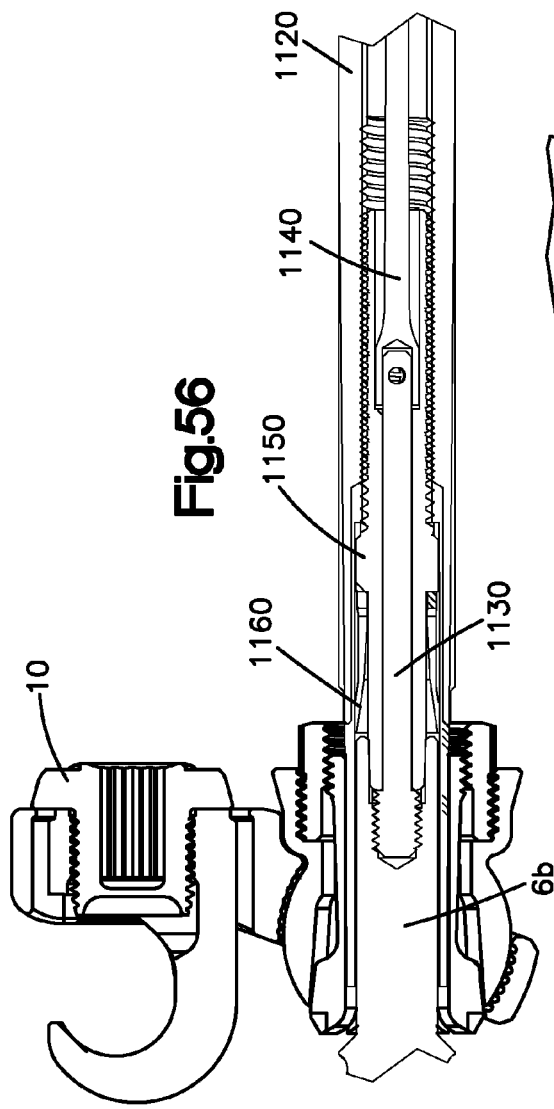
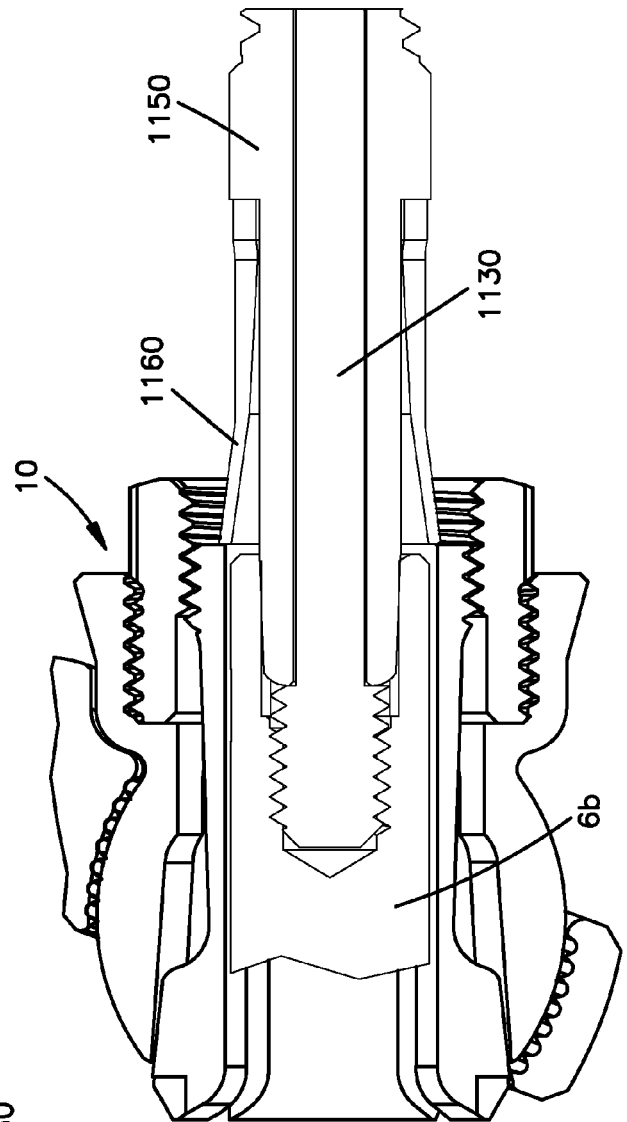
Fig.56
Fig.57

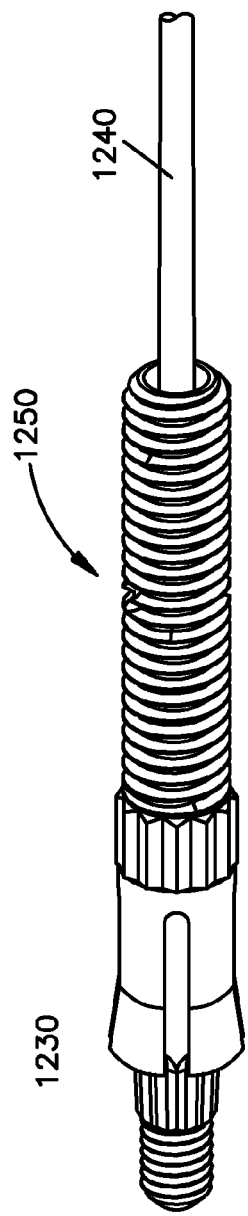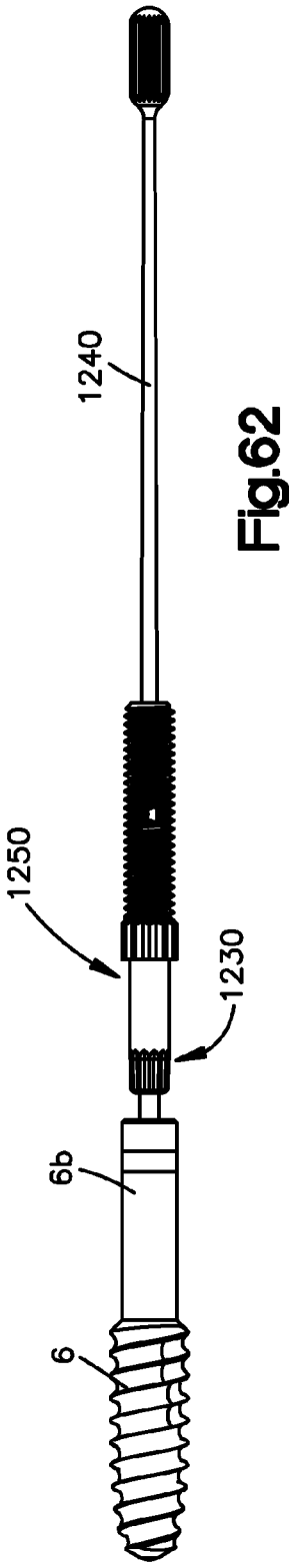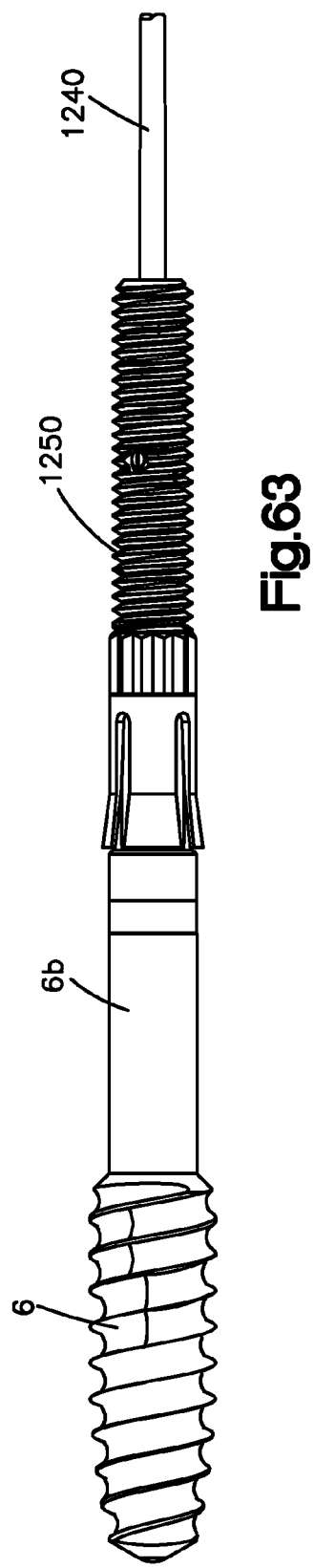

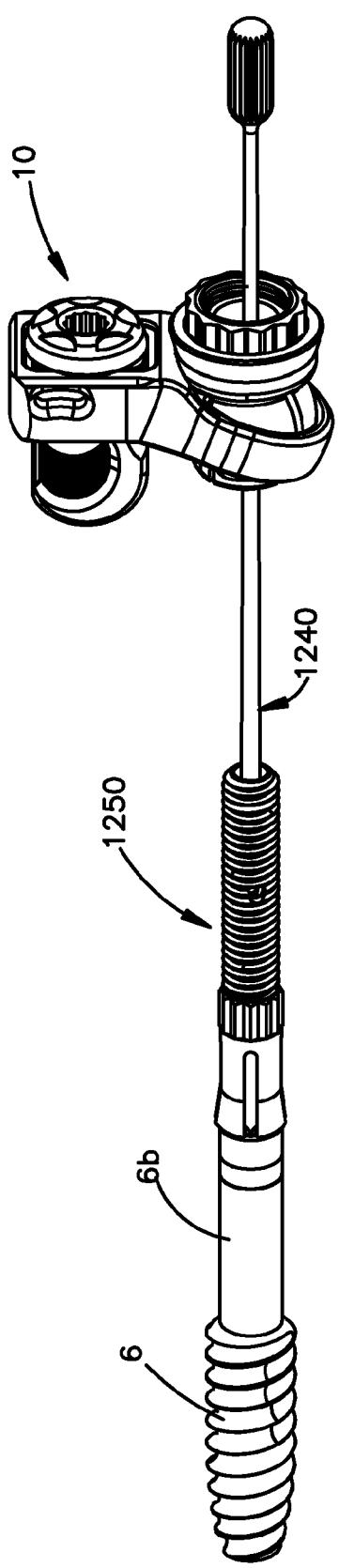
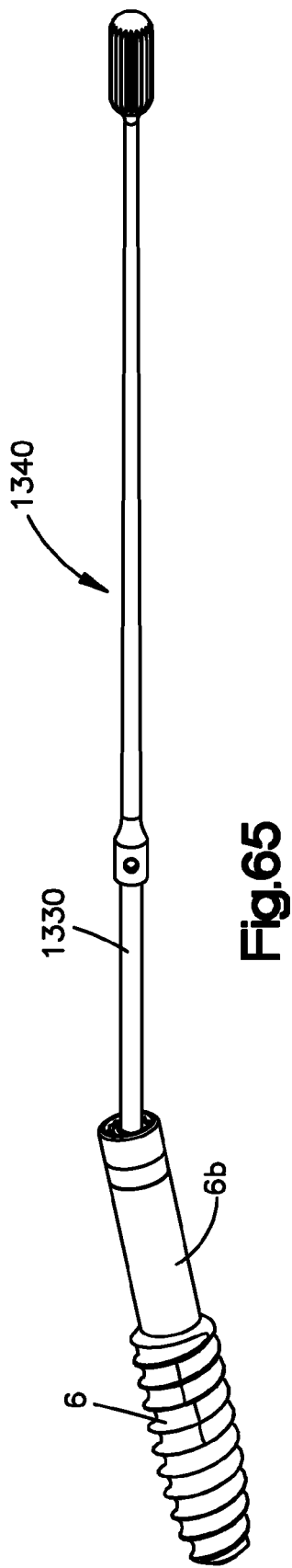
Fig.64
Fig.65

CLAMPS USED FOR INTERCONNECTING A BONE ANCHOR TO A ROD

CROSS REFERENCE TO RELATED APPLICATIONS

This application claims priority to U.S. provisional patent application Ser. No. 60/950,809, filed Jul. 19, 2007 and is a continuation-in-part of International patent application serial No. PCT/US2007/074633, filed Jul. 27, 2007. The content of these applications is hereby incorporated by reference in their entirety.

FIELD OF THE INVENTION

The present invention relates to a clamp, and, more particularly, to a clamp for securing the position of a bone anchor with respect to a longitudinal rod, preferably for use in the spine.

BACKGROUND OF THE INVENTION

Spinal fusion is a procedure that involves joining two or more adjacent vertebrae with a bone fixation device to restrict movement of the vertebra with respect to one another. Spinal fixation devices are used in spine surgery to align, stabilize and/or fix a desired relationship between adjacent vertebral bodies. Such devices typically include a spinal fixation element, such as, for example, a relatively rigid fixation rod, a dynamic or flexible spinal rod, etc. (collectively referred to herein as a longitudinal rod), that is coupled to adjacent vertebrae by attaching the spinal fixation element to various bone fixation elements, such as, for example, hooks, bolts, wires, screws, etc. (collectively referred to herein as a bone anchor). The bone anchor may commonly include heads with channels in which the longitudinal rod is inserted and subsequently clamped by a set screw or closure cap. Surgeons may commonly choose to install multiple bone anchors, as well as multiple longitudinal rods, to treat a given spinal disorder. The longitudinal rods may have a predetermined contour, and once installed, the longitudinal rod may hold the vertebrae in a desired spatial relationship, either until desired healing or spinal fusion has taken place, or for some longer period of time.

Surgeons have often encountered difficulty installing such devices because of trouble aligning the longitudinal rod(s) with the channels in the heads of the bone anchors. For example, the heads of bone anchors may often be out of vertical and/or horizontal alignment with one another because of the curvature of the spine or the size and shape of each vertebra.

The process of positioning and setting known bone anchors may be tedious and relatively time-consuming, typically requiring more than one surgical tool to clamp the longitudinal rods and the bone anchors in desired positions. Even with a high degree of skill and care, the process of positioning an assembly of known bone anchors and longitudinal rods, and clamping said bone anchors and longitudinal rods in place can take more time than desired during a surgical procedure, and may even result in longitudinal rods, bone anchors, or both moving out of position before clamping is completed.

Thus, it is desirable to have a spinal fixation device (also referred to herein as a clamp) that can secure longitudinal rods and bone anchors in place with a minimal amount of time and a minimal number of surgical tools. It is also desirable to have a clamp that can secure a longitudinal rod at an axis that is offset or laterally displaced from the axis of the bone anchor.

SUMMARY OF THE INVENTION

The present invention relates to a clamp, and, more particularly, to a clamp for securing the position of a bone anchor with respect to a longitudinal rod in a posterior spinal fixation procedure. The clamp may include a housing, a rod clamping assembly, and a bone anchor clamping assembly. The clamp preferably enables the longitudinal axis of the rod to be offset or laterally displaced from the longitudinal axis of the bone anchor. The rod clamping assembly may be moveably associated, preferably slidably coupled, to the housing so that the rod clamping assembly may be moveable to provide increased flexibility to better accommodate the longitudinal rod or to better accommodate vertebrae positioning, and the bone anchor clamping assembly may be moveably associated, preferably pivotably coupled, to the housing so that the bone anchor clamping assembly can be moveable to provide increased flexibility to better accommodate the bone anchor. Alternatively and/or in addition, the bone anchor clamping assembly may be moveably associated, preferably slidably coupled, to the housing.

In one exemplary embodiment, the bone anchor may include a bone engaging portion and an extending portion. The clamp for securing the bone anchor with respect to a rod may include a housing having a first elongated opening sized and configured to receive at least a portion of the bone anchor, a second opening associated with the rod, and one or more slits in communication with the second opening, the slit dividing the housing into a first portion and a second portion so that the housing is elastically deflectable. The bone anchor clamping assembly may include a rotatable member; a slider member including a top surface, a bottom surface, and a bore extending from the top surface to the bottom surface, the slider member positioned between the rotatable member and the housing, the slider member translatable with respect to the housing; and a collet positioned at least partially within the first opening, the collet including a top portion, a bottom portion and a bore extending from the top portion to the bottom portion, the bore receiving at least a portion of the extending portion of the bone anchor, the bore including one or more threads for engaging the rotatable member, at least a portion of the collet extending through the bore of the slider member so that movement of the slider member with respect to the housing causes the collet and the bone anchor to move at least with respect to the housing. Preferably, the rod clamping assembly and the bone anchor clamping assembly are laterally spaced apart with respect to one another and are sized and configured so that rotation of the rotatable member fixes the position of the rod with respect to the housing and the position of the bone anchor with respect to the housing.

In use, rotation of the rotatable member to a locked position may cause a downward force onto the slider member, which in turn may cause the slider member to contact the housing and may cause the collet to move with respect to the housing, which in turn may cause the position of the slider member and the position of the bone anchor to be fixed with respect to the housing. In addition, rotation of the rotatable member to the locked position may cause the first and second portions of the housing to move with respect to one another which in turn may cause the slit formed in the housing to compress, thereby causing a diameter of the second opening formed in the housing to decrease so that the housing tightens around the rod thus fixing the position of the rod with respect to the housing.

The collet may include one or more slots extending upwards from the bottom portion of the collet, thereby defining one or more deflectable collet fingers. Preferably, the collet includes two slots and two collet fingers. The bottom portion of the collet may include a substantially curved outer surface for contacting a substantially corresponding internally curved surface formed in the first opening. The bore of the collet may be internally threaded so that the bone anchor can be threaded through the bore formed in the collet.

The slider member may be in the form of a plate-type member. In use, movement of the slider member generally parallel to a top surface of the housing may cause the bone anchor to angulate with respect to the housing.

The housing may include one or more upwardly projecting surfaces, preferably curved surfaces, extending from a top surface of the housing adjacent to the first opening.

The bone anchor clamping assembly may include a bushing, the bushing being polyaxially rotatable with respect to the housing.

In another exemplary embodiment, the bone anchor may include a bone engaging portion, an extending portion and an anchor axis, the bone engaging portion being sized and configured to be positioned at least partially within a bone. The clamp for securing the bone anchor to a rod may include a housing having a first opening and a second opening, the first opening being laterally spaced from the second opening, a bone anchor clamping assembly and a rod clamping assembly. The bone anchor clamping assembly may include a bore extending therethrough. The bone anchor clamping assembly is preferably positioned at least partially within the first opening formed in the housing and the extending portion of the bone anchor is preferably positioned at least partially within the bore of the bone anchor clamping assembly. The bone anchor is preferably polyaxially rotatable relative to the housing and the housing is preferably movable generally parallel to the anchor axis in an unlocked configuration. The bone anchor clamping assembly is preferably sized and configured to lock an angular orientation of the bone anchor relative to the housing and the position of the housing relative to the vertebra in a locked configuration. The rod clamping assembly is preferably positioned at least partially within the second opening. The rod clamping assembly is preferably sized and configured to engage the rod and is preferably movable within the second opening laterally relative to the first hole in a slack configuration, the rod clamping assembly locking the rod relative to the housing in a fastened configuration.

The bone anchor clamping assembly may include a bushing, a collet and a rotatable member. The bushing may include a top portion, a bottom portion, a bore extending from the top portion to the bottom portion and a plurality of slots extending upwards from the bottom portion of the bushing, thereby defining a plurality of deflectable bushing fingers. The collet may include a top portion, a bottom portion, a bore extending from the top portion to the bottom portion, and a plurality of slots extending upwards from the bottom portion, thereby defining a plurality of deflectable collet fingers. The collet is preferably at least partially received in the bore in the bushing. The bottom portion of the bushing may include a substantially spherical outer surface for contacting a substantially corresponding internal surface formed in the housing and defined by the first opening.

The first opening formed in the housing may include at least one protrusion and the bushing may include at least one recess, the at least one protrusion positioned within the at least one recess in the unlocked configuration to prevent rotation of the bushing with respect to the housing.

The bore formed in the bushing may include a narrower diameter portion and the collet may include a flared portion so that movement of the collet with respect to the bushing may cause the flared portion of the collet to contact the deflectable bushing fingers, thereby biasing the bushing fingers outward into contact with the first opening while simultaneously causing the deflectable collet fingers to be biased inwards against the extending portion of the bone anchor.

The bore formed in the collet may include a narrower portion having a smaller size than a size of the extending portion of the bone anchor so that insertion of the bone anchor into the bore formed in the collet causes the extending portion to frictionally couple the bone anchor to the collet.

Preferably, the anchor axis of the bone anchor and the longitudinal axis of the rod are spaced apart so that the anchor axis and the longitudinal axis do not intersect.

The housing may be in the form of a plate having a first portion and a second portion, the first opening being formed in the first portion and the second opening being formed in the second portion, the first portion may be angled with respect to the second portion.

The rod clamping assembly may include a gripping element having a lower portion and an upper portion, the lower portion receiving at least a portion of the rod in the slack and fastened configurations, the upper portion may be operably associated with the housing. Preferably, the upper portion of the gripping element is operably coupled to the housing via a second rotatable member. The upper portion of the gripping element may include a clip for preventing the second rotatable member from entering or exiting through the second opening.

In another exemplary embodiment, the bone anchor may include a bone engaging portion and an extending portion. The clamp for securing the bone anchor with respect to a rod may include a housing having a first opening, at least a portion of the bone anchor being received in the first opening. The housing may be integrally formed at an end of the rod. The bone anchor clamping assembly is preferably disposed at least partially within the first opening, at least a portion of the extending portion of the bone anchor being received within the bone anchor clamping assembly. The bone anchor clamping assembly may include a rotatable member whereby rotation of the rotatable member fixes the position of the bone anchor with respect to the housing.

In another exemplary embodiment, the bone anchor may include a bone engaging portion and an extending portion. The clamp for securing the bone anchor with respect to a rod may include a housing, a rod clamping assembly and a bone anchor clamping assembly. The housing may include a first opening sized and configured to receive at least a portion of the bone anchor, and a second opening sized and configured to receive at least a portion of the rod. The rod clamping assembly may be at least partially disposed within the second opening formed in the housing and may be sized and configured to at least partially contact the rod disposed therein. The bone anchor clamping assembly may be at least partially disposed within the first opening formed in the housing and may be sized and configured to receive at least a portion of the extending portion of the bone anchor. The rod clamping assembly and the bone anchor clamping assembly are preferably laterally spaced apart with respect to one another and the bone anchor clamping assembly may include a rotatable member whereby rotation of the rotatable member fixes the position of the rod with respect to the housing and the position of the bone anchor with respect to the housing.

The housing may also include one or more slits formed therein, the slit being in communication with the second opening, the slit dividing the housing into a first portion and a second portion so that the housing is elastically deflectable.

The bone anchor clamping assembly may include a slider member and a collet, the slider member being sized and configured to reside between the rotatable member and the housing. The collet being sized and configured to partially fit inside the first opening formed in the housing, the collet including a top portion, a bottom portion, a bore extending from the top portion to the bottom portion, the bore being sized and configured to receive at least a portion of the bone anchor, and one or more slots extending upwards from the bottom portion of the collet thereby defining one or more deflectable collet fingers, the collet also including one or more threads for engaging the rotatable member. The bottom portion of the collet may include a substantially curved outer surface for contacting a substantially corresponding internal surface formed in the first opening formed in the housing so that the collet can move with respect to the housing. The collet preferably includes two slots forming two deflectable collet fingers. The bore formed in the collet may include an internal threading, the internal threading being sized and configured to match the threading formed on the bone engaging portion of the bone anchor so that the bone anchor can be threaded through the bore formed in the collet.

The slider member may be in the form of a plate-type member sized and configured to translate with respect to the housing. The slider member may include a top surface, a bottom surface, and a bore extending from the top surface to the bottom surface. The bore formed in the slider member may be sized and configured to receive at least a portion of the collet such that movement of the slider member causes movement of the collet.

The first opening formed in the housing may be in the form of an elongated slot.

The housing may include one or more upwardly projecting ridges or curved surfaces extending from the top surface of the housing adjacent to the first opening. Preferably, the housing includes at least two upwardly protruding ridges or curved surfaces, one on either side of the first opening. The upwardly projecting ridges or curved surfaces being sized and configured to contact the slider member so that movement of the slider member with respect to the housing causes the slider member, and hence the collet and bone anchor located partially therein, to pivot with respect to the housing.

In use, rotation of the rotatable member preferably causes a downward force onto the slider member, which in turn causes the slider member to contact the housing and causes the collet to move with respect to the housing, which in turn causes the position of the slider member and the position of the bone anchor to be fixed with respect to the housing. Rotation of the rotatable member preferably also causes the first and second portions of the housing to move with respect to one another which in turn causes the slit formed in the housing to compress thereby causing the second opening formed in the housing to decrease so that the housing tightens around the rod thus fixing the position of the rod with respect to the housing.

In another exemplary embodiment, the bone anchor may include a bone engaging portion and an extending portion. The clamp for securing the bone anchor with respect to a rod may include a housing, a bone anchor clamping assembly and a rod clamping assembly. The housing may include a top surface, a bottom surface, a first opening and a second opening, the first and second openings each extending from the top surface to the bottom surface. The bone anchor clamping assembly may include a bushing, a collet and a rotatable member. The bushing may include a top portion, a bottom portion, a bore extending from the top portion to the bottom portion, a plurality of slots extending upwards from the bottom portion of the bushing thereby defining a plurality of deflectable bushing fingers, and one or more threads. The collet may be sized and configured to be at least partially received in the bore formed in the bushing. The collet may include a top portion, a bottom portion, a bore extending from the top portion to the bottom portion, a plurality of slots extending upwards from the bottom portion thereby defining a plurality of deflectable collet fingers, and one or more threads. The rod clamping assembly may include a gripping element. The gripping element may include a lower portion and an upper portion, the lower portion being sized and configured to receive at least some portion of the rod. The upper portion of the gripping element is preferably operably associated with the housing. The first opening formed in the housing is preferably sized and configured to receive at least a portion of the extending portion of the bone anchor, at least a portion of the bushing, and at least a portion of the collet. The rotatable member may include one or more inner threads and one or more outer threads, the inner threads being sized and configured to engage the threads formed on the collet while the outer threads are sized and configured to engage the threads formed on the bushing so that rotation of the rotatable member causes the collet to move with respect to the bushing, which in turn causes the position of the bone anchor to be fixed with respect to the housing.

The bottom portion of the bushing preferably includes a substantially spherical outer surface for contacting a substantially corresponding internal surface formed in the housing by the first opening so that the bushing can polyaxially angulate with respect to the housing.

The bushing is preferably structured and configured so that it is inhibited from rotating with respect to the housing about a longitudinal axis of the first opening. For example, the first opening may include at least one protrusion and the bushing may include at least one recess, the at least one recess being sized and configured to receive the at least one protrusion to prevent rotation of the bushing with respect to the housing.

The bore formed in the bushing may include a narrower diameter portion and the collet may include a flared portion so that movement of the collet with respect to the bushing causes the flared portion of the collet to contact the deflectable bushing fingers thereby biasing the bushing fingers outward into contact with the first opening while simultaneously causing the deflectable collet fingers to be biased inwards against the extending portion of the bone anchor.

The bore formed in the collet may include a narrower portion having a smaller size than a size of the extending portion of the bone anchor so that insertion of the bone anchor into the bore formed in the collet causes the extending portion to frictionally couple the bone anchor to the collet.

The second opening formed in the housing may be in the form of an elongated slot so that the position of the gripping element can be adjustable with respect to the housing. Preferably, the gripping element is slidably adjustable with respect to the housing so that the position of the rod is adjustable with respect to the position of the bone anchor. The upper portion of the gripping element preferably is operably coupled to the housing via a second rotatable member. Rotation of the second rotatable member preferably causes the lower portion of the gripping element to wedge the rod against the housing thereby fixing the position of the rod with respect to the housing. The upper portion of the gripping element may include a clip for preventing the rotatable member from passing through the second opening.

The housing may be in the form of a plate having a first portion and a second portion, the first opening being formed in the first portion while the second opening is formed in the second portion, the first portion being angled with respect to the second portion.

BRIEF DESCRIPTION OF THE DRAWINGS

The system is explained in even greater detail in the following exemplary drawings. The drawings are merely exemplary to illustrate the structure of preferred devices and certain features that may be used singularly or in combination with other features. The claims should not be limited to the embodiments shown.

FIG. 1 is a perspective view of an exemplary embodiment of a clamp;

FIG. 2 is a side view of the clamp of FIG. 1;

FIG. 3 is a cross-sectional view of the clamp of FIG. 1 in a first position;

FIG. 4 is cross-sectional view of the clamp of FIG. 1 in a second position;

FIG. 9 is a cross-sectional perspective view of an exemplary embodiment of a bone anchor clamping assembly that may be used in connection with the clamp of FIG. 1;

FIG. 10 is an enlarged cross-sectional view of the bone anchor clamping assembly of FIG. 9;

FIG. 13 is a cross-sectional view of an exemplary embodiment of a bone anchor clamping assembly and a bone anchor that may be used in connection with the clamp of FIG. 1, in a first position;

FIG. 14 is a cross-sectional view of the bone anchor clamping assembly and bone anchor in a second position;

FIG. 15 is a perspective view of an optional exemplary embodiment of an assembly mechanism formed on the bone anchor clamping assembly;

FIG. 16 is a perspective view of an alternate exemplary embodiment of a clamp;

FIG. 17 is another perspective view of the clamp shown in FIG. 16;

FIG. 46 is a perspective view of an optional retention clip which may be used in connection with one of the clamps;

FIG. 47 is a perspective view of an exemplary embodiment of a bone anchor incorporating the retention clip of FIG. 46;

FIG. 48 is an alternate perspective view of the bone anchor of FIG. 47;

FIGS. 51-57 depict various views of an exemplary clamp insertion instrument that may be used for implanting a bone anchor and clamp;

FIGS. 58-64 depict various views of an alternate exemplary clamp insertion instrument that may be used for implanting a clamp; and FIG. 65 depicts an alternate exemplary embodiment of an alternate drive/guide member that may be used in connection with implanting a clamp.

DETAILED DESCRIPTION

Figure 5:
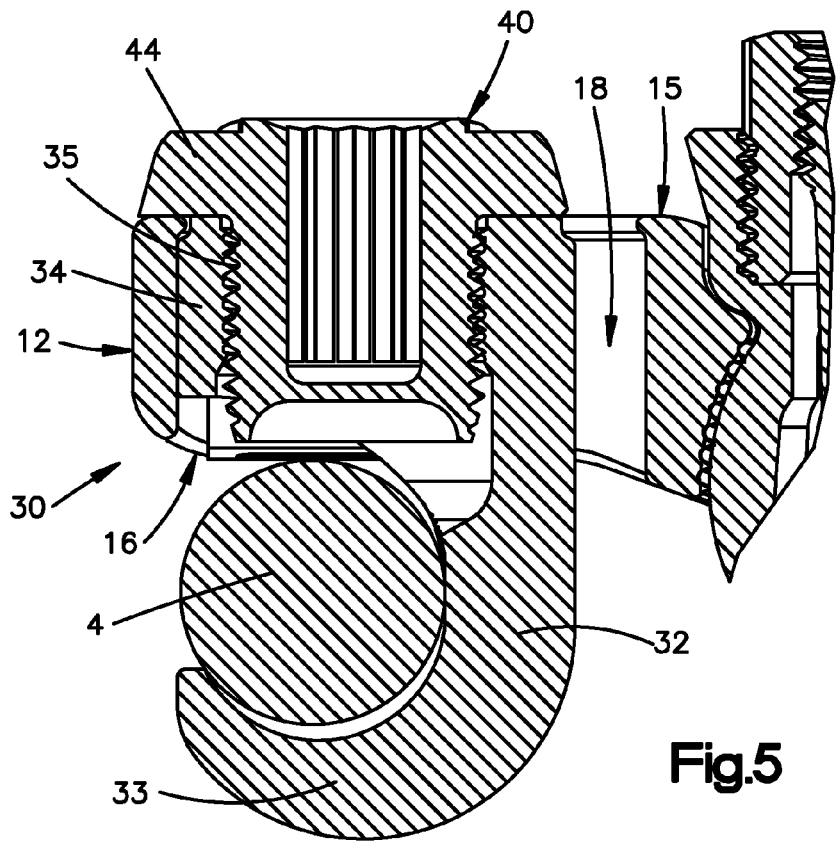
FIG. 5 is a cross-sectional view of an exemplary embodiment of a rod clamping assembly that may be used in connection with the clamp of FIG. 1.

Certain exemplary embodiments will now be described with reference to the drawings. In general, such embodiments relate to a clamp, by way of non-limiting example, a clamp for use in securing a bone anchor, and hence a bone (preferably a vertebra), with respect to a longitudinal rod (preferably a spinal rod). The clamp may include a housing, a rod clamping assembly, and a bone anchor clamping assembly. The clamp preferably enables the longitudinal axis of the rod to be offset or laterally displaced from the longitudinal axis of the bone anchor such that the longitudinal rod may be secured at a position laterally offset or displaced from the bone anchor. The rod clamping assembly may include a first position (e.g., a slack configuration) and a second position (e.g., a fastened configuration) wherein, when in the first position, the rod is moveable with respect to the clamp and, when in the second position, the position of the rod is fixed with respect to the clamp. That is, the rod clamping assembly may be moveably associated, preferably slidably coupled, to the housing so that the rod clamping assembly may be moveable to provide increased flexibility to better accommodate the longitudinal rod or to better accommodate vertebrae positioning. The bone anchor clamping assembly may include a first position (e.g., an unlocked configuration) and a second position (e.g., a locked configuration) wherein, when in the first position, the bone anchor is moveable with respect to the clamp and, when in the second position, the position of the bone anchor is fixed with respect to the clamp. That is, the bone anchor clamping assembly may be moveably associated, preferably pivotably coupled, to the housing so that the bone anchor clamping assembly can be moveable to provide increased flexibility to better accommodate the bone anchor. That is, the longitudinal axis of the bone anchor may be spaced apart from the longitudinal axis of the rod by a distance X. More preferably, the distance X is adjustable. Preferably, the distance X may be adjustable from about 7.0 mm to about 40 mm, more preferably about 10 mm to about 25 mm. However, other ranges are contemplated.

The invention may have other applications and uses and should not be limited to the structure or use described and illustrated. That is, while the clamp will be described as and may generally be used in the spine (for example, in the lumbar, thoracic or cervical regions), those skilled in the art will appreciate that the clamp may also be used for fixation of other parts of the body such as, for example, joints, long bones or bones in the hand, face, feet, maxiofacial region, mandible, etc. In addition, the clamp may be used in the external fixation of the body such as, for example, where rods are joined outside of the patient's body along, for example, the patient's long bones, spine, etc. The clamp may also be used to connect proximal or distal extensions to a rib hook in an expandable prosthetic rib, as a clamping assembly/mechanism for a transconnector (e.g., a device that connects two rods with one another during spinal surgery), to connect and secure the pieces of a retractor system, or to attach components, for example, retractor systems to a surgical table. The clamp may be constructed from any biocompatible material known in the art including, but not limited to, stainless steel, titanium, titanium alloys, polymers, etc.

Referring to FIGS. 1-4, the clamp 10 may include a housing (shown and described as a plate) 12, a rod clamping assembly 30 and a bone anchoring clamping assembly 50 for interconnecting a bone anchor 6, and hence a bone (preferably a vertebra), to a longitudinal rod 4 (preferably a spinal rod).

As generally understood by one of ordinary skill in the art, it should be understood that the longitudinal rod 4 may include, but not be limited to, a solid rod, a non-solid rod, a flexible or dynamic rod, a plate including one or more holes, etc. It should be understood that the clamp 10 is not limited in use to any particular type of longitudinal rod 4.

The bone anchor 6 may include a bone engaging portion 6a, an extending or shaft portion 6b, and a longitudinal anchor axis 6c. As shown, the bone engaging portion 6a may include threads 7 for threadably engaging the targeted vertebra. As generally known by one of ordinary skill in the art, the bone engaging portion 6a may be in other forms, such as, for example, a hook, a pin with or without barbs, a nail, a helical nail, an implant, a wire, etc. It should be understood that the clamp 10 is not limited in use to any particular type of bone anchor 6.

The housing 12 may include a first portion 13 and a second portion 14. As shown, the first portion 13 may be angulated with respect to the second portion 14. The housing 12 may also include a top surface 15, a bottom surface 16, a first throughbore 17 and a second throughbore 18. Although the first throughbore is generally shown and described as having a generally circular shape and the second throughbore is generally shown and described as being an elongated slot, the throughbores may have the same shape and may be in the form of any other shape including, but not limited to, C-shape, hook shape, etc.

The first throughbore 17 may be formed in either the first portion 13 or the second portion 14 (shown here as the first portion 13). The first throughbore 17 is preferably sized and configured to receive at least some portion of the shaft portion 6b of the bone anchor 6. Moreover, the first throughbore 17 may also be sized and configured to receive at least some portion of the bone anchor clamping assembly 50. Preferably, the first throughbore 17 has an internal shape that is sized and configured to substantially match the external shape of the bone anchor clamping assembly 50, more preferably the bushing, as will be described in greater detail below.

The second throughbore 18 preferably is formed in the other of the first portion 13 or the second portion 14 (shown here as the second portion 14). Moreover, the second throughbore 18 may be sized and configured to receive at least some portion of the rod clamping assembly 30, as will be described in greater detail below. Preferably, the second throughbore 18 is in the form of an elongated slot so that the position of the rod clamping assembly 30 can be varied with respect to the housing 12, as will be described in greater detail below.

Figure 6:
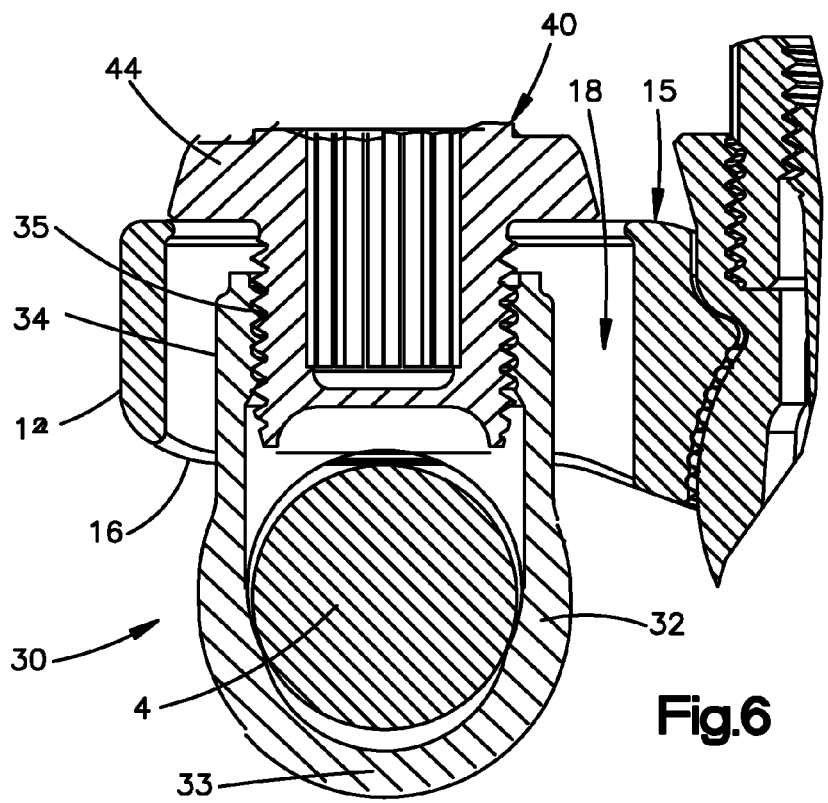
FIG. 6 is a cross-sectional view of an alternative exemplary embodiment of the rod clamping assembly.

As shown in FIGS. 5 and 6, the rod clamping assembly 30 may include a gripping element 32, the gripping element 32 may include a lower portion 33 and an upper portion 34. The upper portion 34 of the gripping element 32 is preferably coupled to the housing 12. More preferably, the upper portion 34 is moveably received within the second throughbore 18, which is preferably in the form of a slot, and coupled to the housing 12 via a nut 40, as will be described in greater detail below, so that the position of the gripping element 32 is moveable with respect to the housing 12 until the nut 40 is tighten. That is, preferably, the rod clamping assembly 30 has a slack or first configuration and a fastened or second configuration wherein, when in the slack or first configuration, the rod clamping assembly 30 is moveably associated with respect to the housing 10, while, when in the fastened or second configuration, the position of the rod clamping assembly 30 is fixed with respect to the housing 10.

The lower portion 33 is preferably sized and configured to receive at least some portion of the longitudinal rod 4, and may be shaped as a hook, loop, or any other shape. Preferably, the gripping elements 32 are sized and configured to be interchangeable with the clamp 10 so that, for example, the user can select between the hook shaped gripping element (shown in FIG. 5) and the loop shaped gripping element (shown in FIG. 6) as required. It should be understood however that the clamp 10 should not be limited by the shape of the gripping element 32.

The lower portion 33 of the gripping element 32 is preferably designed to extend below the bottom surface 16 of the housing 12 so that the longitudinal rod 4 may be received between the gripping element 32 and the housing 12. As shown, the upper portion 34 of the gripping element 32 may include an engagement portion 35. As shown, the engagement portion 35 preferably includes one or more threads for threadably engaging the nut 40. As shown, the engagement portion 35 may include an internally threaded portion sized and configured to engage a threaded outer portion formed on the nut 40.

The nut 40 may also include a rim 44, at least a portion of the rim 44 preferably being sized and configured to be larger than the second throughbore 18 so that the rim 44 acts as a stop to prevent the nut 40 from passing completely through the second throughbore 18. Moreover, the nut 40 may also include a notch (not shown), the notch being sized and configured to receive a clip (not shown). Preferably, the clip is sized and configured to prevent the nut 40 from passing through the second throughbore 18 via the upper surface 15 of the housing 12. Thus, preferably, once assembled, the nut 40 and the gripping element 32, which is threadably engaged thereto, is prevented via the rim 44 and the clip from becoming disassembled from the housing 12. Alternatively, any other mechanism known in the art for preventing the nut 40 and gripping element 32 from becoming disassembled from the housing 12 may be used including, but not limited to, dowel pins, splaying, welding, thread staking, etc.

In use, rotation of the nut 40 causes the rod clamping assembly 30 to move from the slack or first configuration to the fastened or second configuration. That is, in use, rotation of the nut 40 causes the nut 40 to engage the gripping element 32, which in turn causes the lower portion 33 of the gripping element 32, and hence the longitudinal rod 4, to move upwards until the rod 4 contacts the housing 12. At this point, the longitudinal rod 4 is wedged between the bottom surface 16 of the housing 12 and the gripping element 32 thereby fixing the position of the rod 4 with respect to the housing 12. In addition, rotation of the nut 40 causes the housing 12 to be wedged between the gripping element 32 and the nut 40 thereby fixing the position of the gripping element 32 with respect to the housing 12.

Figure 7:
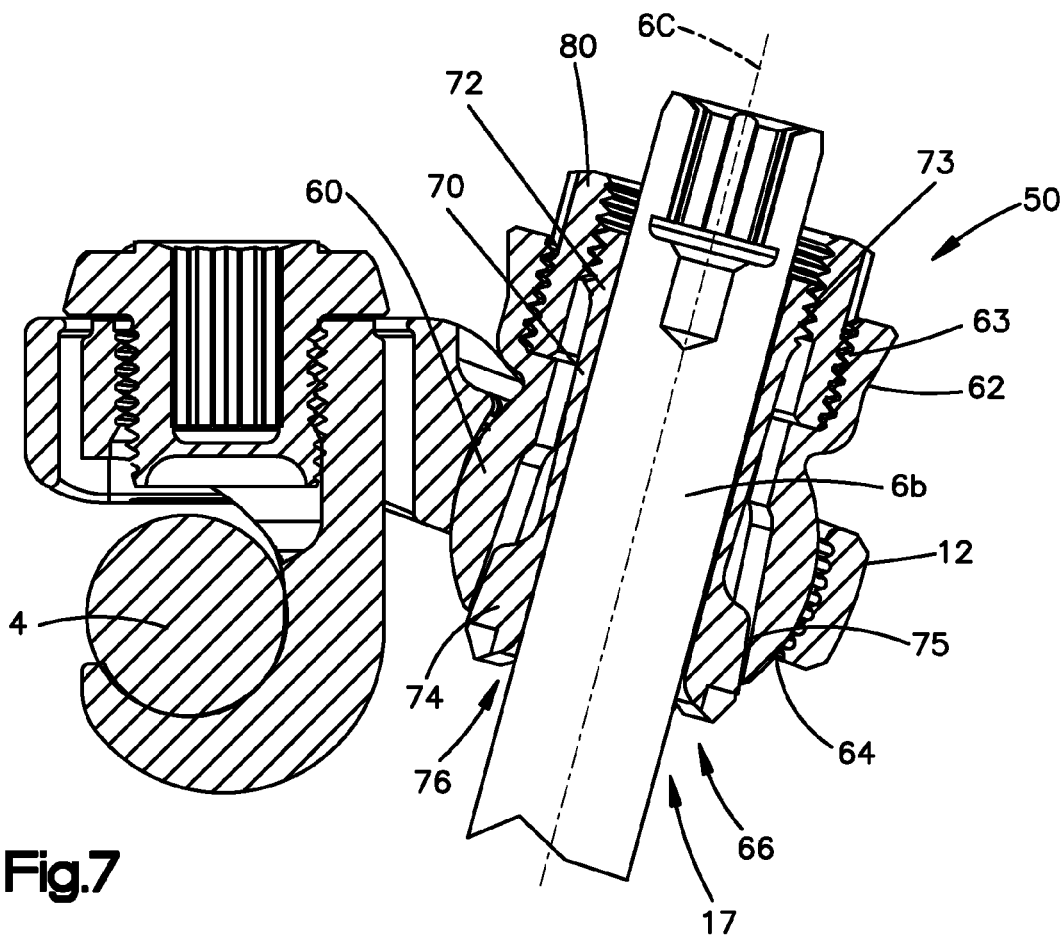
FIG. 7 is an alternate side view of the clamp shown in FIG. 1.

As best shown in FIG. 7, the bone anchor clamping assembly 50 may include a bushing 60, a collet 70 and a nut 80 wherein the bushing 60 is preferably sized and configured to be at least partially received within the first throughbore 17 formed in the housing 12, and the collet 70 is preferably sized and configured to be at least partially received in the bore 66 of the bushing 60 and to partially receive at least some portion of the shaft portion 6b of the bone anchor 6, as will be described in greater detail below.

The collet 70 may include a top portion 72, a bottom portion 74, and a bore 76 extending from the top portion 72 to the bottom portion 74. Preferably, the top portion 72 includes one or more threads 73 for engaging the nut 80, as will be discussed in greater detail below. Preferably, the bottom portion 74 includes an enlarged portion 75 such as, for example, a flared end portion. The collet 70 preferably also includes one or more longitudinal slots 78 (as best shown in FIG. 10) extending upwards from the bottom portion 74, thereby creating a plurality of deflectable fingers 79.

Additionally, the bore 76 formed in the collet 70 may include a narrower diameter portion (e.g., a shoulder, a tapered portion, etc.) (not shown). The narrower diameter portion may be located anywhere along the length of the bore 76. The narrower diameter portion may have an internal diameter smaller than the outer diameter of the shaft portion 6b of the bone anchor 6 so that insertion of the bone anchor 6 into the bore 76 formed in the collet 70 may cause the shaft portion 6b to frictionally contact the fingers 79 so that the collet 70 is frictionally coupled to the bone anchor 6. Thus, the collet 70 and bone anchor 6 are preferably prevented from becoming accidentally disassembled.

As best shown in FIG. 7, the bushing 60 may include a top portion 62, a bottom portion 64, and a bore 66 extending from the top portion 62 to the bottom portion 64. Preferably, the top portion 62 includes one or more threads 63 for threadably engaging the nut 80, as will be discussed in greater detail below.

The bottom portion 64 of the bushing 60 preferably includes a substantially spherical outer shape. As previously mentioned, the shape of the bottom portion 64 of the bushing 60 is preferably sized and configured to substantially match the shape of the first throughbore 17 formed in the housing 12. Thus, as shown, the spherically outer surface of the bushing 60 preferably facilitates polyaxially angulation of the bushing 60 with respect to the housing 12, which in turn facilitates polyaxial angulation of the bone anchor 6 with respect to the housing 12 so that the longitudinal anchor axis 6c of the bone anchor 6 can be adjusted.

Figure 12:
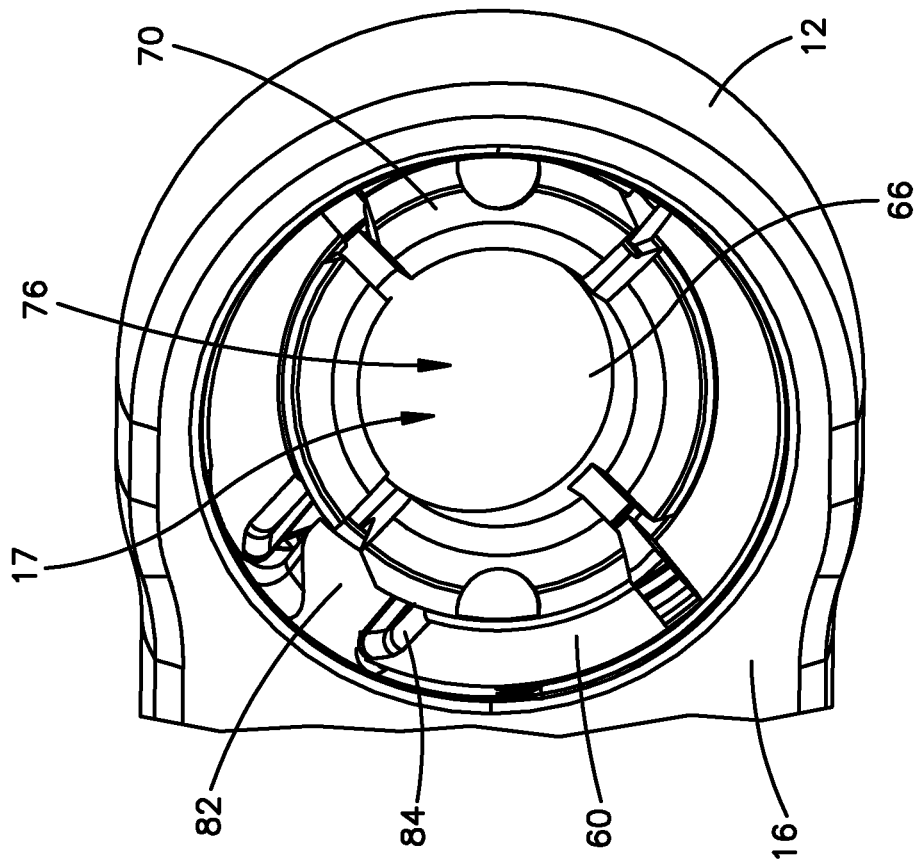
FIG. 12 is a bottom view of an exemplary embodiment of the housing and bone anchor clamping assembly that may be used in connection with the clamp of FIG. 1.
Figure 11:
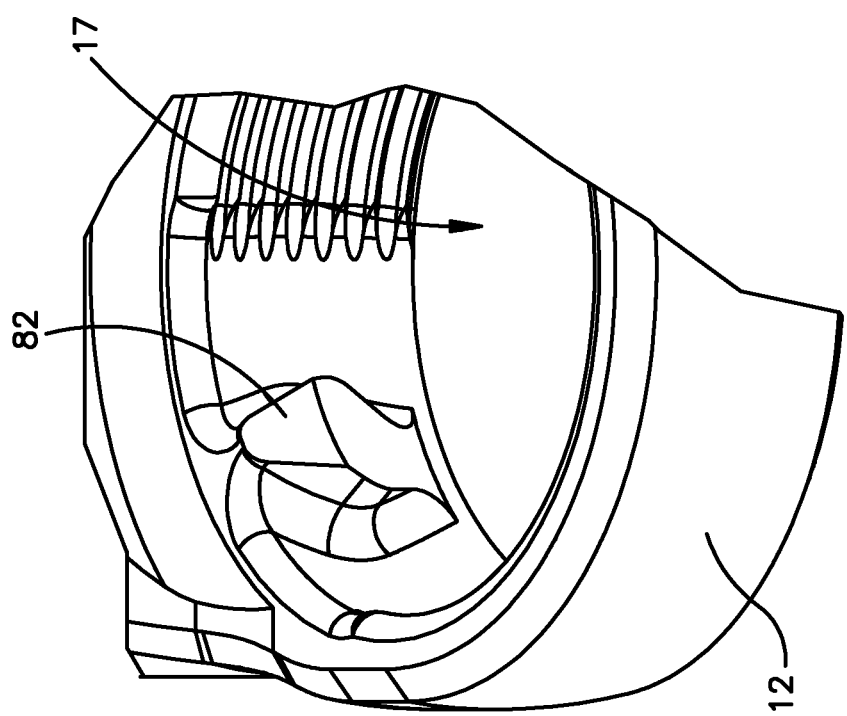
FIG. 11 is a perspective view of an exemplary embodiment of the first throughbore formed in the housing that may be used in connection with the clamp of FIG. 1.

The bushing 60 is preferably sized and configured so that the bushing 60 is capable of polyaxial angulation with respect to the housing 12 without causing the bushing 60 to rotate about an axis parallel to the longitudinal axis of the bone anchor 6. For example, referring to FIGS. 11, 12 and 15, preferably the first throughbore 17 formed in the housing 12 includes one or more protrusions 82 and the bushing 60 includes one or more recesses 84, the recesses 84 being sized and configured to receive the protrusions 82. In this fashion, the bushing 60 is prevented from rotating about an axis parallel to the anchor axis 6c of the bone anchor 6 but is permitted to angulate with respect to the housing 12. Alternatively, the bushing 60 may include one or more projections while the housing 12 includes one or more recesses. Other ways of preventing the bushing 60 from rotating about an axis through its bore 66 are contemplated including, but not limited to, one or more dowel pins or setscrews mating with one or more recesses formed on the bushing.

Figure 8:
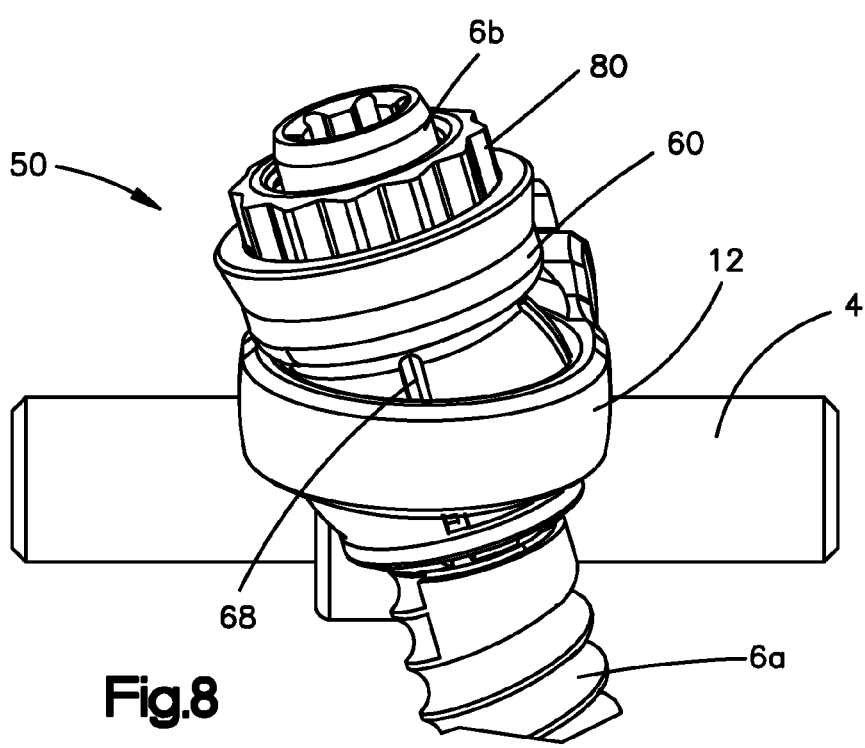
FIG. 8 is a lateral view of the clamp shown in FIG. 1.

Referring to FIGS. 8 and 10, the bushing 60 preferably also includes one or more longitudinal slots 68 extending upwards from the bottom portion 64 of the bushing 60, thereby creating a plurality of deflectable fingers 69. In use, the bore 66 formed in the bushing 60 may also include a narrower diameter portion 67 so that movement of the collet 70 with respect to the bushing 60 causes the enlarged bottom portion 74 of the collet 70 to contact the fingers 69 of the bushing 60 thereby biasing the fingers 69 formed on the bushing 60 outwards while preferably causing the fingers 79 formed on the collet 70 to be biased inwards against the shaft portion 6b of the bone anchor 6.

In use, the bone anchor clamping assembly 50 preferably has an unlocked or first configuration and a locked or second configuration wherein, when in the unlocked or first configuration, the bone anchor 6 is moveably associated with respect to the housing 12, while, when in the locked or second configuration, the position of the bone anchor 6 is fixed with respect to the housing 12. Preferably, when in the unlocked or first configuration, the bone anchor 6 is capable of polyaxially rotating with respect to the housing 12 and/or the housing 12 is capable of moving along the axis of the bone anchor 6 (e.g. the housing 12 can move generally parallel to the anchor axis 6c) so that the distance between the housing 12 and the bone can be adjusted.

Referring to FIGS. 13 and 14, the nut 80 preferably includes a set of inner threads 81a and a set of outer threads 81b. The inner threads 81a formed on the nut 80 being sized and configured to engage the threads 73 formed on the collet 70 while the outer threads 81b formed on the nut 80 are sized and configured to engage the threads 63 formed on the bushing 60. In use, rotation of the nut 80 preferably causes the bone anchor clamping assembly 50 to move from the unlocked configuration to the locked configuration. That is, in use, rotation of the nut 80 preferably causes the collet 70 to move with respect to the bushing 60. Consequently, rotation of the nut 80 causes the enlarged bottom portion 75 of the collet 70 (as shown in FIG. 10) to become biased against both the shaft portion 6b of the bone anchor 6 and the deflectable fingers 69 of the bushing 60, which in turn causes the position of the bone anchor 6 to be fixed with respect to the collet 70 and the position of the collet 70 to be fixed with respect to the bushing 60. In addition, rotation of the nut 80 causes the fingers 69 formed on the bushing 60 to be biased against the first throughbore 17 formed in the housing 12 which in turn causes the position of the bushing 60, and hence the position of the collet 70 and bone anchor 6, to be fixed with respect to the housing 12.

Referring to FIG. 15, the collet 70 may also include one or more cutouts 85 formed in one or more of the fingers 79, the cutouts 85 being sized and configured to engage the tips formed on an insertion instrument so that the fingers 79 can be squeezed together and rotated thus facilitating insertion and removal of the collet 70 from the bushing 12.

In use, the clamp 10 preferably enables the position of the rod clamping assembly 30 to be moveably coupled, and more preferably slidably adjustable, with respect to the housing 12, and hence with respect to the bone anchor 6 secured thereto. Slidable adjustment of the rod clamping assembly 30 enables the position of the longitudinal rod 4 to be adjustable with respect to the position of the bone anchor 6. The position of the rod clamping assembly 30 and hence of the longitudinal rod 4 may be fixed with respect to the housing 12 by rotation of the nut 40. In addition, the clamp 10 enables the bone anchor 6 to angulate with respect to the housing 12 via the bone anchor clamping assembly 50. Moreover, the clamp 10 may also enable the position of the housing 12 to be vertically adjustable along the length of the shaft portion 6b of the bone anchor 6, which enables the user to adjust the height of the housing 12 with respect bone anchor 6. The position of the bone anchor 6 may be fixed with respect to the housing 12 by rotation of nut 80.

Referring to FIGS. 16 and 17, an alternative exemplary embodiment of a clamp is shown. The clamp 100 may include a housing 110, a rod clamping assembly 130 and a bone anchor clamping assembly 150 for interconnecting a bone anchor 6, and hence a bone, to a longitudinal rod 4 or plate. In this embodiment, the rod clamping assembly 130 may be in the form of an elastically deflectable housing 110, as will be described in greater detail below. The bone anchor clamping assembly 150 may include a collet 160, a slider member 170, and a nut 180.

Figure 18:
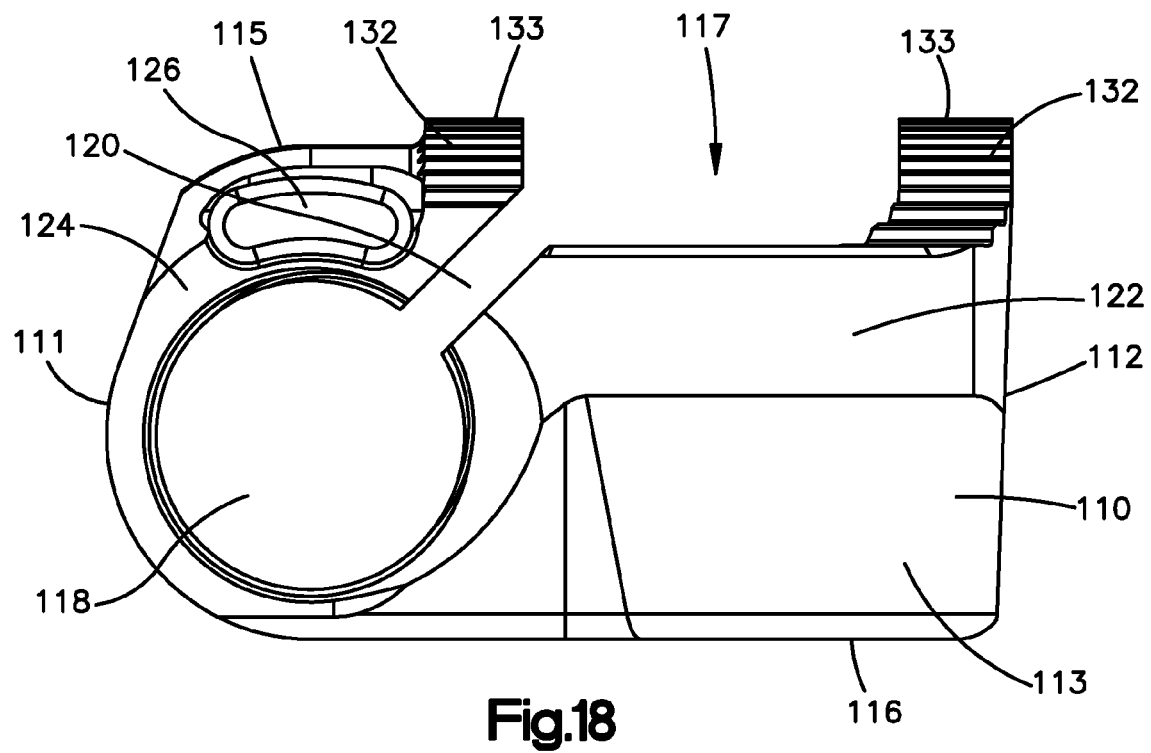
FIG. 18 is a side view of an exemplary embodiment of a housing that may be used in connection with the clamp shown in FIG. 16.
Figure 19:
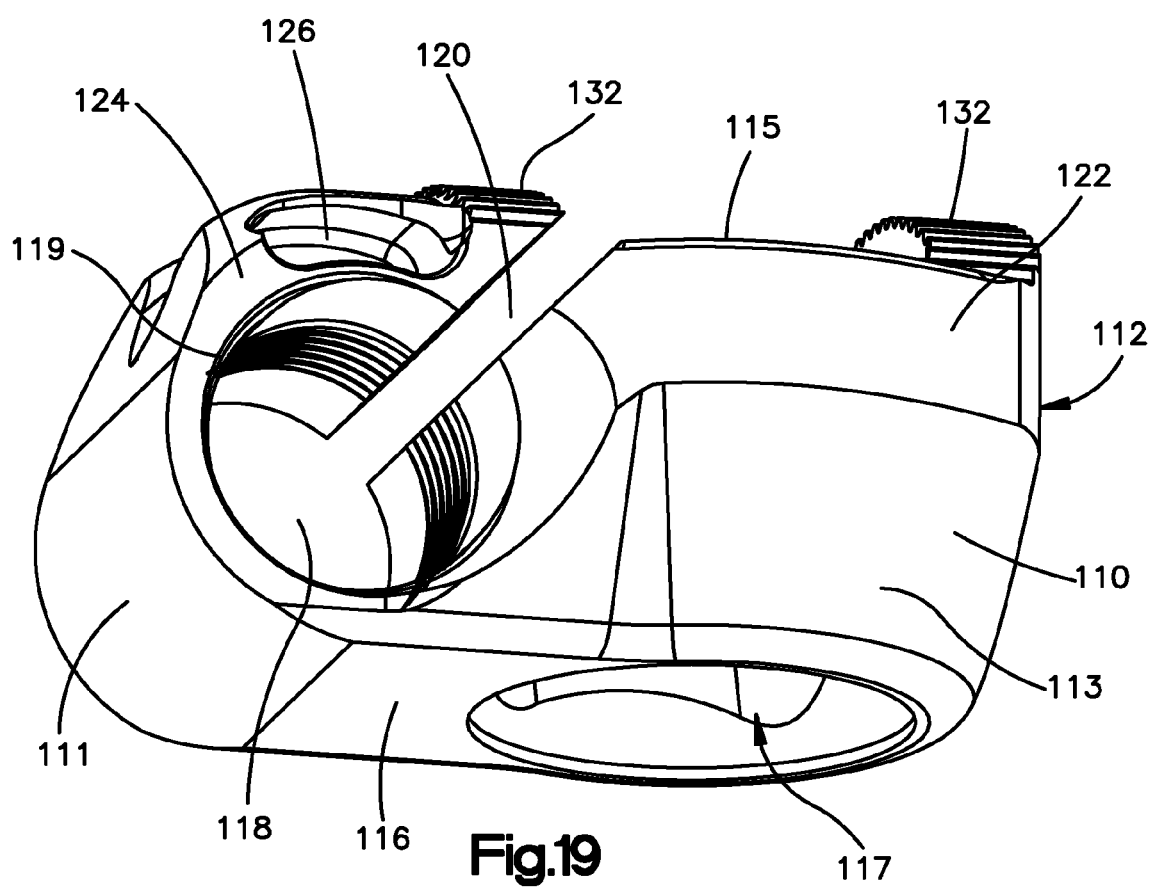
FIG. 19 is a perspective view of the housing shown in FIG. 18.
Figure 20:
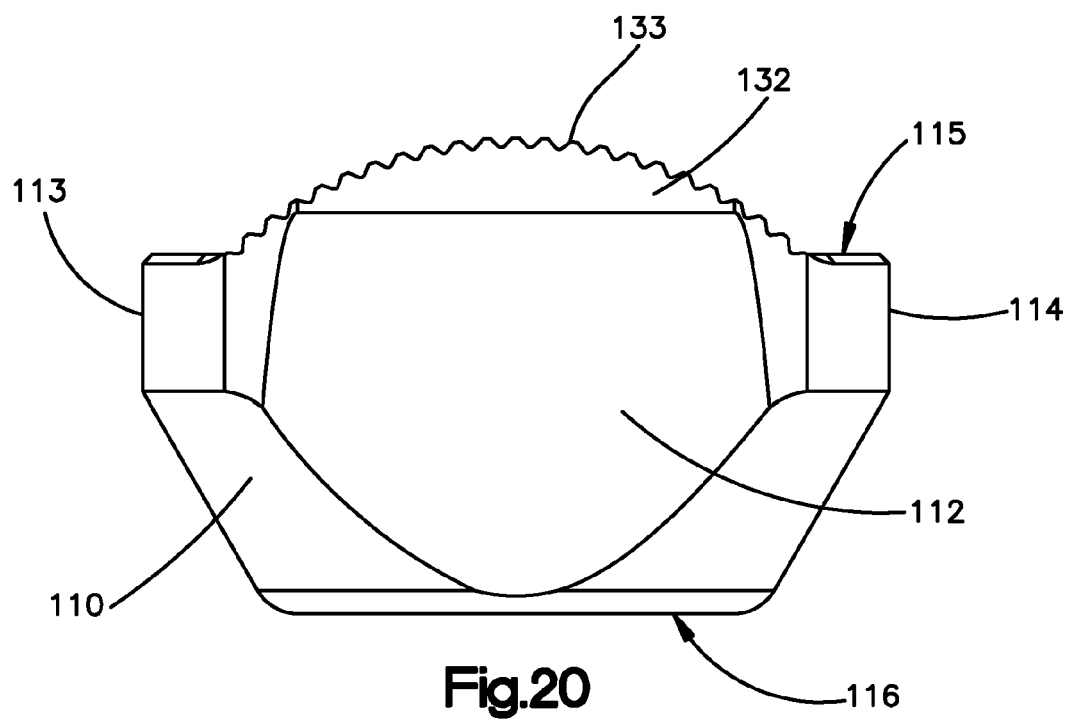
FIG. 20 is a lateral view of the housing shown in FIG. 18.

As best shown in FIGS. 18-20, the housing 110 may include a first side 111, a second side 112, a third side 113, a fourth side 114, a top surface 115 and a bottom surface 116 so that housing 110 may be generally in the form of a rectangular body. However, those skilled in the art will recognize that the housing 110 may be in the form of any number of shapes including, but not limited to, square, ellipsoid, spherical, etc. It should be understood the clamp 100 is not to be limited by the shape of the housing 110.

The housing 110 may also include a first throughbore 117 and a second throughbore 118. The second throughbore 118 may be sized and configured to receive at least some portion of the longitudinal rod 4. The axis of the first throughbore 117 is preferably perpendicular to the axis of the second throughbore 118 although other angles are contemplated. The second throughbore 118 may include a plurality of serrations 119 for contacting the outer surface of the longitudinal rod 4. As will be generally appreciated by one of ordinary skill in the art, incorporation of the serrations 119 increases the frictional contact between the longitudinal rod 4 and the housing 110 thus improving the rod push-through strength. The second throughbore 118 may be any length and any shape, but is preferably sized and configured to match the size and shape of the longitudinal rod 4. The serrations 119 may be any shape, size, depth, etc. The serrations 119 may further be teeth or any other structural element that increases rod push-through strength.

The housing 110 may also include one or more slits 120. As shown, the slit 120 preferably extends from one of the top surface 115, the bottom surface 116, or one of the sides 111, 112, 113, 114 thereof through to and in communication with the second throughbore 118. More preferably, the slit 120 may extend from two or more surfaces or sides of the housing 110 (shown as top surface 115 and sides 113 and 114) so that the housing 110 is divided into a first portion 122 and a second portion 124, the first and second portions 122, 124 being coupled together at one end thereof (shown as first 111). As will generally be appreciated by one of ordinary skill in the art, incorporation of the slit 120 enables the first and second portions 122, 124 of the housing 110 to move or deflect with respect to one another and enables the second throughbore 118 to be elastically deflectable. This, in turn, facilitates easier insertion of the longitudinal rod 4 into the second throughbore 118 and facilitates fixing the position of the rod 4 with respect to the housing 110, as will be described in greater detail below. It should be understood that the slit 120 may be any size and shape. By way of non-limiting example, the slit 120 may be tapered, straight, zigzag, etc. Preferably, the slit 120 is angled with respect to the horizontal plane of the housing 110. More preferably, the slit 120 is angled at an angle of about 45 degrees with respect to the horizontal plane of the housing 110, although other degrees are contemplated. The slit 120 may further incorporate one or more elastic elements such as springs or flexible materials such as rubber, PCU, etc.

The housing 110 may also include one or more recesses 126 for receiving a projection formed on a tool in order to facilitate handling of the clamp 100. It should be noted that the recess 126 may take on any shape necessary for mating with the tool. Alternatively, the housing 110 may include one or more projections for mating with one or more recesses formed on the tool.

As previously mentioned, the housing 110 also preferably includes a first throughbore 117 sized and configured to receive at least a portion of the bone anchor clamping assembly 150, and hence at least a portion of the bone anchor 6, as will be described in greater detail below. The first throughbore 117 preferably extends from the top surface 115 to the bottom surface 116 of the housing 110. The first throughbore 117 preferably is in the form of an elongated slot 117a, at least when viewed from above. The housing 110 may also include one or more upwardly projecting ridges 132 extending from the top surface 115 of the housing 110 adjacent to the first throughbore 117. The ridges 132 preferably include a plurality of serrations 133 formed thereon. Preferably, as shown, the housing 110 includes at least two upwardly protruding ridges 132, one on either side of the first throughbore 117. The ridges 132 preferably incorporate a convex upper surface for reasons that will become apparent below. The radius of curvature for the upwardly protruding ridges 132 may be between about 5 mm and about 15 mm, although any other radius may be used.

It should be understood that the first throughbore 117 may be any size and shape including, but not limited to square, hexagonal, polygonal, oval, etc. It should be further understood that the ridges 132 may project to any extent, if at all, and may have other shapes.

The first throughbore 117 may include top and bottom portions (not shown). The top portion of the first throughbore 117 may have a uniform width. The bottom portion of the first throughbore 117 may have a shape corresponding to the outer shape of the bone anchor clamping assembly 150, and in particular, to the outer shape of the collet 160. For example, the bottom portion of the first throughbore 117 may have a bell-shaped contour for contacting the corresponding shaped outer surface of the bone anchor clamping assembly 150. The first throughbore 117 may also include a narrower diameter portion (e.g., shoulder, tapered surface, etc.) It should be understood however that first throughbore 117 may have any size and shape including, but not limited to square, cylindrical, conical, etc.

Figures 21, 22:
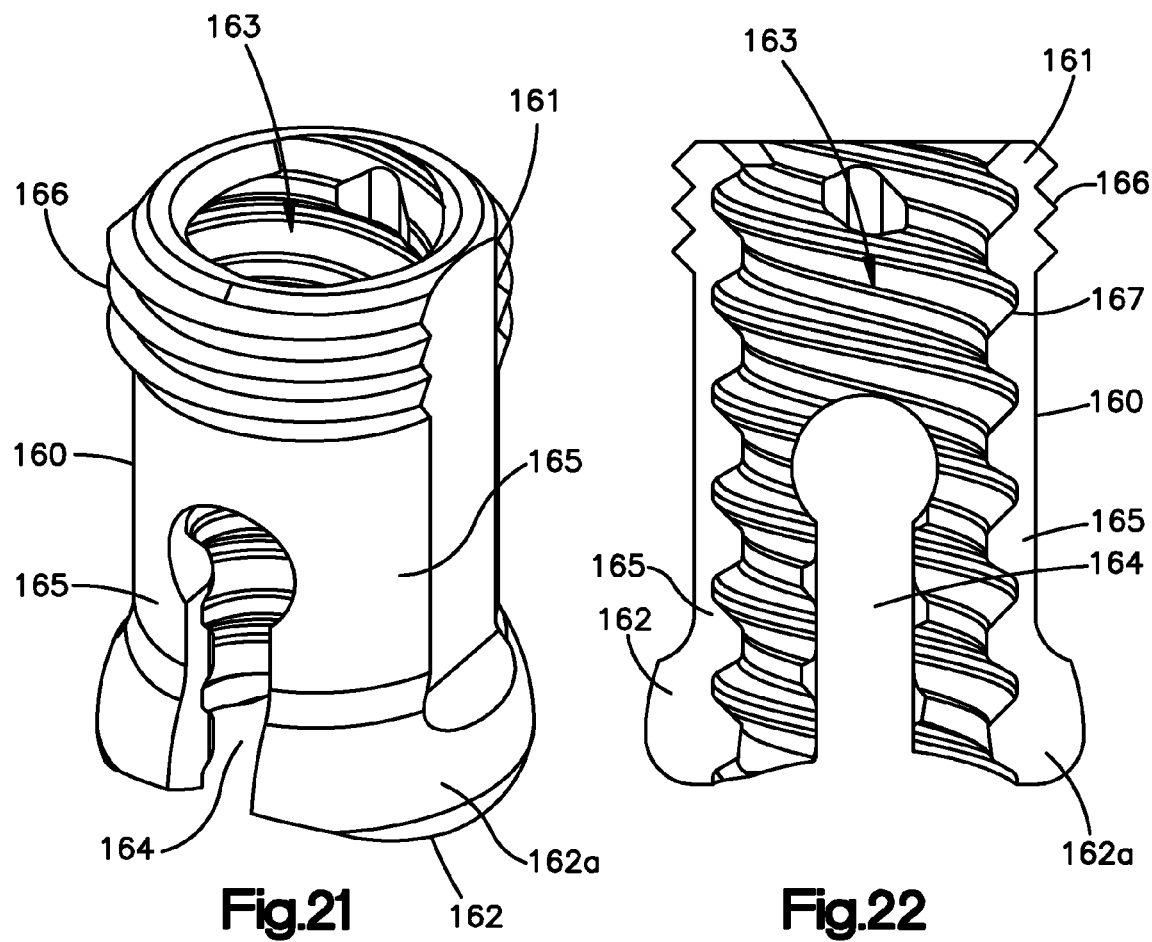
FIG. 21 is a perspective view of an exemplary embodiment of a collet that may be used in connection with the clamp shown in FIG. 16.
FIG. 22 is a cross-sectional view of the collet shown in FIG. 21.

As previously mentioned, the bone anchor clamping assembly 150 may include collet 160, slider member 170, and nut 180. As best shown in FIGS. 21 and 22, the collet 160 may include a top portion 161, a bottom portion 162, and a bore 163 extending from the top portion 161 to the bottom portion 162. In use, the collet 160 is sized and configured to be at least partially received inside of the first throughbore 117 formed in the housing 110. Preferably, the top portion 161 includes one or more threads 166 for engaging the nut 180, as will be discussed in greater detail below. Preferably, the bottom portion 162 includes an enlarged portion 162a such as, for example, a flared end portion or a lip so that at least a portion of the outer diameter of the collet 160 and the flared end portion is greater than at least a portion of the width of the first throughbore 117, preferably the narrower diameter portion. The collet 160 preferably also includes one or more longitudinal slots 164 extending upwards from the bottom portion 162 thereof thereby creating a plurality of deflectable fingers 165. More preferably, the bottom portion 162 of the collet 160 includes two slots 164 so that the collet 160 includes two deflectable fingers 165. Incorporation of two deflectable fingers 165, versus a larger number of deflectable fingers, increases the required torque to failure of the collet 160. Moreover, incorporation of two deflectable fingers 165 produces increased clamping action and minimizes size. It should be understood however that any number of slots 164, and hence deflectable fingers 165, may be used.

As best shown in FIG. 22, the bore 163 formed in the collet 160 may include a threading 167 formed therein. The threading 167 is preferably sized and configured to match the threads 7 formed on the bone engaging portion 6a of the bone anchor 6 so that the bone anchor 6 can be threaded through the bore 163 formed in the collet 160, thus enabling the clamp 100 to be inserted into the body of a patient prior to the implantation of the bone anchor 6.

The collet 160 is preferably long enough to allow at least a portion of the threads 166 formed on the top portion 161 of the collet 160 to extend beyond the opposing ridges 132 formed on the housing 110 while permitting the flared end portion 162a formed on the bottom portion 162 of the collet 160 to contact the first throughbore 117 formed in the housing 110 as the collet 160 is being moved with respect to the housing 110, as will be described in greater detail below. It should be understood however that the clamp 100 should not be limited by the length of the collet 160, and in other embodiments it is envisioned that the top portion 161 of the collet 160 does not extend beyond the top surface 115 of the housing 110, as the nut 180 may be configured, for example, to be inserted into the first throughbore 117 to contact the collet 160.

The collet 160 may be any size or shape including, but is not limited to, cylindrical, cone, parallelepiped, etc. The collet 160 may further include features for mating with a tool such as, for example, flattened areas, depressions, or any other structural element(s).

As previously mentioned, the bone anchor clamping assembly 150 may also include a slider member 170. As best shown in FIG. 17, the slider member 170 may be in the form of a plate 171, the plate 171 being sized and configured to reside between the nut 180 and the housing 110, and more preferably, between the nut 180 and the opposing convex ridges 132 formed on the top surface 115 of the housing 110. The slider member 170 may have a top surface, a bottom surface, and a bore 177 extending from the top surface to the bottom surface. The bottom surface of the slider member 170 preferably includes a plurality of serrations (not shown) for contacting the corresponding serrations 133 formed on the ridges 132 of the housing 110. In use, the slider member 170 is preferably sized and configured to fit on and translate across the ridges 132 of the housing 110. The corresponding serrations formed on the ridges 132 of the housing 112 and the slider member 170 facilitating securement of the slider member 170 with respect to the housing 110, as will be described in greater detail below.

The bore 177 formed in the slider member 170 is preferably sized and configured to receive at least a portion of the collet 160 such that movement and/or translation of the slider member 170 results in movement and/or translation of the collet 160, and hence the bone anchor 6, with respect to the housing 110. Preferably, the ridges 132 formed on the housing 110 include a convex top surface so that movement of the slider member 170 with respect to the housing 110 results in the collet 160 pivoting with respect to the housing 110. The bore 177 is illustrated in the embodiment shown in FIG. 16 and 17, however, it should be appreciated the slider members in other embodiments shown and described herein include similar bores.

It should be understood that the slider member 170 may be any size or shape, including a circle, oval, polygonal, square, etc. Alternatively, in some embodiments, the slider member 170 may be integrally formed with the nut 180.

As previously mentioned, the bone anchor clamping assembly 150 may also incorporate a nut 180. As shown, the nut 180 may include one or more threads for threadably engaging the threads 166 formed on the top portion 161 of the collet 160. The nut 180 may also include one or more tool engaging elements 182 for facilitating engagement with one or more clamp insertion tools. The nut 180 may include any type of tool engaging elements 182 including, but not limited to, a plurality of angled flat surfaces along its perimeter that give the nut 180 a polygonal shape to facilitate rotation of the nut 180. Alternatively, any other structural element, such as a depression or a projection, may be used.

As shown, the nut 180 preferably is disposed around at least a portion of the top portion 161 of the collet 160, above the slider member 170. The perimeter of the nut 180 may be smaller than the perimeter of the slider element 170 such that the edges of the nut 180 do not extend beyond the edges of the slider element 170 to minimize the amount of associated trauma.

In use, the collet 160 may be inserted into the first throughbore 117 formed in the housing 110. The top portion 161 of the collet 160 extending beyond the top surface 115 of the housing 110. Next, the slider member 170 may be placed on top of the housing 110 with the top portion 161 of the collet 160 extending therethrough. Thereafter, the nut 180 may be placed into threaded engagement with the threads 166 formed on the top portion 161 of the collet 160. The nut 180 is preferably screwed down far enough so that the collet 160, the slider member 170, and the nut 180 are coupled to the housing 110, but the user still has the ability to move and/or translate the slider member 170 with respect to the housing 110, thereby enabling the collet 160 to pivot with respect to the housing 110. Thereafter, the subassembly may be implanted as required.

The user may move or translate the slider member 170 along the ridges 132 on the housing 110 so that the collet 160 is moved to a desired angle. Next, the bone anchor 6 may be screwed through the bore 163 formed in the collet 160 and into the patient's bone. Thereafter the longitudinal rod 4 may be inserted through the second throughbore 118 formed in the housing 110. Alternatively, as will be appreciated by one of ordinary skill in the art, the bone anchor 6 may be implanted prior to the subassembly being inserted in-situ. In this embodiment, the collet 160 and subassembly would be slid over the shaft portion 6*b* of the bone anchor 6. Moreover, as will be appreciated by one of ordinary skill in the art, the longitudinal rod 4 may be inserted into the second throughbore 118 formed in the housing 110 prior to the subassembly being implanted in-situ or prior to the subassembly being coupled to the bone anchor 6.

Once the bone anchor 6 has been implanted in the patient's bone, the longitudinal rod 4 has been inserted into the housing 110, and the desired location of the bone anchor 6, longitudinal rod 4 and clamp 100 has been achieved, the position of the rod 4 may be fixed with respect to the position of the bone anchor 6 by rotating the nut 180. That is, rotation of the nut 180 causes the bone anchor clamping assembly 150 to move from the unlocked position to the locked position. More specifically, initial rotation of the nut 180 causes the nut 180 to apply a downward force onto the slider member 170, which in turn causes the serrations formed on the bottom surface of the slider member 170 to contact the serrations 133 formed on the ridges 132 of the housing 110 thereby fixing the position of the slider member 170 with respect to the housing 110. In addition, initial rotation of the nut 180 causes the collet 160 to move with respect to the first throughbore 117 formed in the housing 110 until the collet 160 contacts the inner surface of the first throughbore 117, preferably until the flared end portion 162*a* of collet 160 contacts the narrower diameter portion of the first throughbore 117. This contacts causes the deflectable fingers 165 formed on the collet 160 to move towards one another and causes the collet 160 to be wedged between the bone anchor 6 and the housing 110, which in turn fixes the position of the bone anchor 6 with respect to the housing 110.

Additional rotation of the nut 180 causes the first and second portions 122, 124 of the housing 110 to move with respect to one another which in turn causes the slit 120 formed in the housing 110 to compress. Compression of the slit 120, in turn, causes the second throughbore 118 formed in the housing 110 to collapse or tighten around the longitudinal rod 4, thus fixing the position of the rod 4 with respect to the housing 110. One of the primary benefits of clamp 100 is that the position of the bone anchor 6 is fixed with respect to the housing 110 and the position of the rod 4 is fixed with respect to the housing 110 via rotation of a single element (e.g., nut 180).

It should be understood that the method of use described above is only exemplary and non-limiting, the order of the steps described may be changed, and not every step may be necessary depending on the embodiment of the clamp employed and the procedure being performed.

Figure 23:
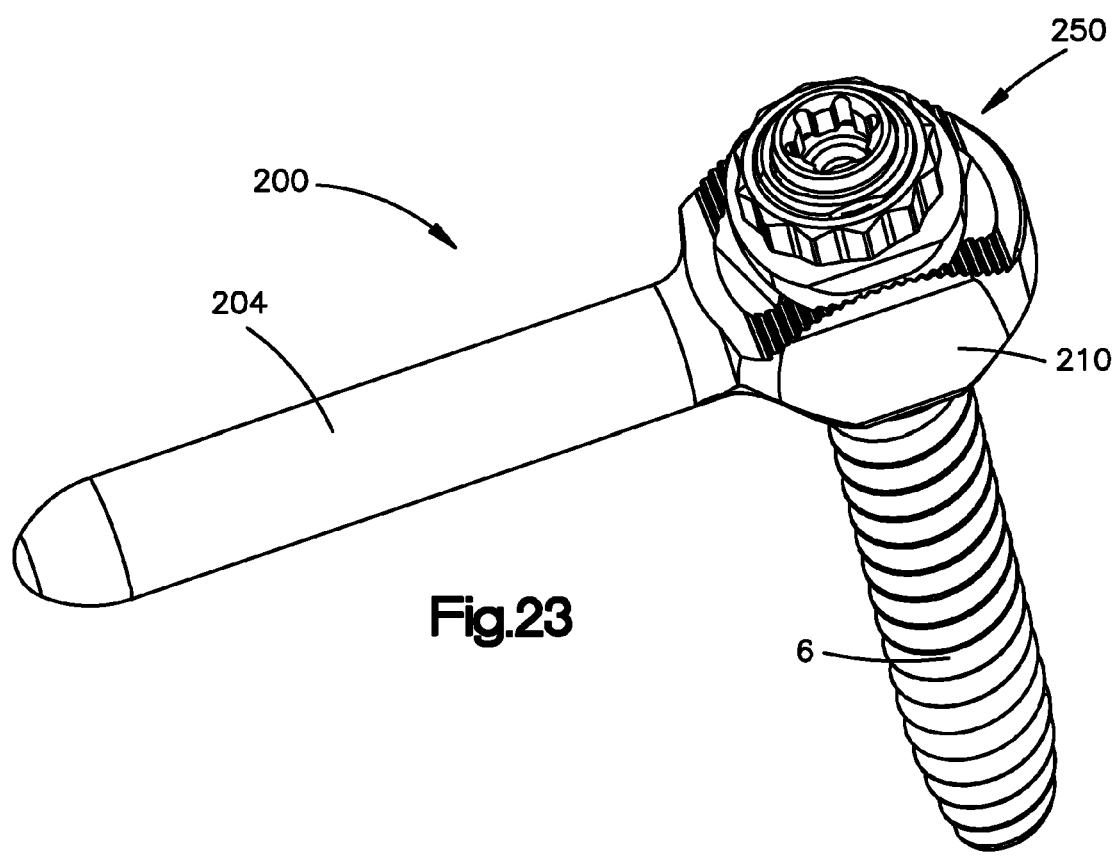
FIG. 23 is a perspective view of alternate exemplary embodiment of a clamp.
Figure 24:
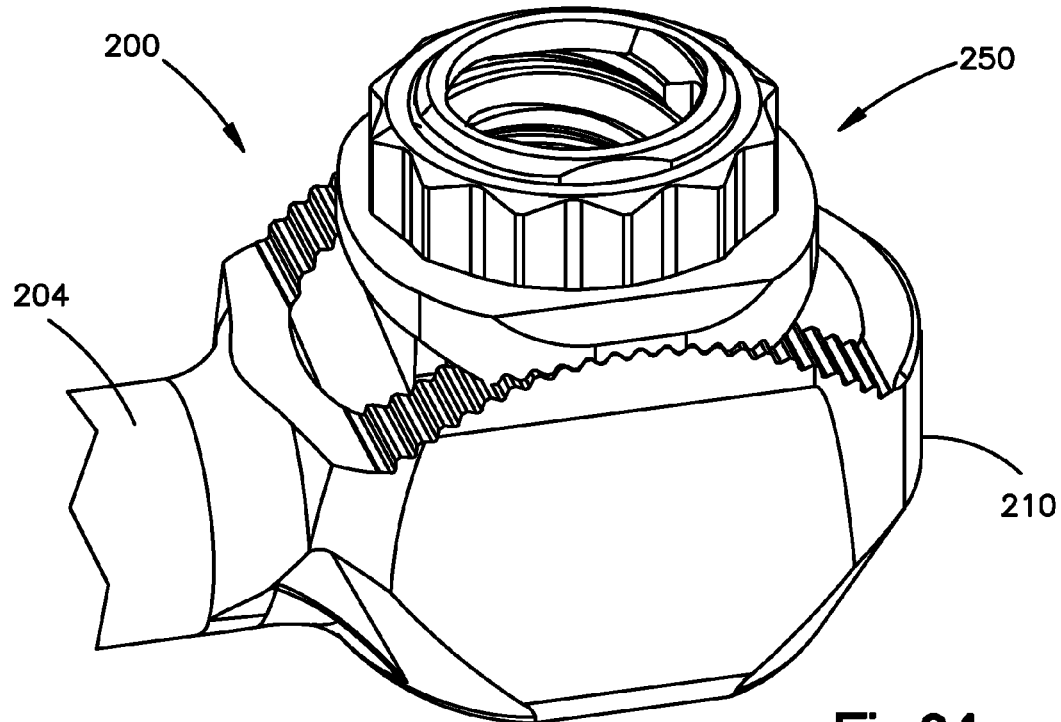
FIG. 24 is another perspective view of the clamp shown in FIG. 23.
Figure 25:
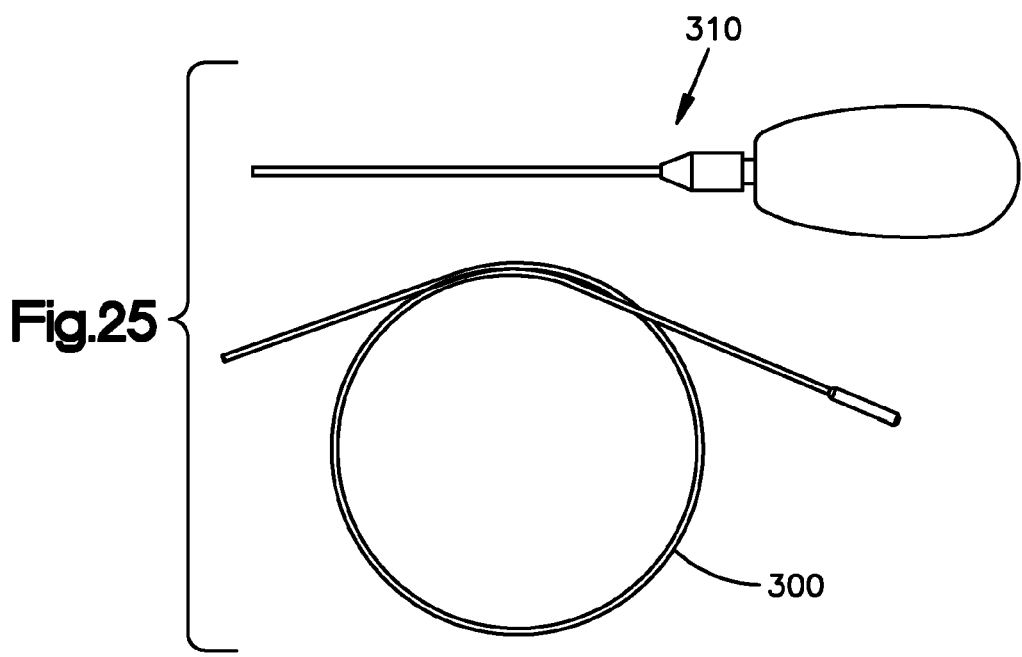
FIG. 25 shows an exemplary embodiment of a flexible guide wire and a guide wire holder which may be used in connection with implantation of a clamp.

Alternatively as shown in FIGS. 23 and 24, an alternate exemplary embodiment of a clamp 200 is shown. In this embodiment, the housing 210 may be modified to include a monolithic and/or integral longitudinal rod 204. The monolithic and/or integral rod 204 may extend from any side of the housing 110, and may be any type of rod and may have any size or shape. It should be noted that the bone anchor clamping assembly in FIGS. 23 and 24 may be substantially the same as the bone anchor clamping assembly 150 described for FIGS. 16-22. The rod may be pre-assembled and/or monolithic with the clamp, or may be assembled during surgery (e.g. screwed into the clamp body).

Figure 26:
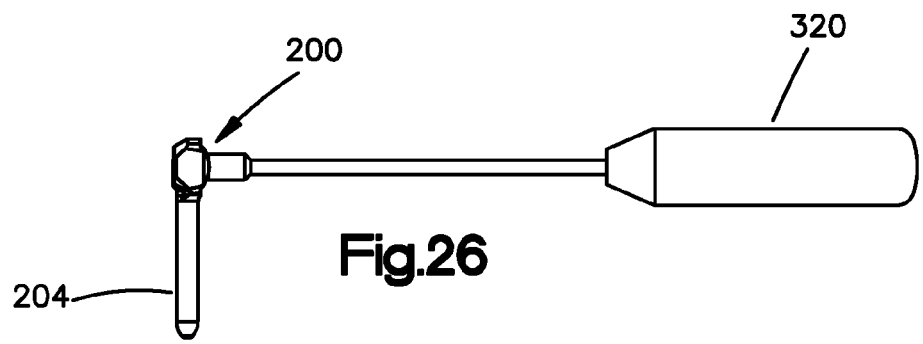
FIG. 26 shows an exemplary embodiment of a clamp insertion instrument which may be used in connection with implantation of a clamp.
Figure 27:
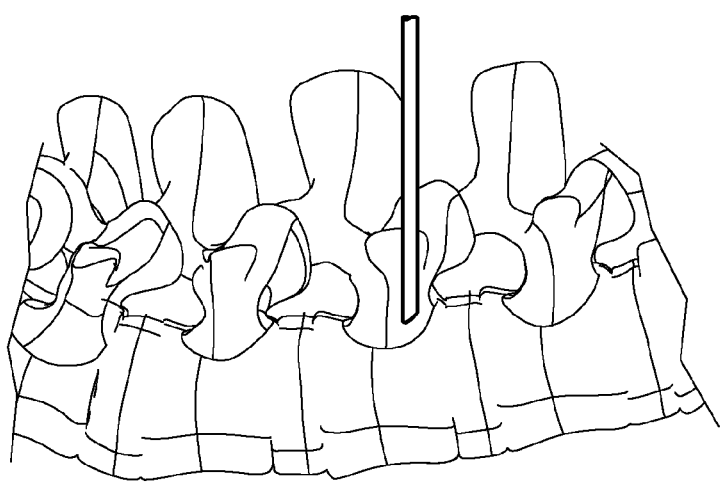
FIGS. 27-35 show an exemplary procedure for implanting a clamp.

An exemplary embodiment of a method of performing spinal fusion using clamp 200 is shown in FIGS. 25-35. It should be understood that while the exemplary method of performing spinal fusion is shown and described in connection with clamp 200, the exemplary method may be used in connection with any other clamps described herein or otherwise hereafter known. The method may be used in connection with an open midline approach, a minimal invasive procedure, etc. FIGS. 26 and 27 show exemplary tools that may be employed in the procedure, namely a flexible guide wire 300, a flexible guidewire holder 310, and a rod clamp insertion instrument 320.

Referring to FIG. 27, the guide wire 300 may be inserted through a small incision into a pre-made hole formed in the first (possibly caudal) vertebra using the guide wire holder 310. An anterior-posterior and lateral image may be used to ensure proper guide wire 300 positioning. Subsequently a first bone anchor may be implanted using the implanted guide wire 300 as a guide. Thereafter, the guide wire 300 may be removed.

Figure 28:
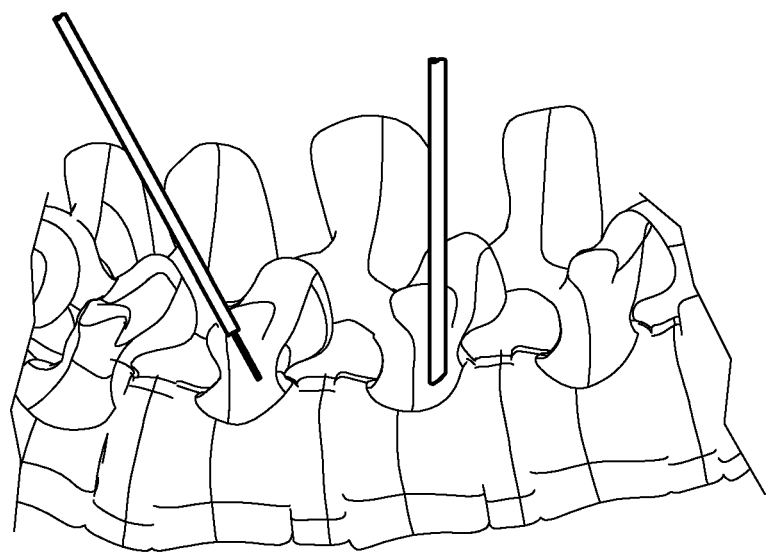

Referring to FIG. 28, a second guide wire 300 may be inserted through a small incision into a pre-made hole formed in a second vertebra using the guide wire holder 310. Once again, an anterior-posterior and lateral image may be used to ensure proper guide wire 300 positioning. This step may be repeated as often as necessary depending on the number of vertebrae being stabilized and/or fused and the procedure being performed.

Figure 29:
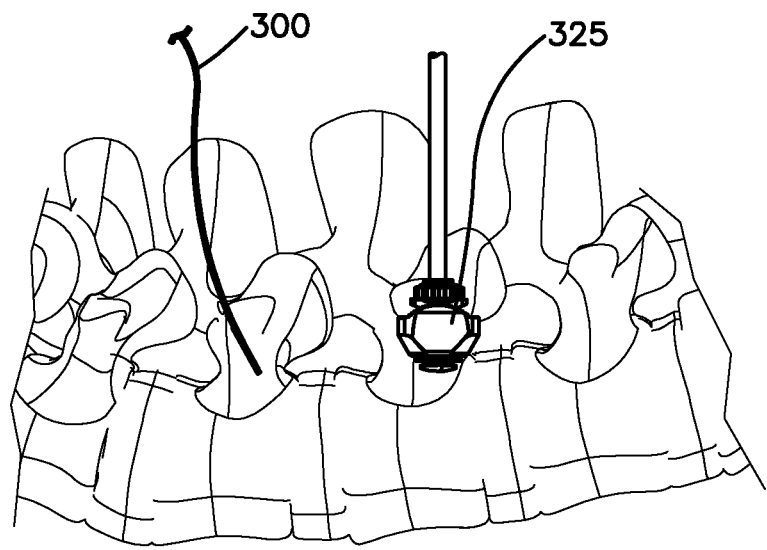

Referring to FIG. 29, a clamp 325, preferably a lateral clamp, may be secured onto the first bone anchor, which has been implanted into the first vertebrae.

Figure 30:
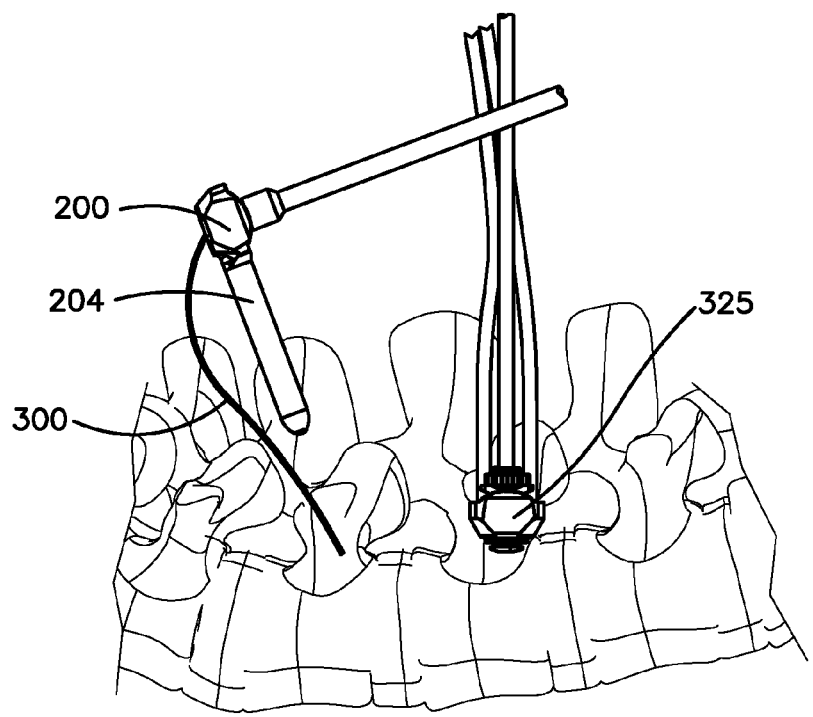

Referring to FIG. 30, using the second guide wire 300, which was inserted into the second vertebra, as a guide, the monolithic and/or integral rod 204 formed on the clamp 200 may be inserted into the clamp 325. The clamp 200 may be implanted using the cannulated rod clamp insertion instrument 320.

Figure 31:
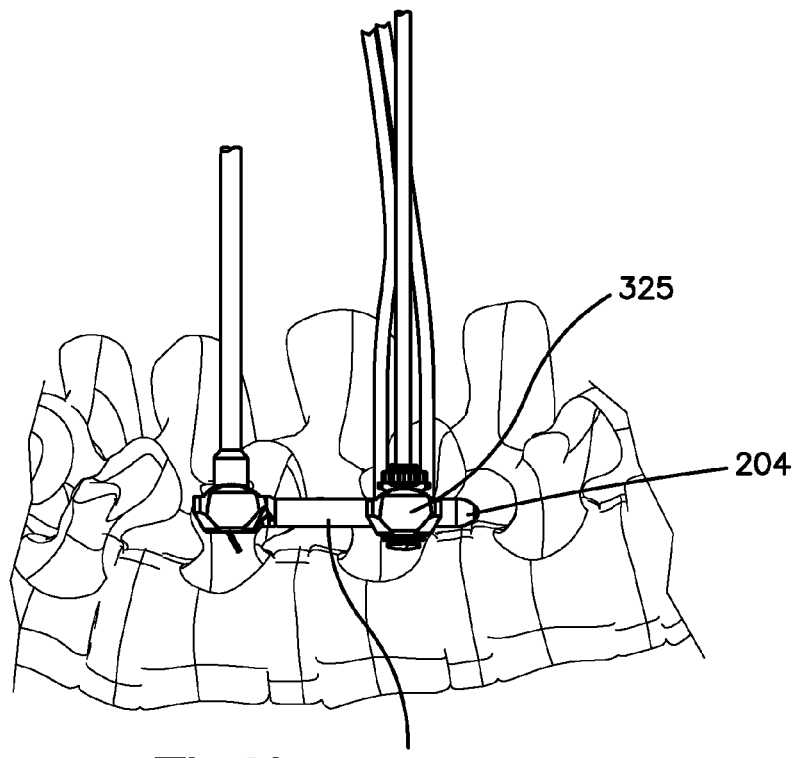
Figure 32:
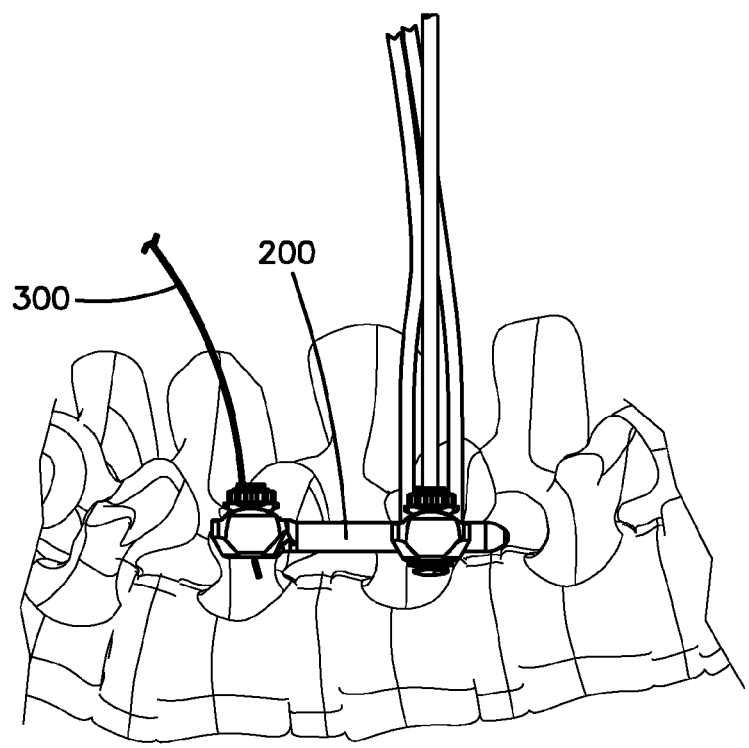

Referring to FIG. 31, the monolithic and/or integral rod 204 formed on the clamp 200 may be inserted through the clamp 325. Next, as shown in FIG. 32, the rod clamp insertion instrument 320 may be removed.

Figure 33:
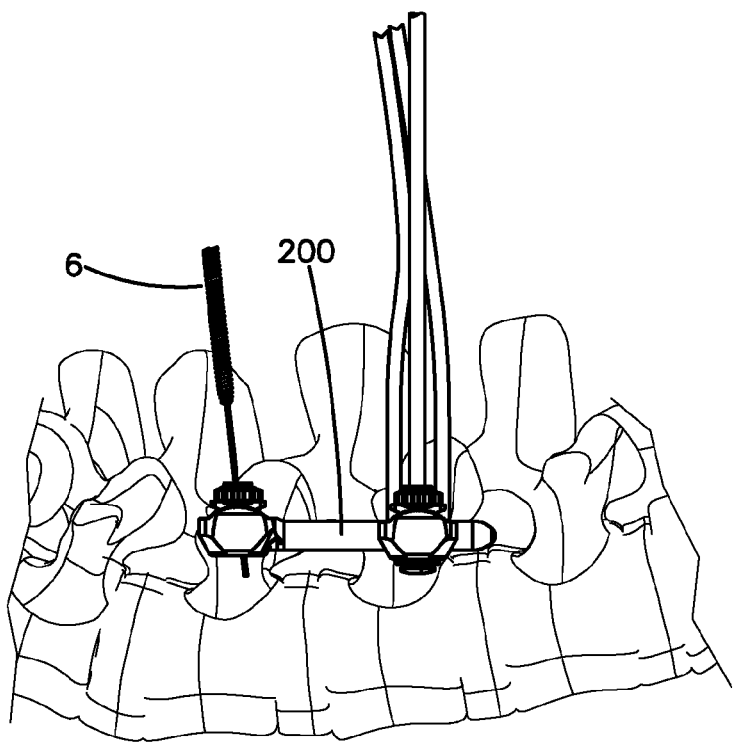
Figure 34:
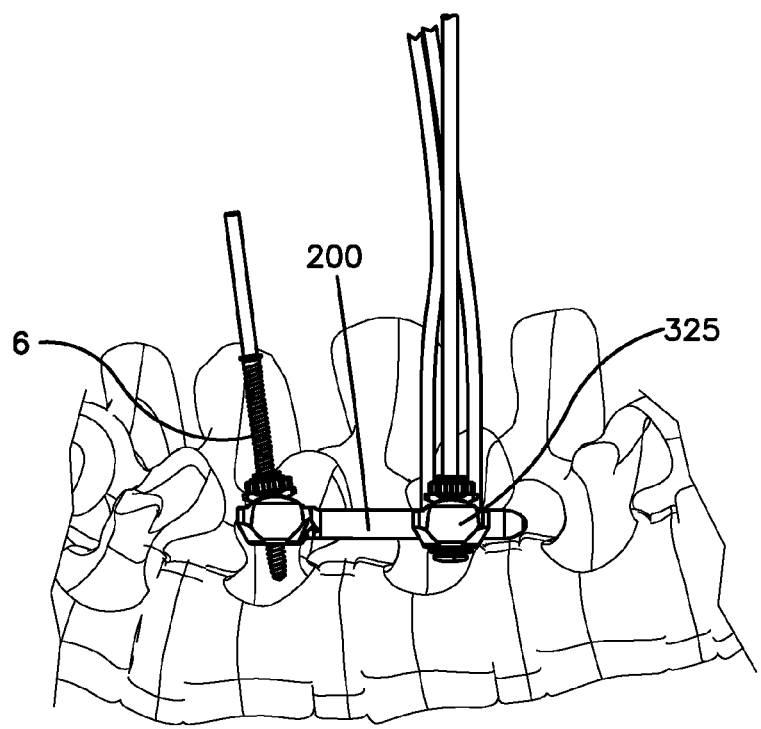
Figure 35:
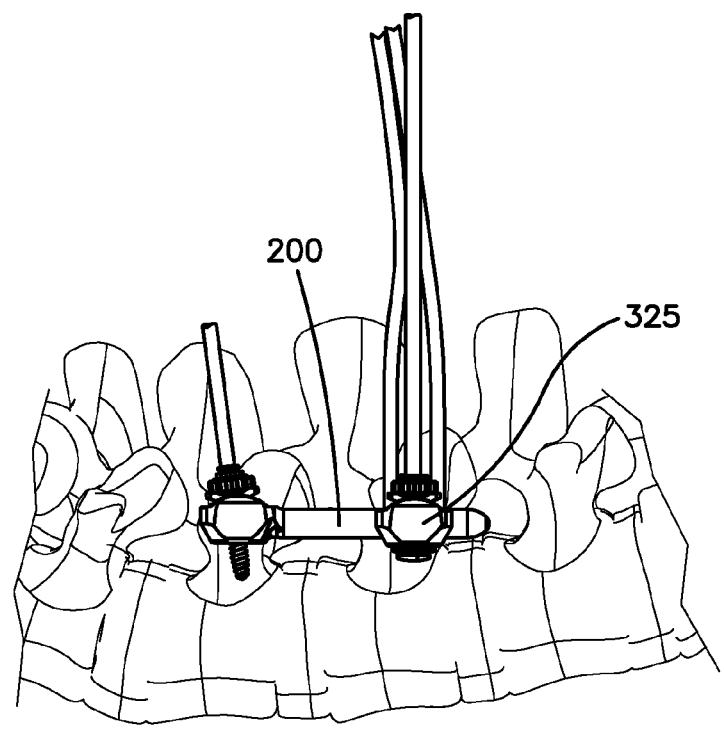

Referring to FIGS. 33 and 34, using the second guide wire 300 as a guide, a second bone anchor 6 may be implanted through the clamp 200 and into engagement with the patient's vertebra. The second guide wire 300 may then be removed. Finally, as shown in FIG. 35, tightening of the nut on clamp 200 and clamp 325 is performed. In addition, optionally, lordosis and/or kyphosis correction may be performed and the ends of the bone anchors may be cut and removed.

Since clamp 200 incorporates a monolithic and/or integral rod 204 a shorter rod than would otherwise be necessary may be included on the clamp 200 and no assembly or set screw is required.

It should be understood that while the exemplary embodiment of performing spinal fusion was shown and described using clamp 200 and a lateral clamp 325, any number of different clamps can be used. For example, two lateral clamps may be used wherein a first bone anchor and a first clamp is implanted. The rod may then be guided through a second clamp then through the already installed first clamp. Then a second screw may be inserted through the second clamp, once the rod is in place.

Figure 36:
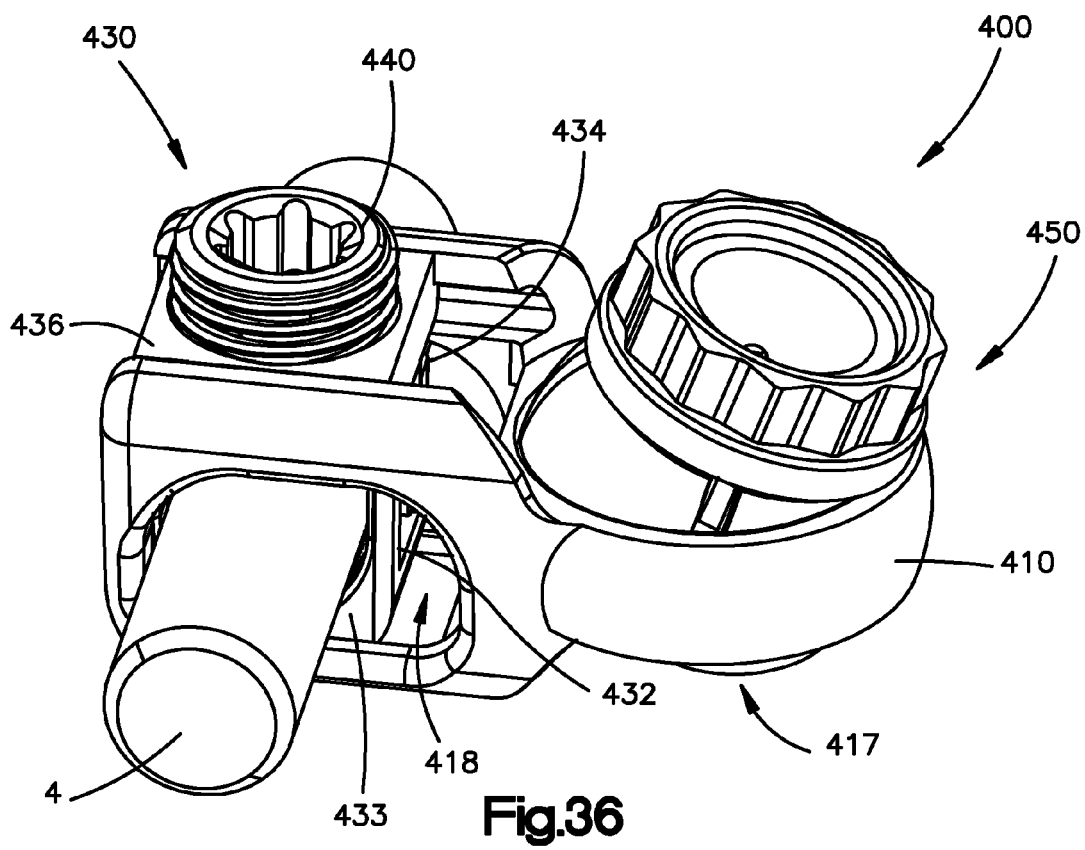
FIG. 36 is an alternate exemplary embodiment of a clamp.

As shown in FIG. 36, an alternate exemplary embodiment of a clamp 400 is shown. In this embodiment, the clamp 400 may include a housing 410 having a first throughbore 417 and a second throughbore 418, a rod clamping assembly 430 and a bone anchor clamping assembly 450. The first throughbore 417 being sized and configured to receive at least a portion of the bone anchor clamping assembly 450 for fixing the position of a bone anchor 6 (not shown) with respect to the housing 410. The structure and operation of the bone anchor clamping assembly 450 may be substantially similar to the bone anchor clamping assembly 50 described above in connection with clamp 10.

Figure 36A:
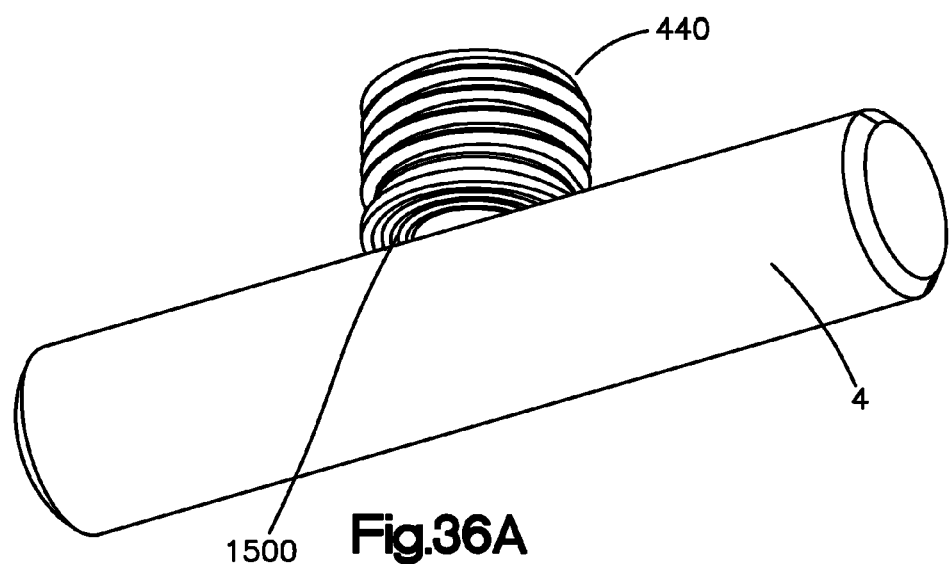
FIG. 36a is an exemplary embodiment of a set screw or nut incorporating concentric ridges which may be used in connection with one of the clamps.

The rod clamping assembly 430 may include a gripping element 432 (shown as a loop shaped gripping element), a slider member 436 (shown as a plate), a nut 440 and an optional collar (not shown). The collar preferably being located in-between the nut 440 and the gripping element 432 so that rotation of the nut 440 causes the collar to contact the rod 4 located within the gripping element 432, as will be described in greater detail below. As will be generally appreciated by one of ordinary skill in the art, incorporation of the collar is optional. For example, the nut 440 may be configured to directly contact the longitudinal rod 4. Preferably, if and when the nut 440 is sized and configured to directly contact the longitudinal rod 4, the tip of the nut 440 is configured to incorporate a plurality of concentric ridges 1500 to increase rod push-through force. That is, when a nut or set screw is used to directly contact a rod, preferably the tip of the nut or set screw is equipped with two or more concentric circles 1500 in order to maximize rod push-through force for a given tightening torque, as schematically represented in FIG. 36*a*.

The gripping element 432 may include a lower portion 433 and an upper portion 434, the lower portion 433 being disposed within the second throughbore 418 for receiving at least a portion of the longitudinal rod 4. The upper portion 434 of the gripping element 432 being operably coupled to the slider member 436. The slider member 436 is operably coupled to the housing 410. For example, as shown, the slider member 436 and housing 410 may be connected to one another via a dovetail arrangement. Alternatively, as will be appreciated by one of ordinary skill in the art, the slider member 436 may be moveably coupled to the housing 410 by any other means including, but not limited to, a track-plate system, tongue and groove connection, etc. Incorporation of the slider member 436 enables the position of the slider member 436, and hence the gripping element 432 that is connected thereto, to be slidably adjustable with respect to the housing 410 in order to better accommodate the position of the rod 4.

As will be generally appreciated by one of ordinary skill in the art, in use, the nut 440 and collar are operably coupled to one another so that once the position of the longitudinal rod 4 has been properly positioned with respect to the housing 410, rotation of the nut 440 causes a force to be applied to the collar, which in turn compresses the collar against the longitudinal rod 4 causing the rod 4 to be wedged between the collar and gripping element 432. In addition, rotation of the nut 440 causes a force to be applied to the slider member 436, which in turn fixes the position of the slider member 436 with respect to the housing 410.

Figure 37:
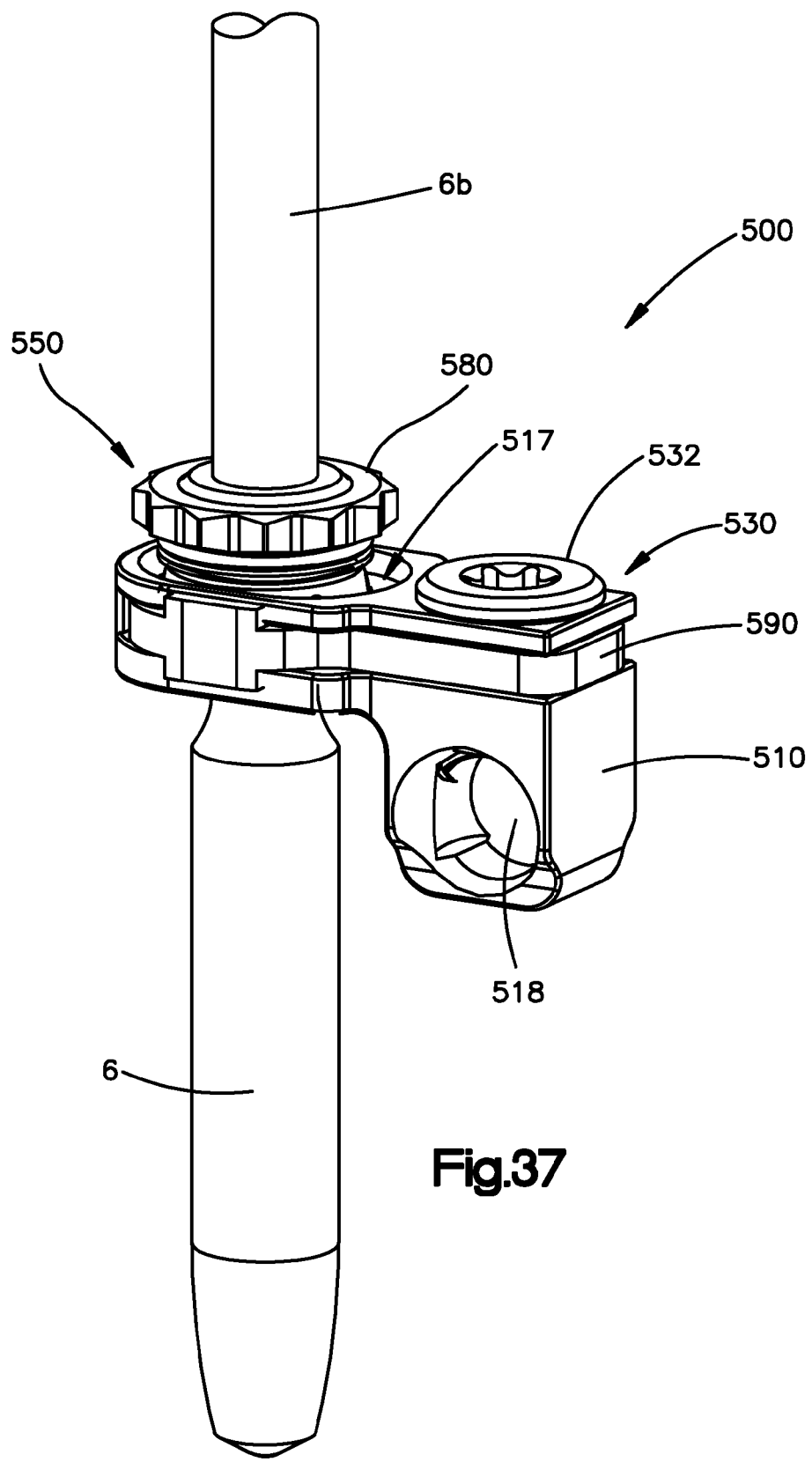
FIG. 37 is an alternate exemplary embodiment of a clamp.
Figure 39:
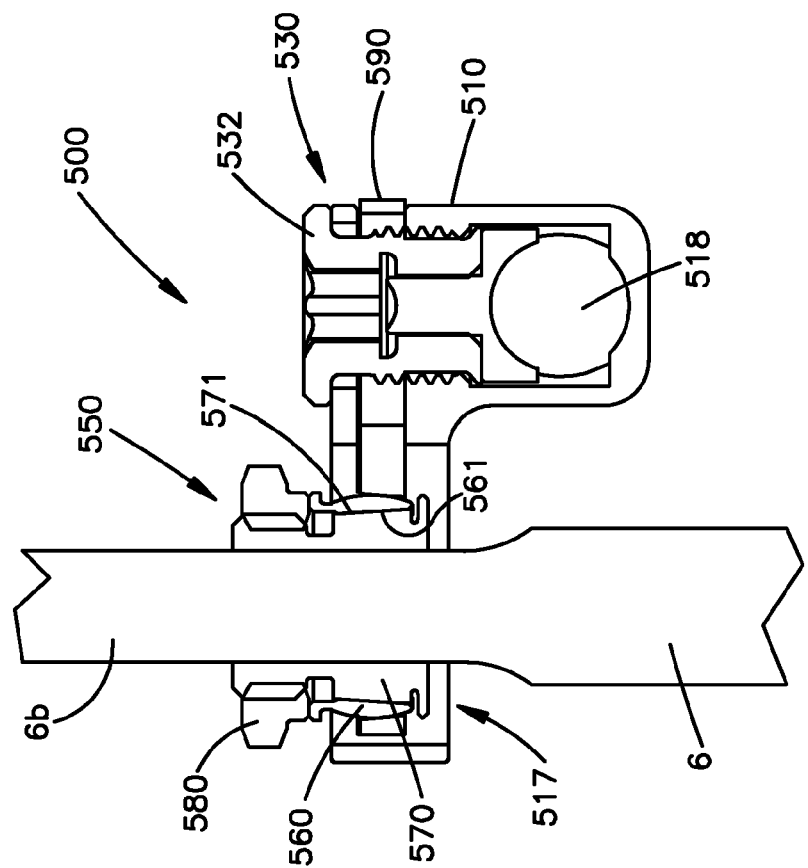
FIG. 39 is a cross-sectional view of the clamp shown in FIG. 37.
Figure 38:
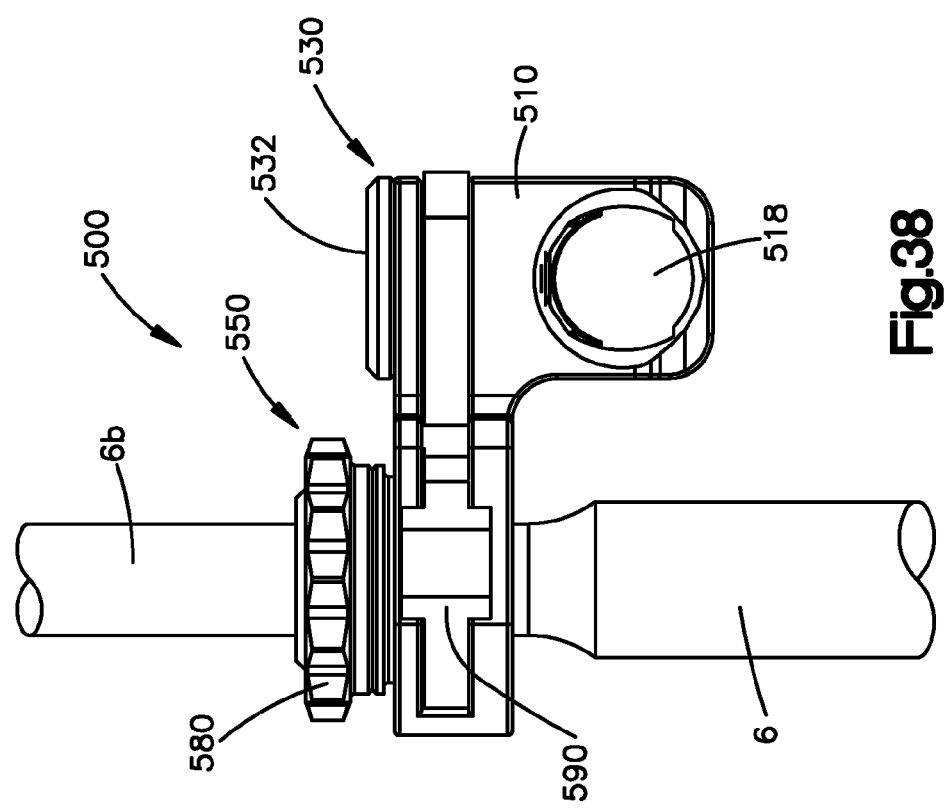
FIG. 38 is a side view of the clamp shown in FIG. 37.

As shown in FIGS. 37-39, another exemplary embodiment of a clamp 500 is shown. In this embodiment, the clamp 500 may include a housing 510 having a first throughbore 517 and a second throughbore 518, a rod clamping assembly 530 and a bone anchor clamping assembly 550. In this embodiment, the rod clamping assembly 530 may be in the form of a set screw 532 sized and configured to be received within the housing 510 in operational engagement with the second throughbore 518 formed in the housing 510 so that rotation of the set screw 532 causes the set screw 532 to contact the portion of the longitudinal rod 4 located in the second throughbore 518 thereby fixing the position of the rod 4 with respect to the housing 510. That is, in use, rotation of the set screw 532 causes the set screw 532 to move with respect to the housing 510, which in turn causes the rod 4 to be wedged between the set screw 532 and the housing 510.

The first throughbore 517 is preferably sized and configured to receive at least a portion of the bone anchor clamping assembly 550. Similar to previous embodiments, the bone anchor clamping assembly 550 may include a bushing 560, a collet 570, and a nut 580 for fixing the position of the bone anchor 6 with respect to the housing 510. In this embodiment however, the bushing 560 and the collet 570 may be configured with corresponding tapered surfaces 561, 571. In use, as will be generally appreciated by one of ordinary skill in the art, since the nut 580 is in threaded engagement with the collet 570, rotation of the nut 580 causes the collet 570 to move with respect to the nut 580. Moreover, since the nut 580 is generally located above the bushing 560, the nut 580 eventually may contact the bushing 560 and thus prevent it from moving with respect to the nut 580. Thus rotation of the nut 580 causes the collet 570 to move with respect to the bushing 560, which in turn causes the position of the bushing 560 and collet 570 to be fixed with respect to one another and with respect to the housing 510. The bushing 560 and collet 570 may include any other corresponding shapes including, but not limited to, spherical, conical, etc.

The housing 510 also preferably includes a slider member 590 operably coupled thereto. As shown, the slider member 590 enables the position of the bone anchor clamping assembly 550, and hence the position of the bone anchor 6, to be moveably adjustable with respect to the housing 510, and hence with respect to the longitudinal rod 4. One of the unique features of this embodiment is that rotation of the rod clamping assembly (e.g. set screw 532) causes a force to be applied to the slider member 590, and hence causes the slider member 590 to be wedged between the rod clamping assembly 530 and the housing 510 which, in turn, fixes the position of the slider member 590 with respect to the housing 510. That is, in contrast to the previously described embodiments of the clamp, the position of the slider member 590 is fixed by rotating the rod clamping assembly 530. Thus, the lateral position of the longitudinal rod 4 is fixed with respect to the bone anchor 6 when the position of the rod 4 is fixed. Thereafter, the bone anchor 6 may still be able to polyaxially angulate with respect to the housing 510 until the nut 580 is tightened.

Figure 40:
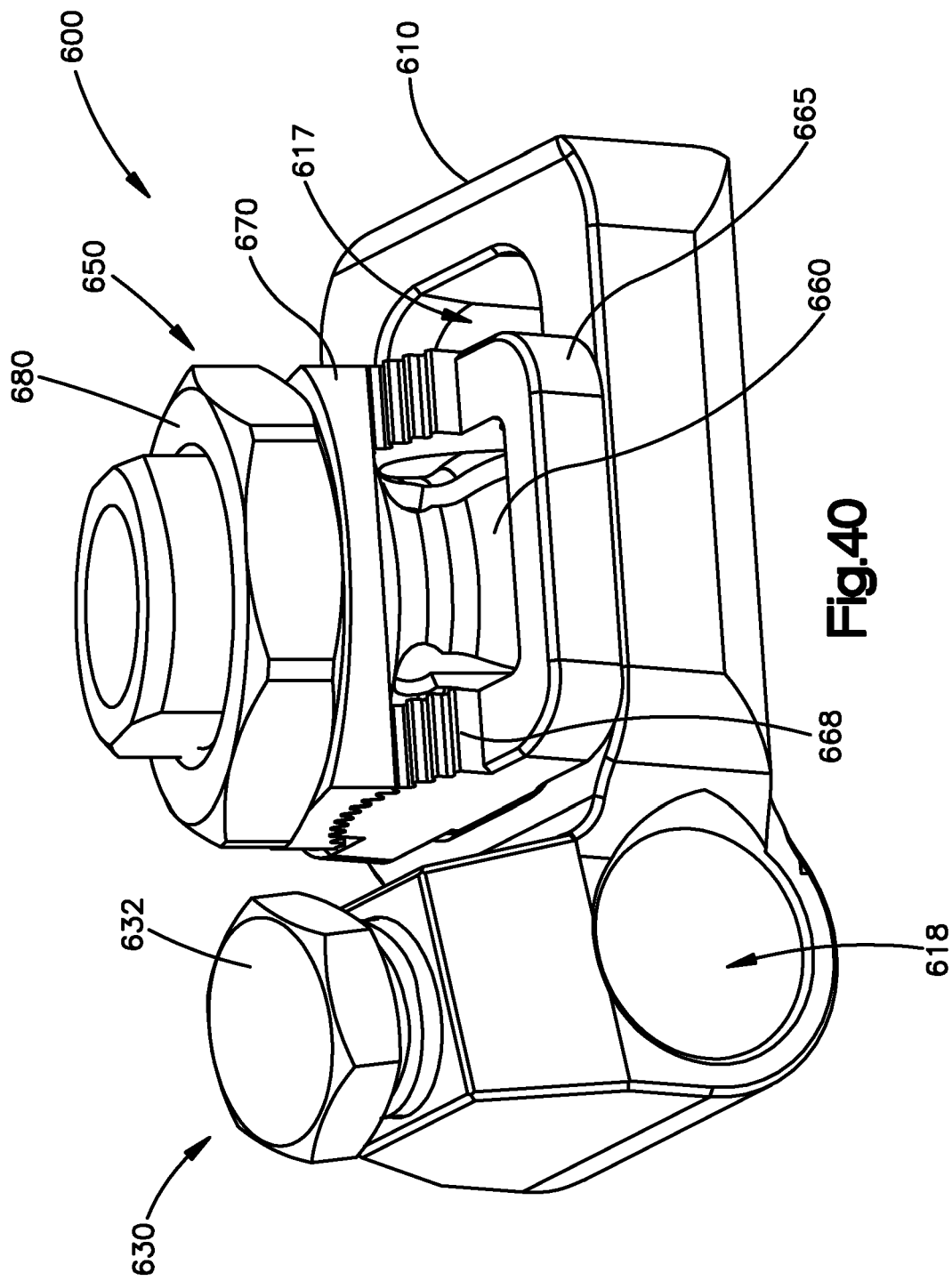
FIG. 40 is an alternate exemplary embodiment of a clamp.

As best shown in FIG. 40, another exemplary embodiment of a clamp 600 is shown. In this embodiment, the clamp 600 may include a housing 610 having a first throughbore 617 and a second throughbore 618, a rod clamping assembly 630 and a bone anchor clamping assembly 650. In this embodiment, the rod clamping assembly 630 may be in the form of a set screw 632. Rotation of the set screw 632 causing the longitudinal rod (not shown) to be fixed with respect to the housing 610. As shown, the first throughbore 617 preferably is in the form of an elongated slot so that the bone anchor clamping assembly 650, which is operably coupled to the first throughbore 617, can move within the slot so that the lateral position of the rod with respect to the bone anchor (not shown) can be adjusted.

Similar to the bone anchor clamping assembly 150 previously described, the bone anchor clamping assembly 650 may include a collet 660, a bushing 665, a slider member 670 and a nut 680. In this embodiment however, the bushing 665 preferably includes one or more ridges 668 for contacting the slider member 670 as opposed to the ridges being formed on the housing. In this way, the slider member 670, and hence the collet 660 and bone anchor, are able to translate and pivot with respect to the housing 610.

Figure 41:
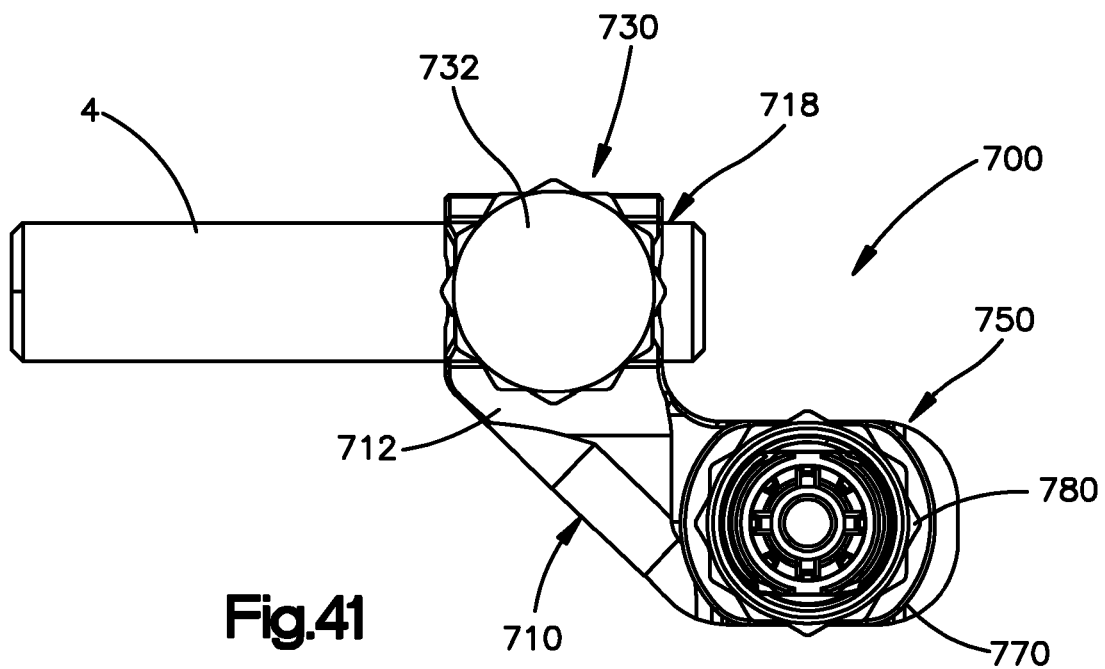
FIG. 41 is an alternate exemplary embodiment of a clamp.
Figure 42:
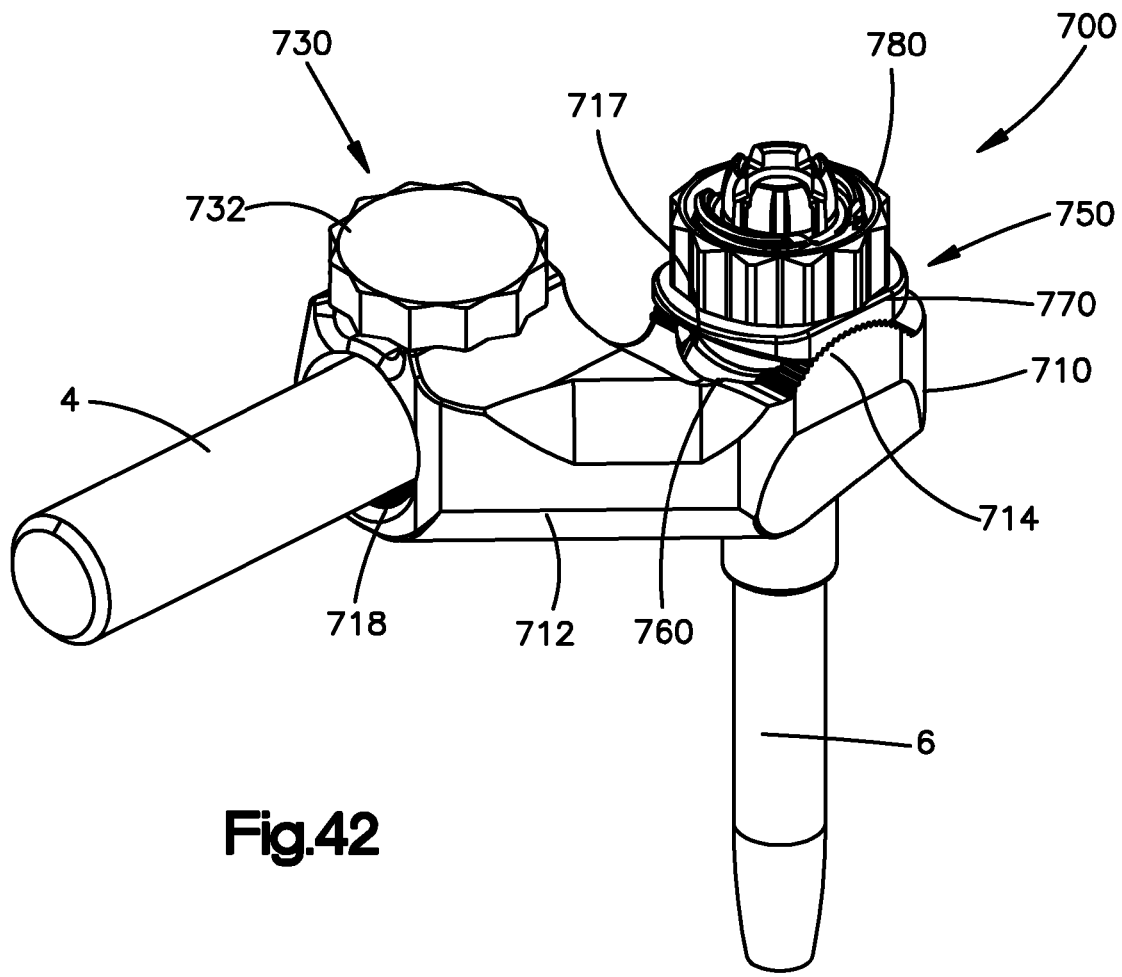
FIG. 42 is a perspective view of the clamp shown in FIG. 41.

As best shown in FIGS. 41 and 42, another exemplary embodiment of a clamp 700 is shown. In this embodiment, the clamp 700 may include a housing 710, preferably in the form of an L-shaped plate 712 to allow for medial-lateral and cranial-caudal offset, having a first throughbore 717 and a second throughbore 718 preferably located at opposite ends of the L-shaped plate 712. The shape and configuration of the clamp 700 makes it particularly useful for sparing the facet (e.g., avoiding contact with the facet so that the facet is not touched and/or damaged).

The clamp 700 may also include a rod clamping assembly 730 and a bone anchor clamping assembly 750, the rod clamping assembly 730 may be in the form of a set screw 732. Rotation of the set screw 732 causing the position of the longitudinal rod 4 to be fixed with respect to the housing 710. The first throughbore 717 is preferably in the form of an elongated slot so that the bone anchor clamping assembly 750, which is operably coupled to the first throughbore 717, can move within the slot so that the lateral position of the housing 710 can be moved with respect to the bone anchor 6. As previously described in connection with clamp 100, the bone anchor clamping assembly 750 may include a collet 760, a slider member 770, and a nut 780. As shown, the housing 710 may include one or more ridges 714 for contacting the slider member 770. In this way, the bone anchor clamping assembly 750, and hence the bone anchor 6, is able to pivot with respect to the housing 710. The portion of the L-shaped plate 712 that surrounds the bone anchor clamping assembly 750 is preferably minimized in size to preserve the superior facet of the patient's vertebra.

Figure 43:
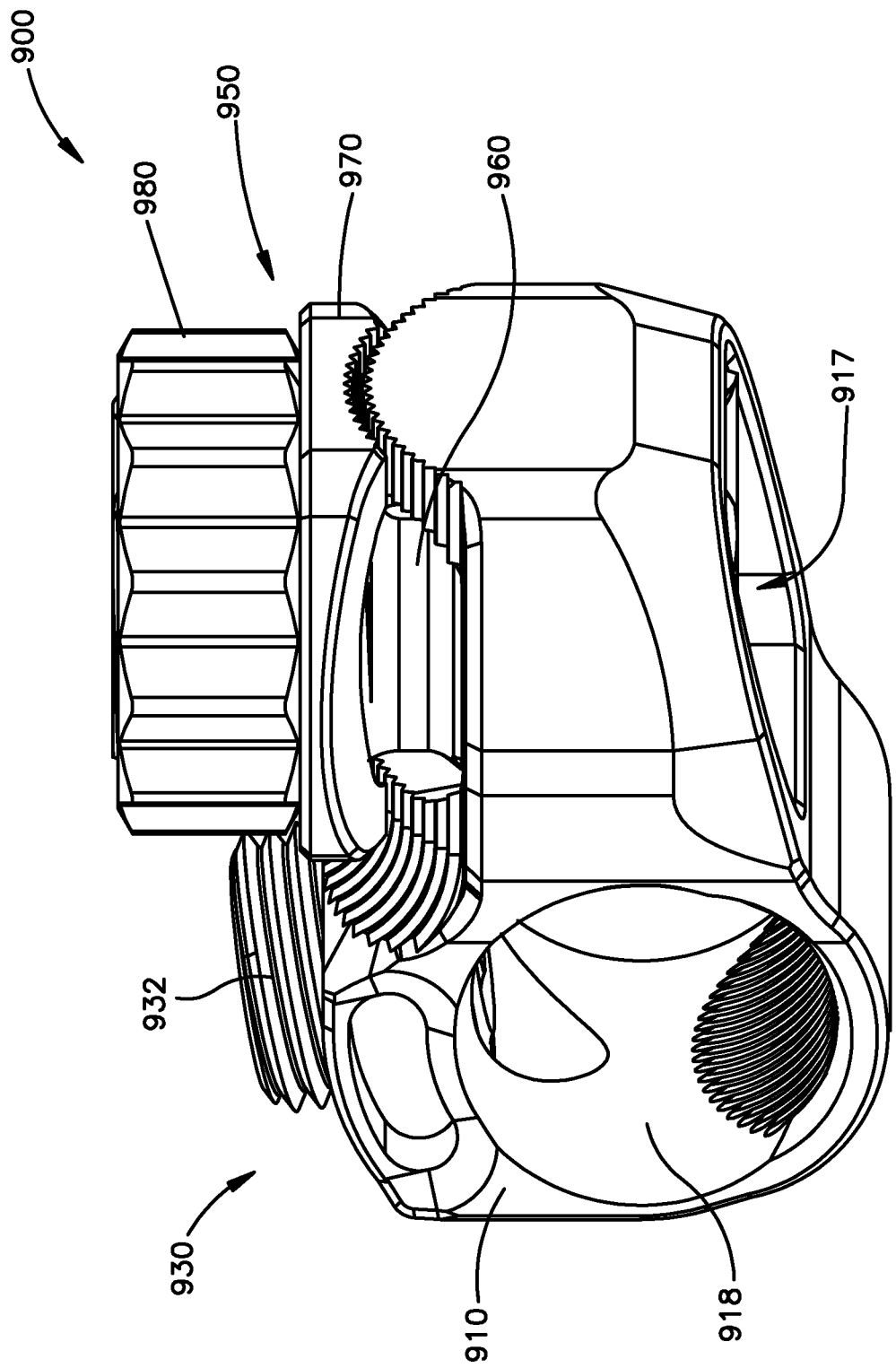
FIG. 43 is an alternate exemplary embodiment of a clamp.
Figure 44:
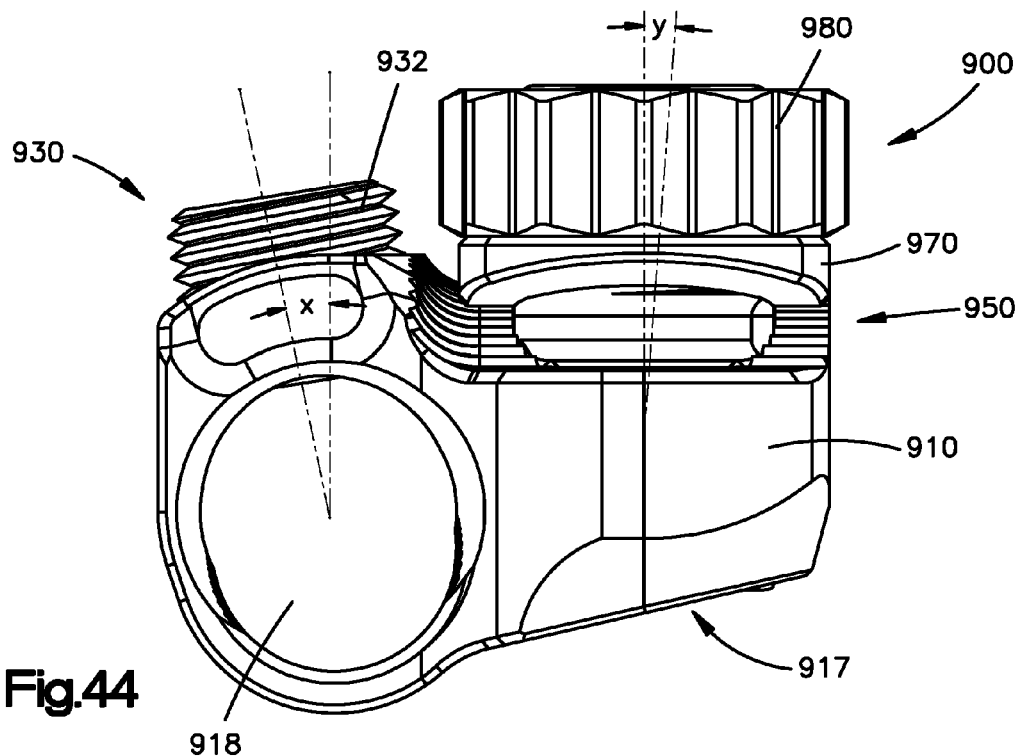
FIG. 44 is a side view of the clamp shown in FIG. 43.
Figure 45:
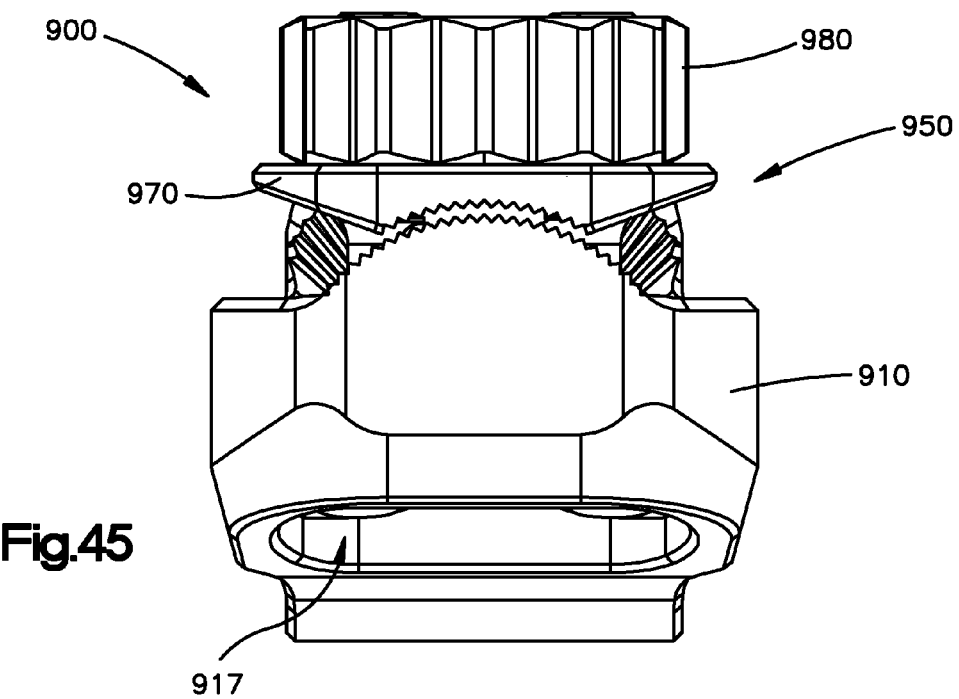
FIG. 45 is a lateral view of the clamp shown in FIG. 43.
Figure 49:
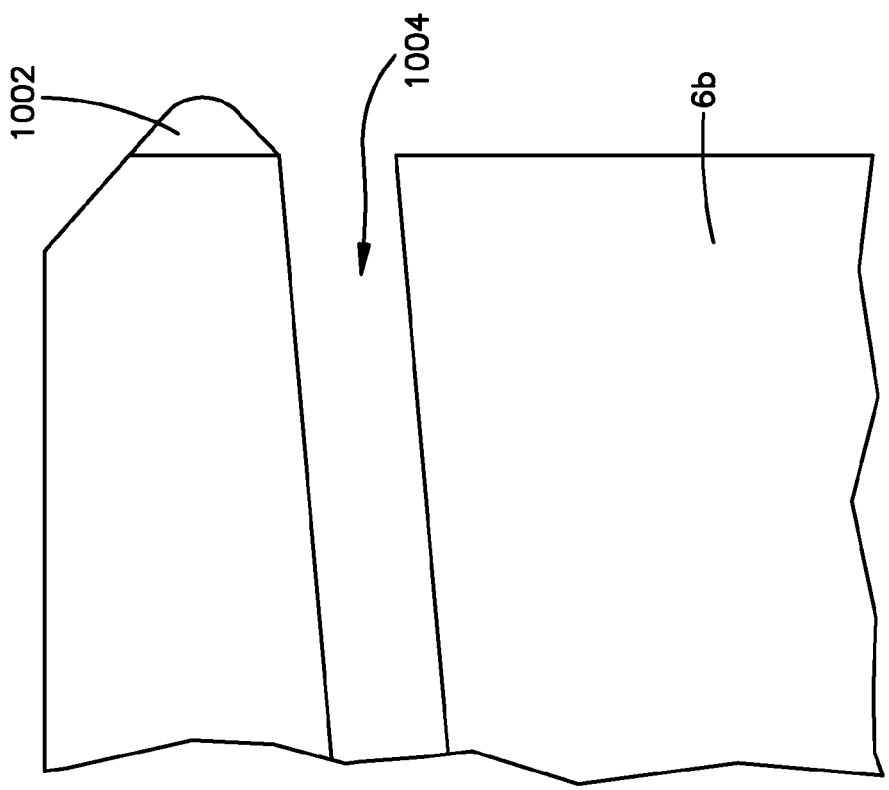
FIG. 49 is an alternate view of the retention clip of FIG. 46.
Figure 50:
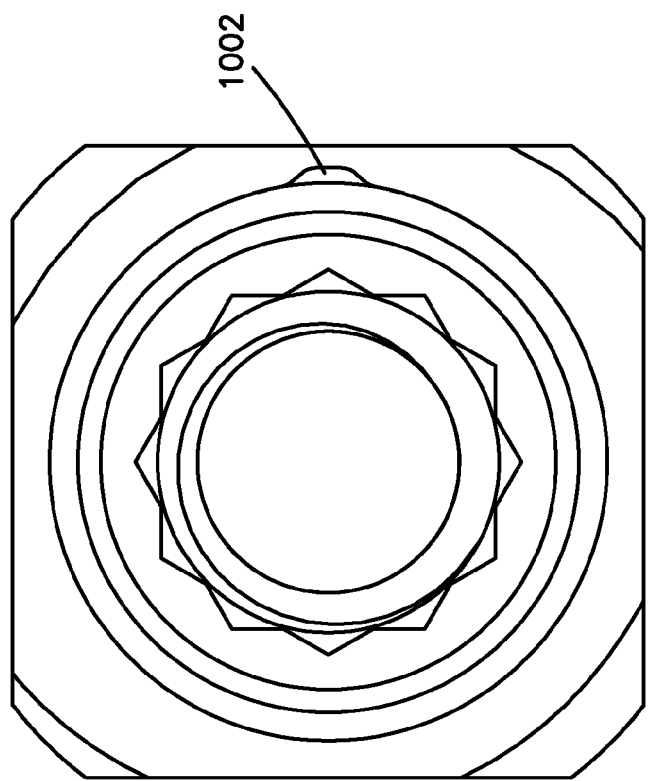
FIG. 50 is an alternate view of the retention clip of FIG. 46.
Figure 58:
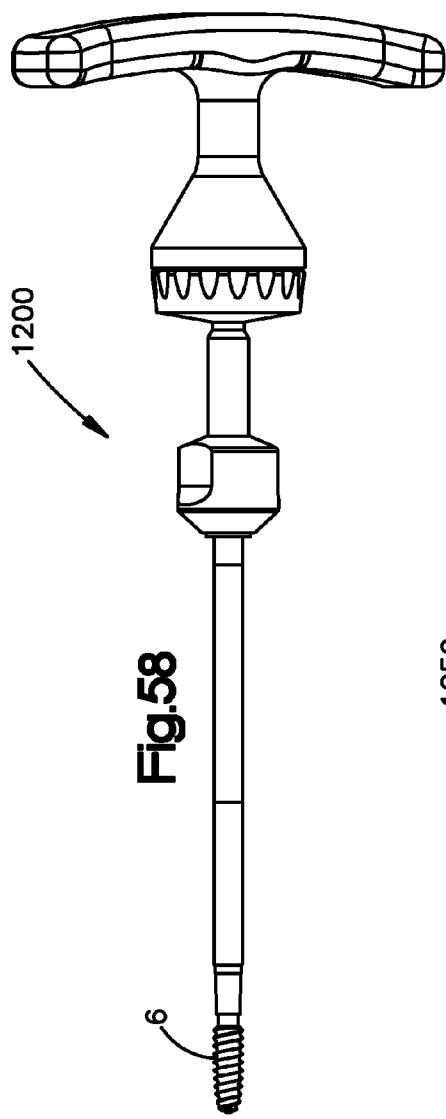
Figure 59:
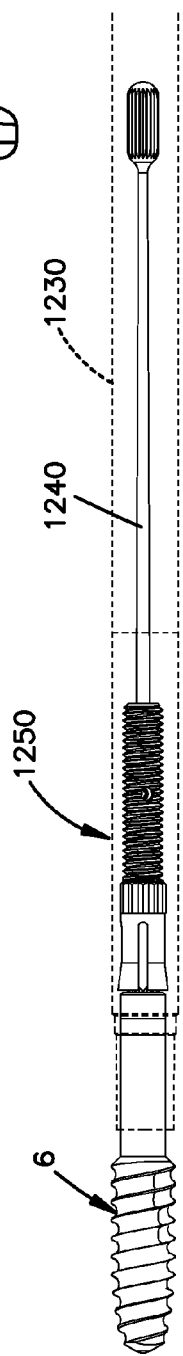
Figure 60:
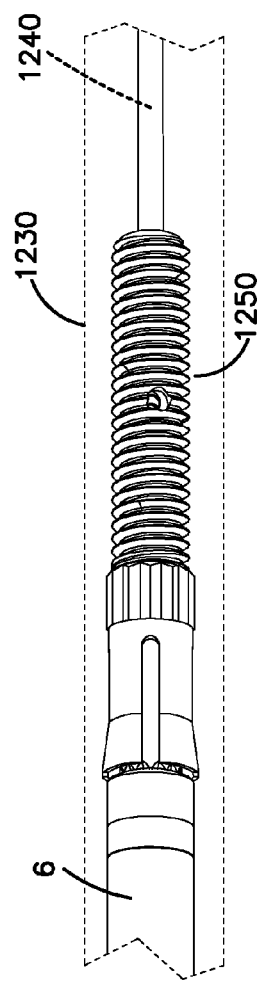

As shown in FIGS. 43-45, an alternate embodiment of a clamp 900 is shown. In this embodiment the clamp 900 may include a housing 910 having a first throughbore 917 and a second throughbore 918, a rod clamping assembly 930 and a bone anchor clamping assembly 950. In this embodiment, the rod clamping assembly 930 may be in the form of a set screw 932. The set screw 932 may include a plurality of concentric ridges (not shown) for contacting the outer surface of the longitudinal rod, as previously described. Rotation of the set screw 932 causes the position of the longitudinal rod to fixed with respect to the housing 910. As shown, the bone anchor clamping assembly 950 may include a collet 960, a slider member 970 and a nut 980 as previously described herein, although other bone anchor clamping assemblies may be used.

Preferably, clamp 900 is sized and configured to minimize the distance between the bone anchor and the longitudinal rod. This object may be accomplished by positioning the first throughbore 917 for receiving the bone anchor clamping assembly 950 and the second throughbore 918 for receiving the longitudinal rod as close as possible to one another. Moreover, as best shown in FIG. 44, preferably the axis of the rod clamping assembly (e.g., set screw 932) is angled X with respect to the longitudinal axis of the second throughbore 918 and the axis of the bone anchor clamping assembly 930 is angled Y with respect to the longitudinal axis of the first throughbore 917 so that the rod to bone anchor offset is minimized. The axis of the rod clamping assembly (e.g., set screw 932) may be at an angle X of approximately 15 degrees with respect to the longitudinal axis of the second throughbore 918 and the axis of the bone anchor clamping assembly 930 may be angled Y at an angle of approximately 5 degrees with respect to the longitudinal axis of the first throughbore 917. It should be noted that other angles are envisioned. Moreover, as shown, preferably the collet 960 is truncated so that the width of the bone anchor clamping assembly 950 is minimized.

Referring to FIGS. 46-50, an exemplary embodiment of an optional retention clip for use in maintaining the bone anchor in the clamp, such as the clamps described above, will now be described. The retention clip 1000 may be located adjacent the proximal end of the bone anchor 6. As shown, the retention clip 1000 preferably includes a projection 1002 extending from the shaft portion 6b of the bone anchor 6. Preferably, the projection 1002 is integrally formed with the bone anchor 6. More preferably, the projection 1002 extends from the proximal end of the shaft portion 6b of the bone anchor 6 for reasons that will become apparent. The projection 1002 may include a ramp like surface in order to facilitate translation of the clamp over the bone anchor 6 and past the retention clip 1000. It should be noted however that the size and shape of the projection 1002 may be modified for various applications, and the retention clip 1000 should not be limited by the particular shape or size of the projection 1002.

The retention clip 1000 also preferably includes a slot 1004 formed in the bone anchor 6 adjacent to the projection 1002. As will be appreciated by one of ordinary skill in the art, the slot 1004 enables the retention clip part 1000 of the bone anchor 6 to be elastically flexible.

In use, the clamp, and in particular the bone anchor clamping assembly may be slid over the proximal end of the shaft portion 6b of the bone anchor 6. At this point, the retention clip 1000 flexes in order to permit the clamp to pass over the bone anchor 6. Once the clamp has been slid beyond the retention clip 1000, the clamp is prevented from accidentally becoming disassembled from the bone anchor 6 by the projection 1002. If the user desires to disassemble the bone anchor 6 from the clamp, the retention clip 1000 may enable the clamp and bone anchor 6 to be separated under additional load. That is, once the clamp has been slid beyond the retention clip 1000, the retention clip 1000 preferably deflects back to its original shape, thereby positioning the projection 1002 above the top surface of the clamp, and thus preventing the clamp from sliding apart from the bone anchor 6, without application of additional force.

Referring to FIGS. 51-57, an exemplary clamp insertion instrument 1100 that may be used to insert the bone anchor 6 and clamp 10 will be described. It should be understood however that while the clamp insertion instrument 1100 will be shown as and described in connection with implantation of clamp 10, the clamp insertion instrument 1100 may be easily modified to implant other clamps including those herein described or otherwise known.

The insertion instrument 1100 may include a handle member 1110 (shown as a T-handle), a sleeve member 1120, and a drive member 1130. The sleeve member 1120 preferably includes a proximal end 1122, a distal end 1124 and a bore 1126 extending from the distal end 1122 to the proximal end 1124. The bore 1126 being sized and configured to receive at least a portion of the drive member 1130. The proximal end 1122 may be operably associated with the handle member 1110 so that movement of the handle member 1110 results in movement of the sleeve member 1120.

The drive member 1130 preferably includes a proximal end 1132 and a distal end 1134, the distal end 1134 preferably includes one or more threads 1135 for threadably engaging a drive recess formed in the bone anchor 6 (although other type of connections may be used). The proximal end 1132 of the drive member 1130 is preferably coupled to a guide member 1140. More preferably, the drive member 1130 is rigidly coupled to the guide member 1140. Alternatively, however, the drive member 1130 and guide member 1140 may be coupled by any other means. It is also contemplated that the drive member 1130 and guide member 1140 may be integrally formed.

The drive member 1130 also preferably includes a drive sleeve member 1150, the drive sleeve member 1150 may include a proximal end 1152, a distal end 1154 and a bore 1156 extending from the proximal end 1152 to the distal end 1154. The bore 1156 being sized and configured to receive the drive member 1130, and optional guide member 1140, therein. As shown, the distal portion 1154 of the drive sleeve member 1150 may also be sized and configured to contact the drive recess formed in the bone anchor 6. The drive sleeve member 1150 preferably also includes one or more threads 1158 for engaging one or more threads formed on the inner surface 1127 of the sleeve member 1120. The drive sleeve member 1150 preferably also includes one or more flexible fingers 1160 formed on the outer surface thereof. The fingers 1160 in their unflexed state are preferably wider than the diameter of the bore formed in the sleeve member 1120 such that moving the sleeve member 1120 over the drive sleeve member 1150 causes the fingers 1160 to inwardly deflect.

In use, the insertion instrument 1100 may be used to couple the clamp 10 to the bone anchor 6. Once the bone anchor 6 has been properly implanted, the drive member 1130 may be coupled to the bone anchor 6. Next, the drive sleeve member 1150 may be coupled to the bone anchor 6 using the guide member 1140, which may be operably coupled to the drive member 1130, as a guide. Thereafter, as best shown in FIG. 53, the guide member 1140 may be used to guide the clamp 10 into place on the shaft portion 6b of the bone anchor 6. As best shown in FIGS. 55-57, once the clamp 10 has been positioned onto the guide member 1140, the sleeve member 1120 may be placed over and moved with respect to the guide member 1140 until the threads formed on the inner surface 1127 of the sleeve member 1120 contact the threads 1158 formed on the drive sleeve member 1150. Thereafter, the sleeve member 1120 may be rotated, using the handle portion 1110, with respect to the drive member 1130 and drive sleeve member 1150. As will be generally appreciated by one of ordinary skill in the art, movement of the sleeve member 1120 with respect to the drive member 1130 and drive sleeve member 1150 causes the clamp 10 to move into operably engagement with the shaft portion 6b of the bone anchor 6. Once the clamp 10 has been properly positioned onto the bone anchor 6, the sleeve member 1120 may be removed. As best shown in FIG. 57, at this point in time, the flexible fingers 1160 formed on the drive sleeve member 1150 deflect outwards retaining the clamp 10 onto the bone anchor 6.

Referring to FIGS. 58-64, an alternate exemplary insertion instrument 1200 is shown. In this embodiment, as best shown in FIG. 61, the drive member 1230, the guide member 1240, and the drive sleeve member 1250 may be integrally formed. In use, the operation of the insertion instrument 1200 is substantially identical to the operation of insertion instrument 1100 described above.

An alternative exemplary embodiment of a drive member 1330 and a guide member 1340 are shown in FIG. 65. As shown, the drive member 1330 may be sized and configured to articulate with respect to the bone anchor 6. In addition and/or alternatively, the drive member 1330 may be sized and configured to articulate with respect to the guide member 1340.

As will be appreciated by those skilled in the art, any or all of the components described herein may be provided in sets or kits so that the surgeon may select various combinations of components to perform a fixation procedure and create a fixation system which is configured specifically for the particular needs/anatomy of a patient. It should be noted that one or more of each component may be provided in a kit or set. In some kits or sets, the same device may be provided in different shapes and/or sizes.

While directional terms such as vertical, horizontal, top, bottom, etc. were used in describing various embodiments, it will be understood that the terms were only used in reference to the illustrations. In use, the embodiments may be oriented in any direction and vertical may become horizontal, top may become bottom, etc.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, the various housing, rod clamping assemblies and/or bone anchor clamping assemblies may be interchangeable. The presently disclosed embodiments are therefore to be considered in all respects as illustrative and not restrictive, the scope of the invention being indicated by the appended claims, and not limited to the foregoing description.

What is claimed is:

1. A clamp for securing a bone anchor with respect to a rod, the bone anchor including a bone engaging portion and an extending portion, the clamp comprising:

a housing defining an external surface, a first housing portion and a second housing portion spaced apart from the first housing portion along a lateral direction, the first housing portion defining a first opening extending through housing along a vertical direction, the vertical direction being perpendicular to the lateral direction, wherein the first opening is configured to receive at least a portion of the extended portion of the bone anchor, the second housing portion defining a second opening, wherein the second opening is configured to receive the rod, the second opening defining a second opening inner surface, wherein the external surface of the housing defines one or more upwardly projecting curved surfaces that extend from the first portion of the housing along the vertical direction, the one or more curved surfaces adjacent to the first opening, the housing further defining a slit extending from the inner surface of the second opening to the external surface adjacent to the first opening, the slit extending along an axis that is angularly offset relative to the vertical and lateral directions, the slit dividing the housing into the first housing portion and the second housing portion so that the housing is elastically deflectable; and a bone anchor clamping assembly carried by the housing and spaced apart from the second opening along the lateral direction, the bone anchor clamping assembly including:

a slider member including a top surface, a bottom surface, and a bore extending from the top surface to the bottom surface, the slider member carried by the first and second housing portions the slider member translatable with respect to the housing a collet positioned at least partially within the first opening, the collet including a top portion, a bottom portion and a collet bore extending from the top portion to the bottom portion, the collet bore configured to receive at least a portion of the extending portion of the bone anchor, the collet including one or more threads, a portion of the collet extending through the bore of the slider member; and a rotatable member carried by the slider member, the rotatable member configured to receive a portion of the extending portion of the bone anchor and at least a portion of the collet;

wherein the clamp has an unlocked configuration and a locked configuration, wherein the unlocked configuration is defined as when the slider member is moveable along the external surface of the first and second housing portions to cause the collet, the rotatable member and the bone anchor to move with respect to the housing, wherein the locked configuration is defined as when rotation of the rotatable member 1) reduces the size of the slit so as to fix the position of the rod received in the second opening with respect to the housing, and 2) engages the collet with the extending portion of the bone anchor so as to fix the position of the bone anchor with respect to the housing.

2. The clamp of claim 1, wherein the collet includes one or more slots extending upwards from the bottom portion, thereby defining one or more deflectable collet fingers.

3. The clamp of claim 2, wherein the bottom portion of the collet includes a substantially curved outer surface for contacting a substantially corresponding internally curved surface formed in the first opening.

4. The clamp of claim 2, wherein the one or more slots is comprised of two slots and the one or more deflectable collet fingers is comprised of two collet fingers.

5. The clamp of claim 2, wherein the collet bore includes an internal threading, the internal threading being engageable with a threading formed on the bone engaging portion of the bone anchor so that the bone anchor can be threaded through the collet bore.

6. The clamp of claim 1, wherein the slider member is in the form of a plate-type member.

7. The clamp of claim 1, wherein rotation of the rotatable member iterates the clamp between the unlocked and locked configurations, wherein rotation of the rotatable member in a first rotational direction moves the rotatable member toward the housing along the vertical direction to apply a force onto the slider member so that the position of the slider member and the position of the received bone anchor are fixed with respect to the housing.

8. The clamp of claim 7, wherein rotation of the rotatable member in the first rotational direction causes the first portion of the housing to move closer to the second portion to compress the slit, thereby decreasing a cross-sectional dimension of the second opening so as to fix the position of the received rod with respect to the housing.

9. The clamp of claim 1, wherein the one or more upwardly projecting curved surfaces is comprised of opposing convex ridges having serrations formed thereon.

10. The clamp of claim 1, wherein movement of the slider member generally parallel to the external surface of the housing causes the bone anchor to angulate with respect to the housing and the rod.

11. A clamping system for mounting to a vertebra, the clamping system comprising:

an elongate rod;

a bone anchor including a bone engaging portion, and an extending portion spaced apart from the bone engaging portion along an anchor axis, the bone engaging portion being sized and configured to be at least partially implanted into the vertebra;

a housing including a first opening and a second opening;

a bone anchor clamping assembly disposed at least partially in the first opening, the bone anchor clamping assembly being polyaxially rotatable relative to the housing, the bone anchor clamping assembly comprising a bushing, a collet and a rotatable member, the bushing including a top portion, a bottom portion, a bore extending from the top portion to the bottom portion and a plurality of slots extending upwards from the bottom portion of the bushing, the slots defining therebetween a plurality of deflectable bushing fingers, the collet at least partially received in the bore of the bushing, the collet defining a top portion, a bottom portion, a collet bore extending from the top portion of the collet, to the bottom portion of the collet, the collet bore configured to receive at least a portion of the bone anchor, and a plurality of collet slots extending upwards from the bottom portion of the collet, thereby defining a plurality of deflectable collet fingers;

wherein the bone anchor clamping assembly has an unlocked configuration and locked configuration, the unlocked configuration is defined as when A) the bone anchor is polyaxially rotatable relative to the housing when the bone anchor is received by the bone anchor clamping assembly, and B) the housing is movable generally parallel to the anchor axis when the bone anchor is implanted in the vertebra, and the locked configuration is defined as when the bone anchor clamping assembly locks 1) an angular orientation of the received bone anchor relative to the housing, and 2) the position of the housing relative to the vertebra when the bone anchor is implanted in the vertebra; and a rod clamping assembly positioned at least partially within the second opening, the rod clamping assembly configured to receive the rod, wherein the rod clamping assembly has a slack configuration and a fastened configuration, wherein the slack configuration is defined as when the rod is movable within the second opening and the fastened configuration is defined as when the rod is fixed in position within the second opening.

12. The clamping system of claim 11, wherein the bottom portion of the bushing includes a substantially spherical outer surface for contacting a substantially corresponding internal surface formed in the housing and defined by the first opening.

13. The clamping system of claim 11 wherein the first opening includes at least one protrusion and the bushing includes at least one recess, the at least one protrusion positioned within the at least one recess in the unlocked configuration to prevent rotation of the bushing with respect to the housing.

14. The clamping system of claim 11, wherein the bore formed in the bushing includes a narrower diameter portion and the collet includes a flared portion so that movement of the collet with respect to the bushing causes the flared portion of the collet to contact the deflectable bushing fingers, thereby biasing the bushing fingers outward into contact with the first opening while simultaneously causing the deflectable collet fingers to be biased inwards against the extending portion of the bone anchor.

15. The clamping system of claim 11, wherein the collet bore includes a narrower portion having a smaller size than a size of the extending portion of the bone anchor so that insertion of the bone anchor into the collet bore causes the extending portion to frictionally couple the bone anchor to the collet.

16. The clamping system of claim 11, wherein the rod has a longitudinal axis, the anchor axis of the bone anchor being spaced apart from the longitudinal axis of the rod so that the anchor axis and the longitudinal axis do not intersect.

17. The clamping system of claim 11, wherein the housing is in the form of a plate having a first portion and a second portion, the first opening being formed in the first portion and the second opening being formed in the second portion, the first portion being angled with respect to the second portion.

18. The clamping system of claim 11 wherein the rod clamping assembly includes a gripping element having a lower portion and an upper portion, the lower portion receiving at least a portion of the rod in the slack and fastened configurations, the upper portion being operably associated with the housing.

19. The clamping system of claim 18, wherein the upper portion of the gripping element is operably coupled to the housing via a second rotatable member.

\* \* \* \* \*

UNITED STATES PATENT AND TRADEMARK OFFICE
CERTIFICATE OF CORRECTION

PATENT NO.       : 8,585,741 B2                                                    Page 1 of 1
APPLICATION NO. : 12/668862
DATED            : November 19, 2013
INVENTOR(S)      : Gabelberger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 894 days.

Signed and Sealed this
Twenty-second Day of September, 2015

Michelle K. Lee
*Director of the United States Patent and Trademark Office*